United States Patent
Yen et al.

(10) Patent No.: US 10,454,045 B2
(45) Date of Patent: Oct. 22, 2019

(54) ORGANIC COMPOUND AND ORGANIC ELECTROLUMINESCENCE DEVICE USING THE SAME

(71) Applicants: Feng-Wen Yen, Taipei (TW); Chin-Min Teng, Miaoli (TW)

(72) Inventors: Feng-Wen Yen, Taipei (TW); Chin-Min Teng, Miaoli (TW)

(*) Notice: Subject to any disclaimer, the term of this patent is extended or adjusted under 35 U.S.C. 154(b) by 190 days.

(21) Appl. No.: 15/854,716

(22) Filed: Dec. 26, 2017

(65) Prior Publication Data

US 2019/0198781 A1 Jun. 27, 2019

(51) Int. Cl.
| | |
|---|---|
| *H01L 51/50* | (2006.01) |
| *H01L 51/00* | (2006.01) |
| *C07D 209/82* | (2006.01) |
| *C07D 307/91* | (2006.01) |
| *C07D 333/76* | (2006.01) |
| *C07F 7/08* | (2006.01) |
| *C09K 11/06* | (2006.01) |
| *C07C 13/62* | (2006.01) |

(52) U.S. Cl.
CPC .......... *H01L 51/0074* (2013.01); *C07C 13/62* (2013.01); *C07D 209/82* (2013.01); *C07D 307/91* (2013.01); *C07D 333/76* (2013.01); *C07F 7/0816* (2013.01); *C09K 11/06* (2013.01); *H01L 51/0058* (2013.01); *H01L 51/0072* (2013.01); *H01L 51/0073* (2013.01); *H01L 51/5016* (2013.01); *H01L 51/5072* (2013.01); *C09K 2211/1011* (2013.01); *C09K 2211/1029* (2013.01); *C09K 2211/1088* (2013.01); *C09K 2211/1092* (2013.01); *C09K 2211/1096* (2013.01)

(58) Field of Classification Search
None
See application file for complete search history.

(56) References Cited

U.S. PATENT DOCUMENTS

| | | |
|---|---|---|
| 2010/0327266 A1 | 12/2010 | Kawamura |
| 2017/0186968 A1 | 6/2017 | Shiomi et al. |

OTHER PUBLICATIONS

Miura et. al., Rhodium-Catalyzed Dehydrogenative Coupling of Phenylheteroarenes with Alkynes or Alkenes; 2015, Journal of Org. Chem., 80, 2804-2814 (Year: 2015).*

* cited by examiner

*Primary Examiner* — Gregory D Clark

(57) ABSTRACT

An organic compound which can be used as the phosphorescent host material, the fluorescent host material, or the fluorescent dopant material of the light emitting layer, and/or the electron transporting material in the organic electroluminescence device is disclosed. The organic electroluminescence device employing the organic compound can lower driving voltage, prolong half-lifetime, and increase current efficiency.

10 Claims, 1 Drawing Sheet

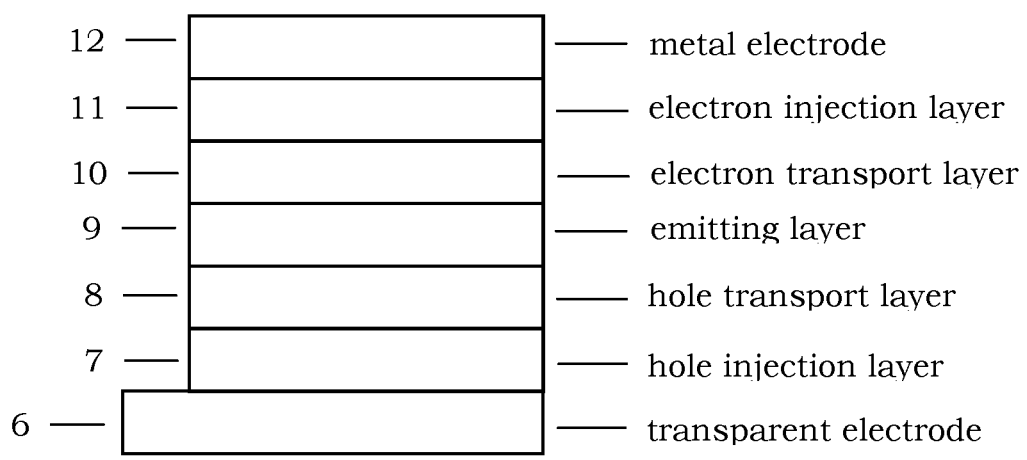

ORGANIC COMPOUND AND ORGANIC ELECTROLUMINESCENCE DEVICE USING THE SAME

FIELD OF INVENTION

The present invention relates to a novel organic compound and, more particularly, to an organic electroluminescence device using the organic compound.

BACKGROUND OF THE INVENTION

An organic electroluminescence (organic EL) device is an organic light-emitting diode (OLED) in which the light emitting layer is a film made from organic compounds, which emits light in response to the electric current. The light emitting layer containing the organic compound is sandwiched between two electrodes. The organic EL device is applied to flat panel displays due to its high illumination, low weight, ultra-thin profile, self-illumination without back light, low power consumption, wide viewing angle, high contrast, simple fabrication methods and rapid response time.

Typically, the organic EL device is composed of organic material layers sandwiched between two electrodes. The organic material layers include, e.g., hole injection layer (HIL), hole transporting layer (HTL), emitting layer (EML), electron transporting layer (ETL), and electron injection layer (EIL). The basic mechanism of organic EL involves the injection, transport, and recombination of carriers as well as exciton formation for emitting light. When an external voltage is applied across the organic EL device, electrons and holes are injected from the cathode and the anode, respectively. Electrons will be injected from the cathode into a LUMO (lowest unoccupied molecular orbital) and holes will be injected from the anode into a HOMO (highest occupied molecular orbital). Subsequently, the electrons recombine with holes in the light emitting layer to form excitons, which then deactivate to emit light. When luminescent molecules absorb energy to achieve an excited state, the exciton may either be in a singlet state or a triplet state, depending on how the spins of the electrons and holes have been combined. It is well known that the excitons formed under electrical excitation typically include 25% singlet excitons and 75% triplet excitons. In the fluorescence materials, however, the electrically generated energy in the 75% triplet excitons will be dissipated as heat for decay from the triplet state is spin forbidden. Therefore, a fluorescent electroluminescence device has only 25% internal quantum efficiency, which leads to the theoretically highest external quantum efficiency (EQE) of only 5% due to only ~20% of the light out-coupling efficiency of the device. In contrast to fluorescent electroluminescence devices, phosphorescent organic EL devices make use of spin-orbit interactions to facilitate intersystem crossing between singlet and triplet states, thus obtaining emission from both singlet and triplet states and the internal quantum efficiency of electroluminescence devices from 25% to 100%.

For full-colored flat panel displays using organic EL devices, the organic materials used in the organic EL devices are still unsatisfactory in half-life time, power consumption, luminance, and efficiency. In addition to those described above, the deep blue emission (CIE y coordinates below 0.15) from AMOLED also needs improvement.

SUMMARY OF THE INVENTION

Accordingly, an object of the invention is to provide a novel organic compound and an organic EL device using the same, which can exhibit higher luminance and current efficiency, longer half-life time, and improved deep blue emission.

Another object of the invention is to provide a novel organic compound and an organic EL device using the same, which can operate under reduced voltage and exhibit higher current efficiency and longer half-life time.

Still another object of the invention is to provide a novel organic compound and an organic EL device using the same, which can exhibit higher luminance and current efficiency and longer half-life time.

Yet another object of the present invention is to provide an organic compound, which can be used as a phosphorescent host material, a fluorescenct host material, or a fluorescenct dopant material in the emitting layer, and/or an electron transporting material in an organic EL device to improve the power consumption, luminance, current efficiency, device color, or life time.

According to the present invention, an organic compound which can be used in organic EL devices is disclosed. The organic compound is represented by the following formula (I):

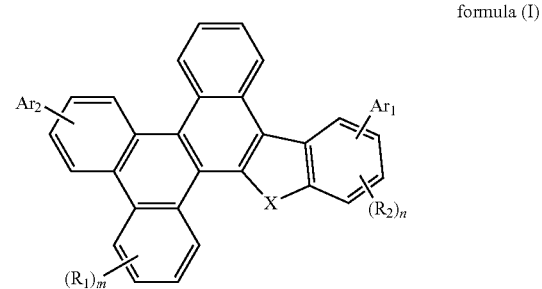

formula (I)

wherein m is an integer of 0 to 11; n is an integer of 0 to 3; X is O, S, $C(R_3)(R_4)$, $N(Ar_3)$, or $Si(R_5)(R_6)$; $Ar_1$, $Ar_2$, and $Ar_3$ are each independently a hydrogen atom, a halide, a substituted or unsubstituted arylamine group having 5 to 50 ring atoms, a substituted or unsubstituted heteroarylamine group having 5 to 50 ring atoms, a substituted or unsubstituted aryl group having 5 to 50 ring atoms, or a substituted or unsubstituted heteroaryl group having 5 to 50 ring atoms; and $R_1$ to $R_6$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

The present invention further discloses an organic electroluminescence device. The organic electroluminescence device comprises a pair of electrodes composed of a cathode and an anode, and a light emitting layer and one or more organic thin film layers between the pair of electrodes. At least one of the light emitting layer and the organic thin film layer comprises the organic compound of formula (I).

BRIEF DESCRIPTION OF THE DRAWINGS

The FIGURE shows one embodiment of the organic EL device of the present invention. In the device, hole injection layer 7 is deposited onto transparent electrode 6, hole transport layer 8 is deposited onto hole injection layer 7, fluorescence or phosphorescence emitting layer 9 is deposited onto hole transport layer 8, electron transport layer 10 is deposited onto emitting layer 9, electron injection layer 11 is deposited onto electron transport layer 10, and metal electrode 12 is deposited onto electron injection layer 11.

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In one embodiment of the present invention, an organic compound which can be used as the phosphorescent host material, the fluorescent host material, or the fluorescent dopant material of the light emitting layer, and/or the electron transporting material in the organic EL device is disclosed. The organic compound is represented by the following formula (I):

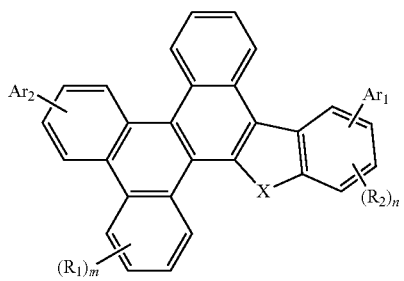

formula (I)

wherein m is an integer of 0 to 11; n is an integer of 0 to 3; X is O, S, C($R_3$)($R_4$), N($Ar_3$), or Si($R_5$)($R_6$); $Ar_1$, $Ar_2$, and $Ar_3$ are each independently a hydrogen atom, a halide, a substituted or unsubstituted arylamine group having 5 to 50 ring atoms, a substituted or unsubstituted heteroarylamine group having 5 to 50 ring atoms, a substituted or unsubstituted aryl group having 5 to 50 ring atoms, or a substituted or unsubstituted heteroaryl group having 5 to 50 ring atoms; and $R_1$ to $R_6$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

In some embodiments, $Ar_1$, $Ar_2$, and $Ar_3$ are independently selected from the group consisting of a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted arylamine group, a substituted or unsubstituted heteroarylamine group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted diphenylphosphine oxide group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group and a substituted or unsubstituted dihydrophenazine group.

In some embodiments, $Ar_1$, $Ar_2$, or $Ar_3$ represents one of the following substituents:

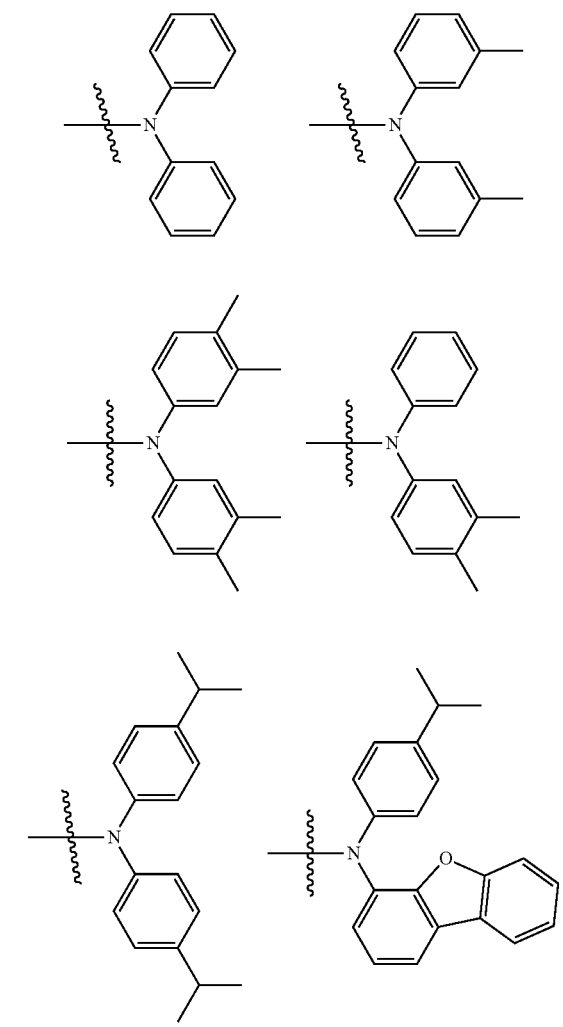

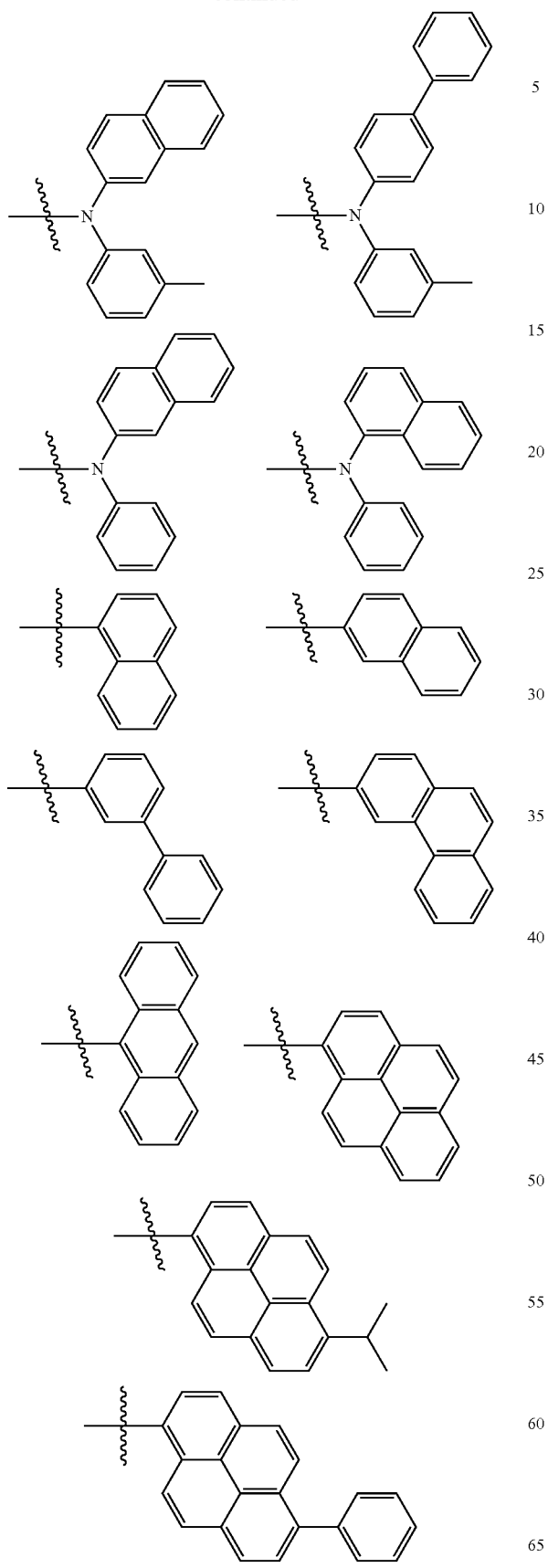
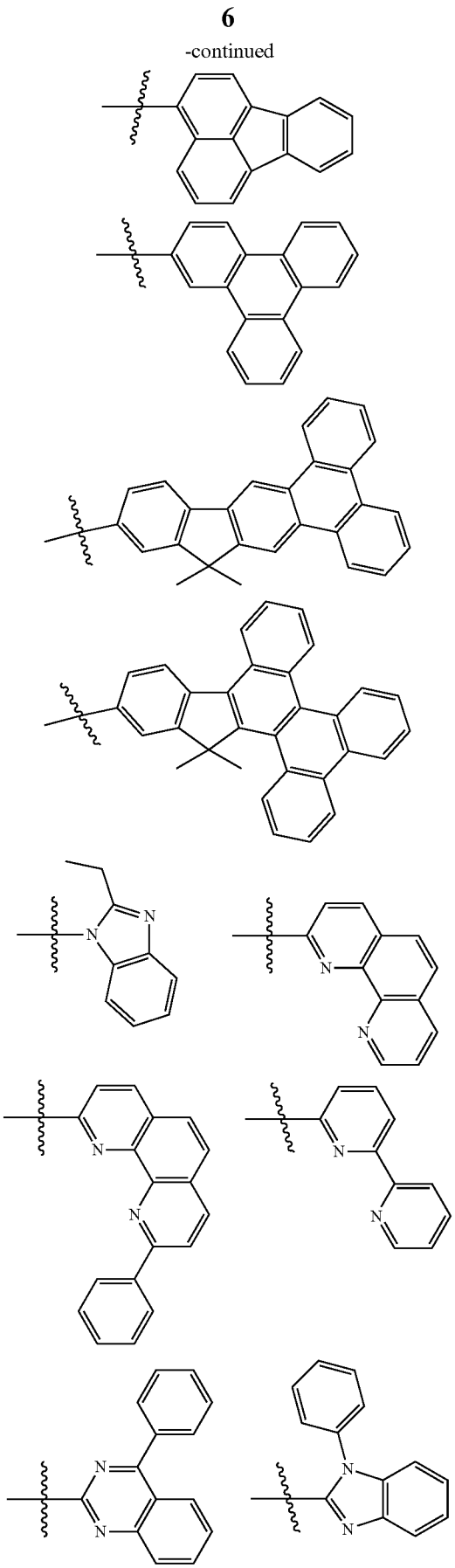

-continued
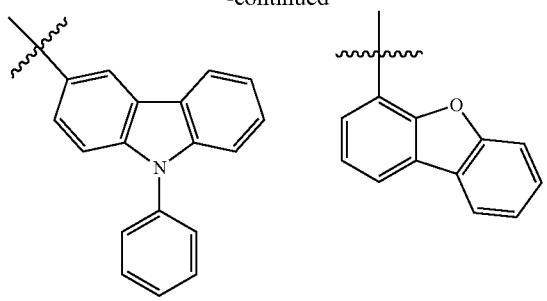
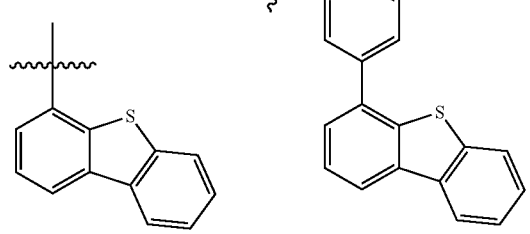
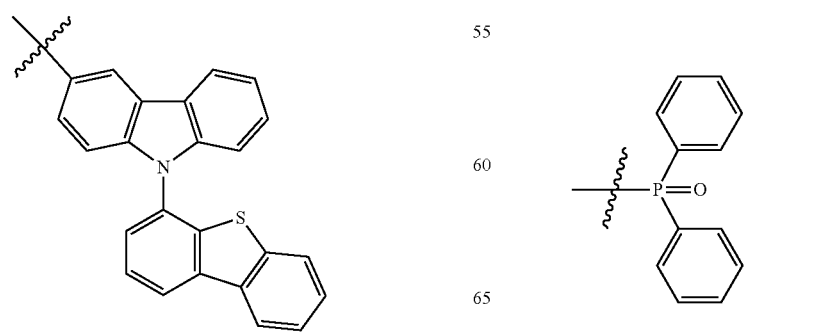
-continued
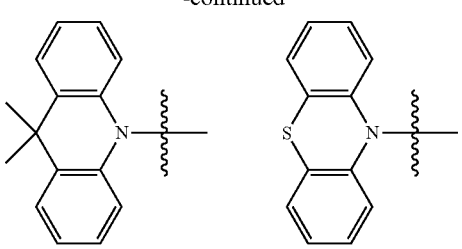
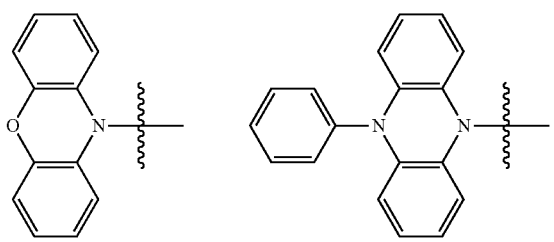
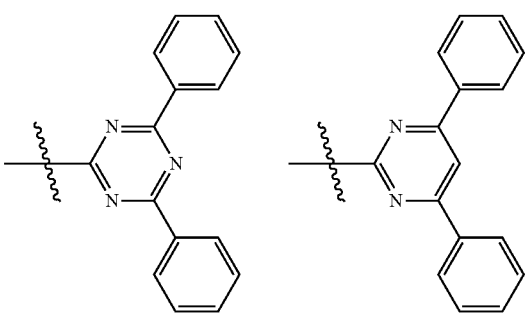
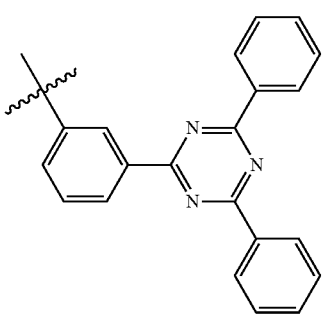

Preferably, the organic compound is one of the following compounds:
C1
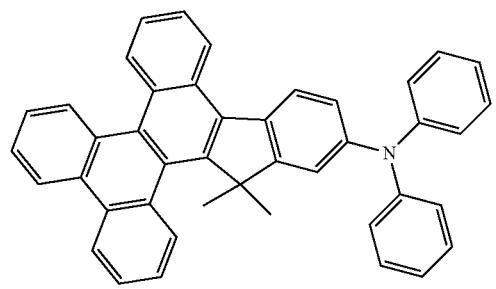
C2
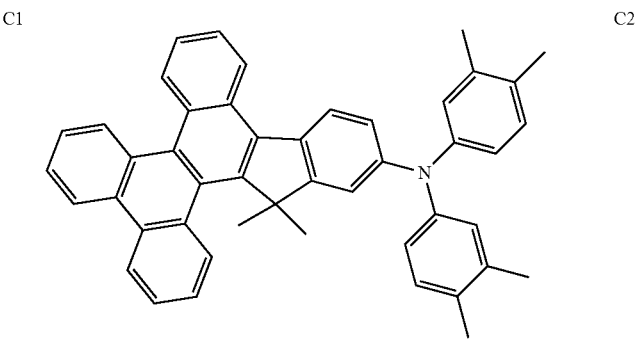
C3
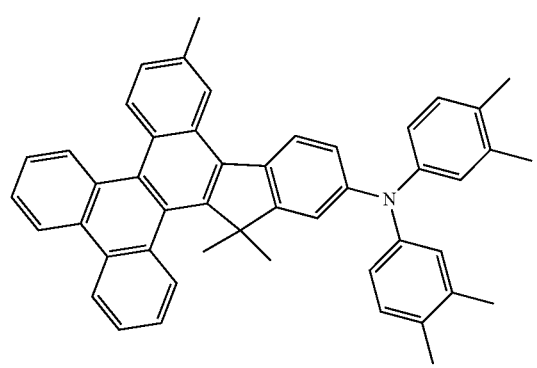
C4
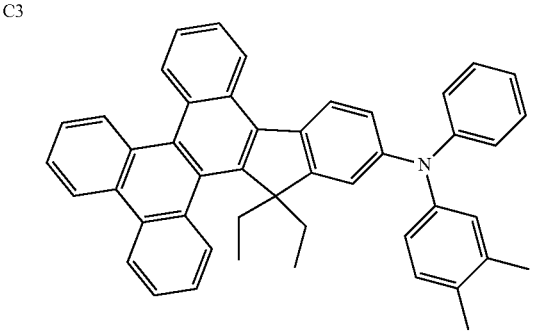
C5
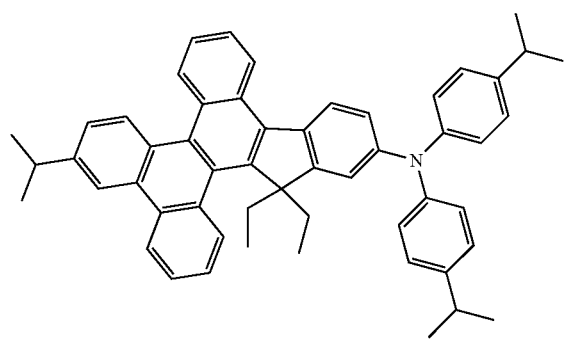
C6
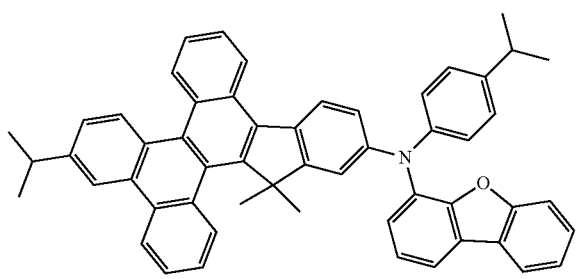
C7
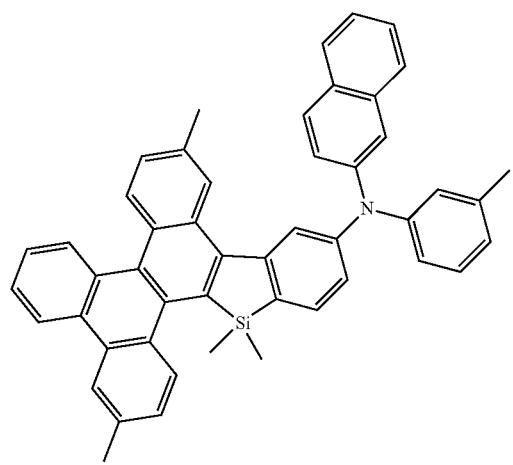
C8
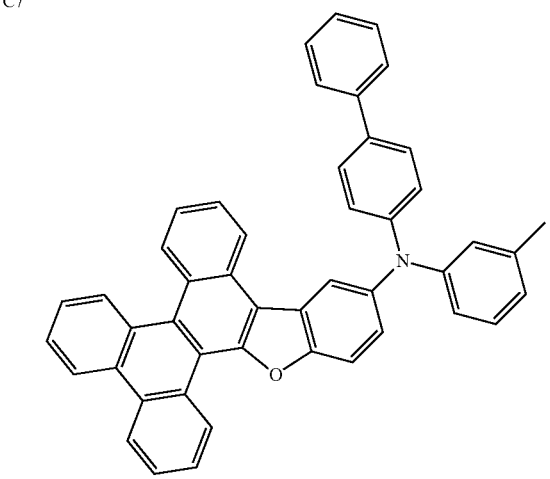

-continued
C9
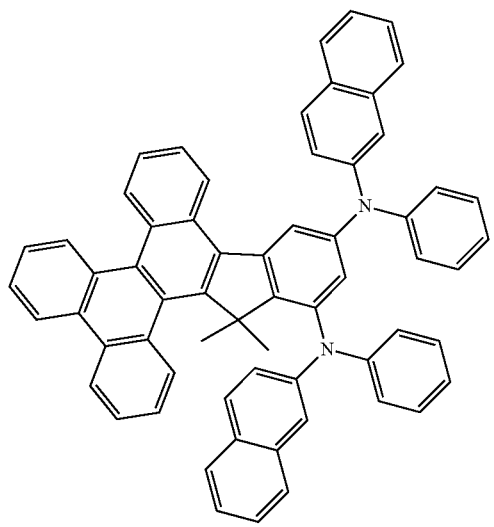
C10
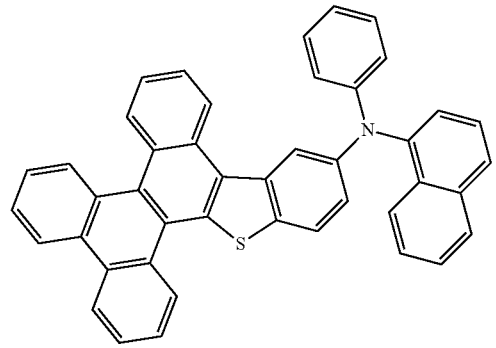
C11
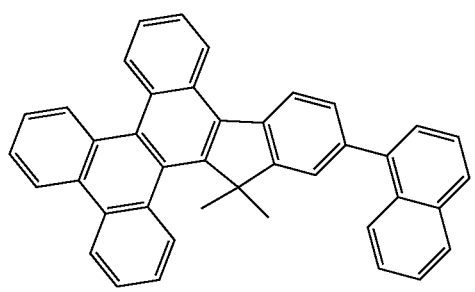
C12
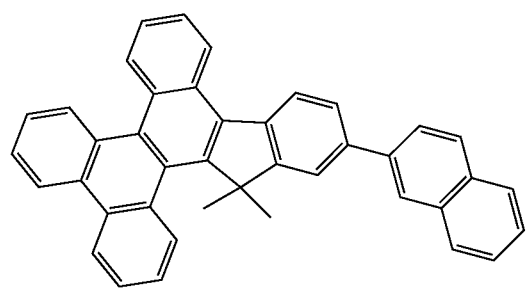
C13
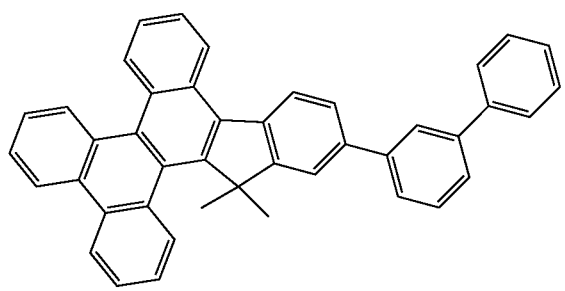
C14
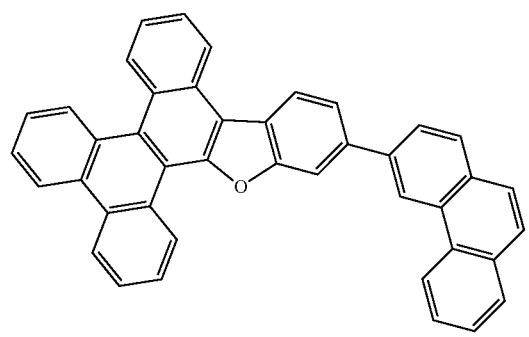
C15
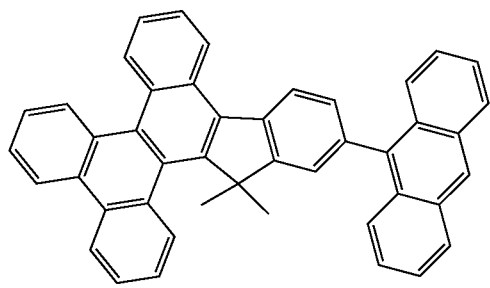
C16
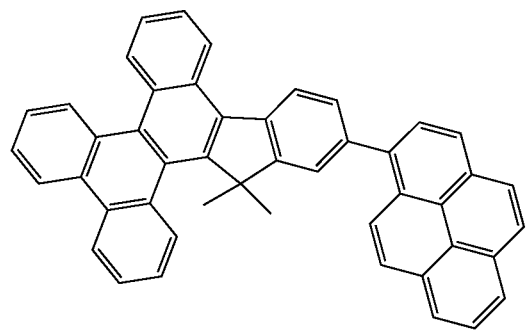

-continued
C17
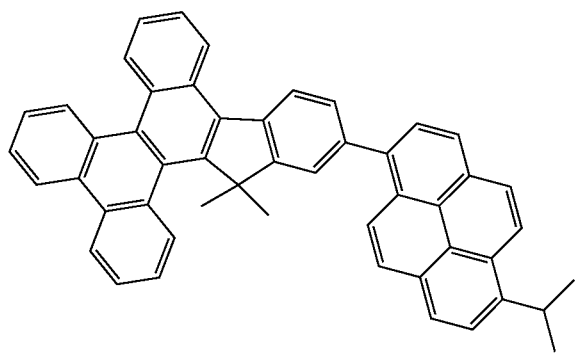
C18
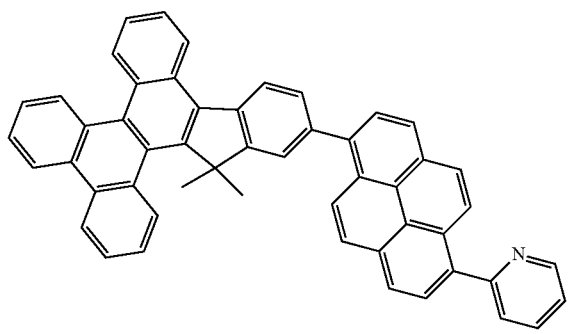
C19
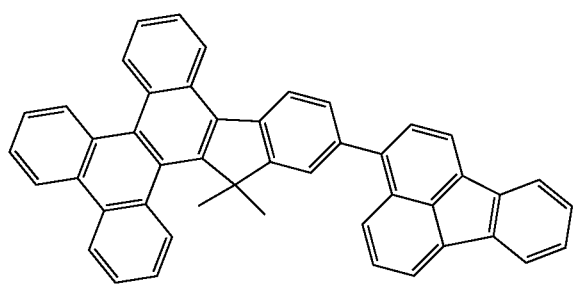
C20
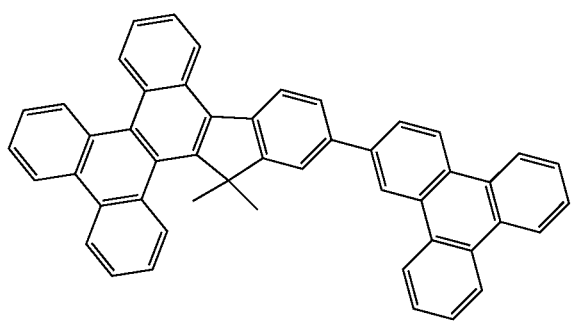
C21
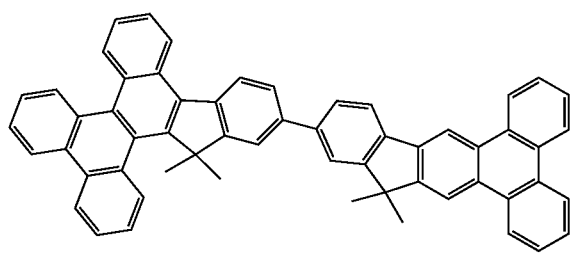
C22
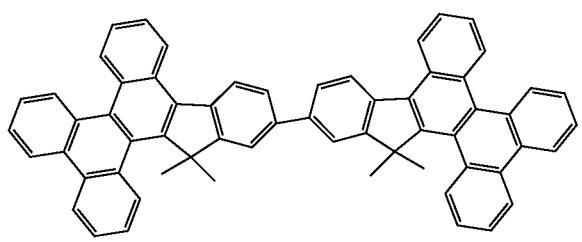
C23
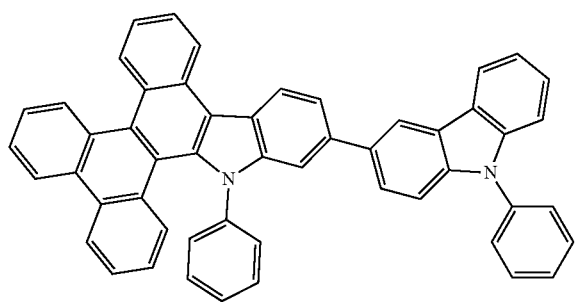
C24
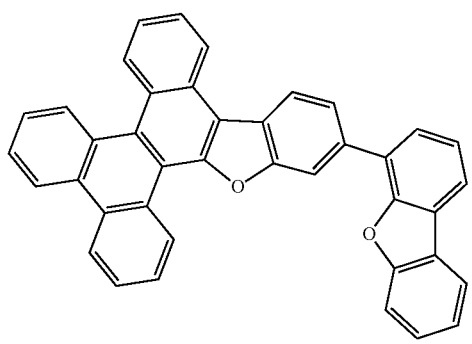

-continued
C25
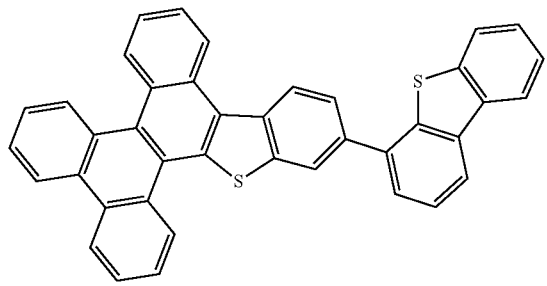
C26
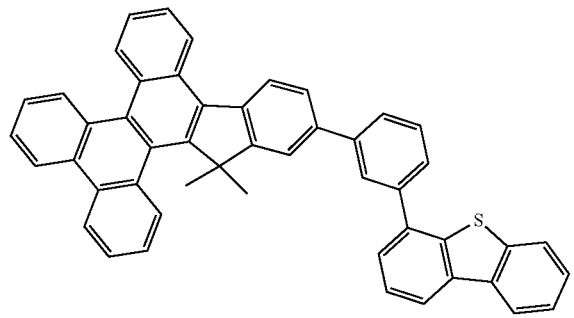
C27
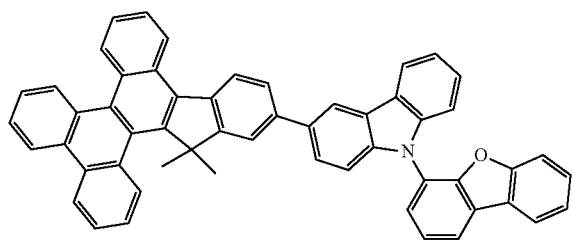
C28
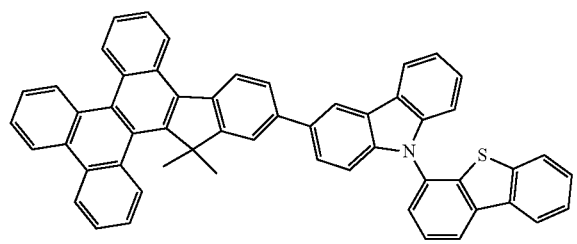
C29
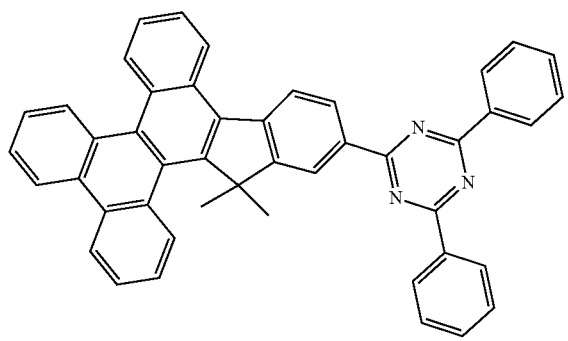
C30
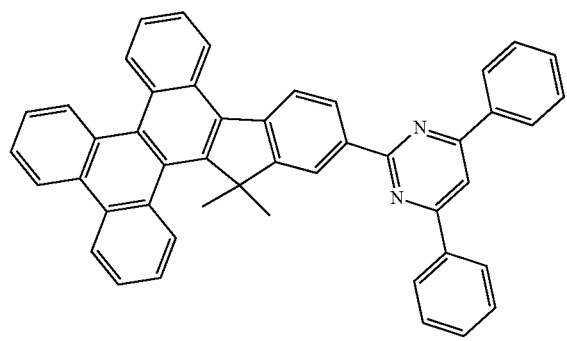
C31
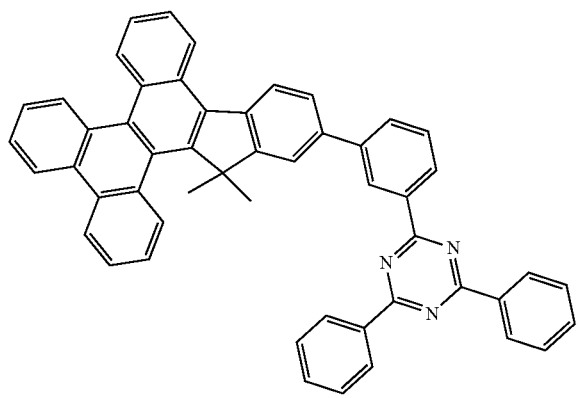
C32
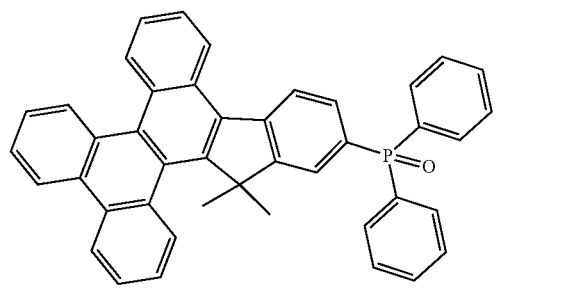

-continued
C33
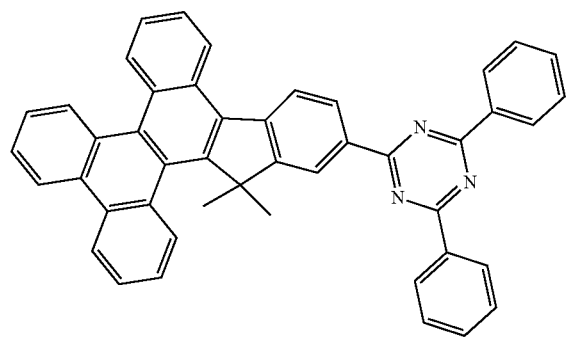
C34
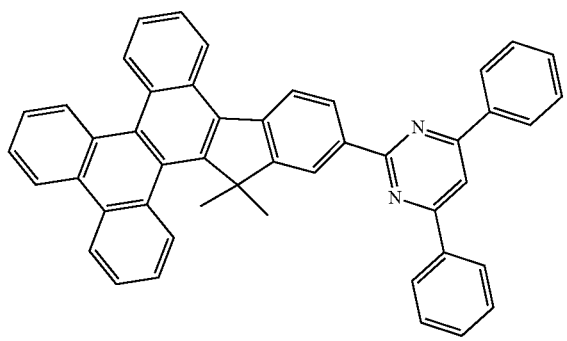
C35
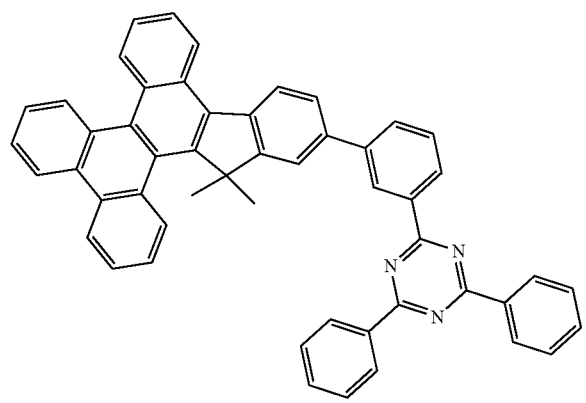
C36
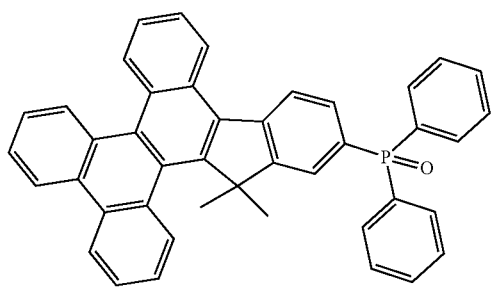
C37
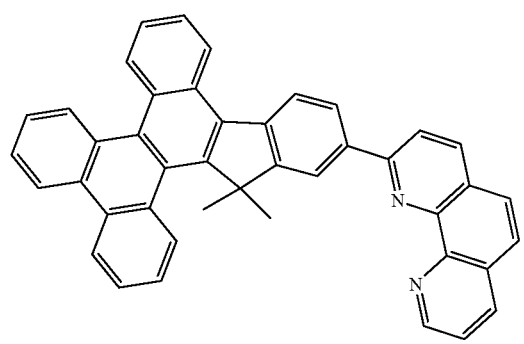
C38
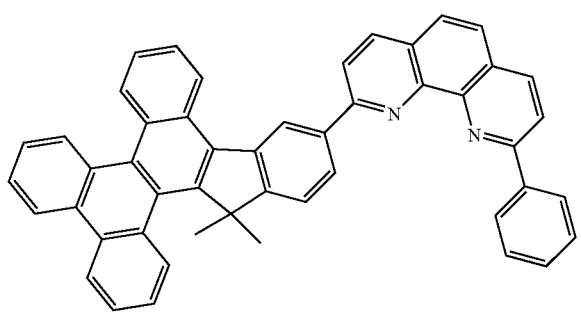
C39
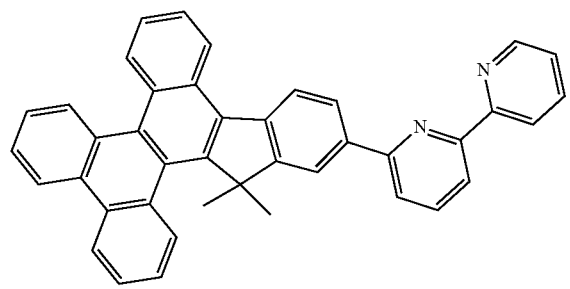
C40
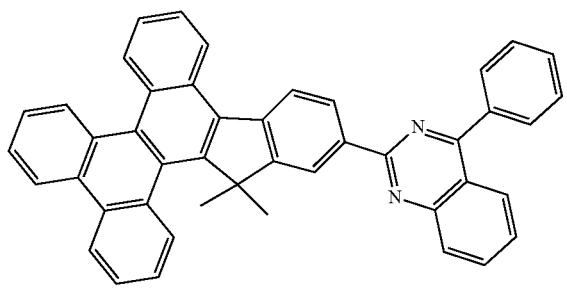

-continued
C41
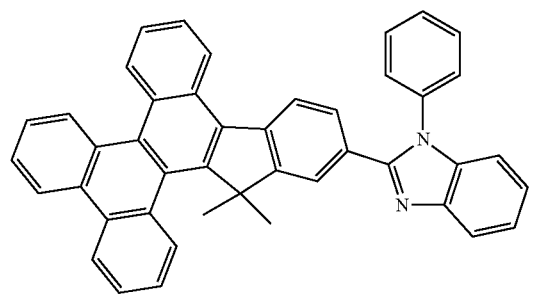
C42
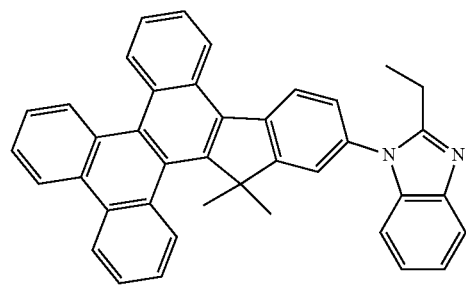
C43
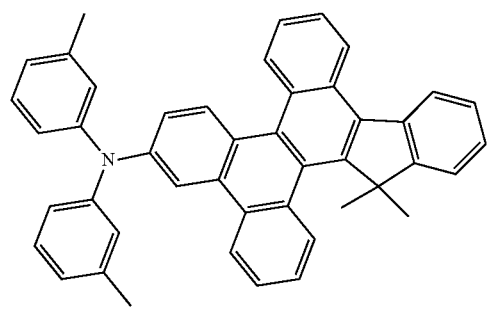
C44
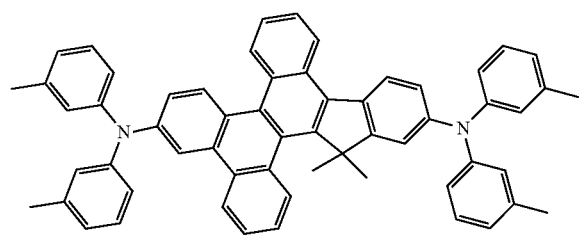
C45
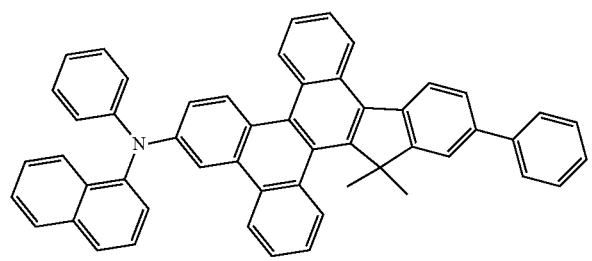
C46
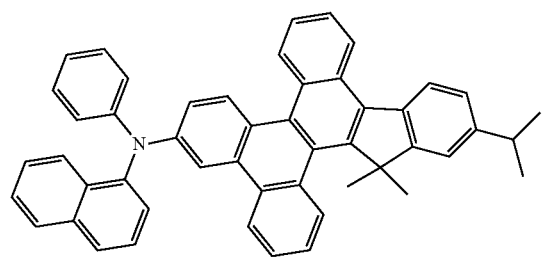
C47
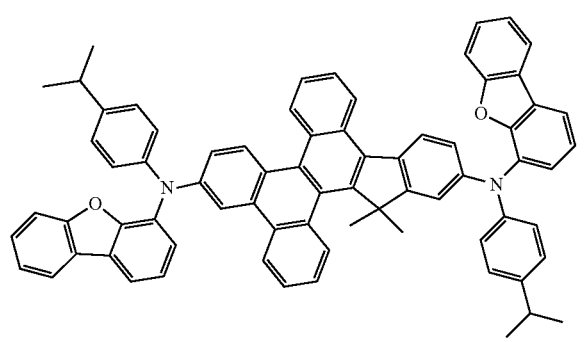
C48
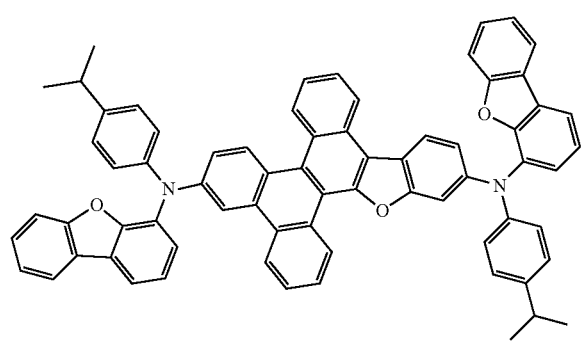
C49
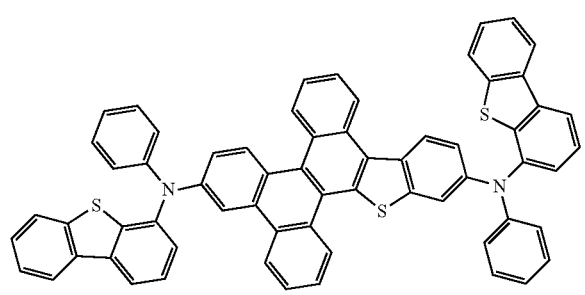
C50
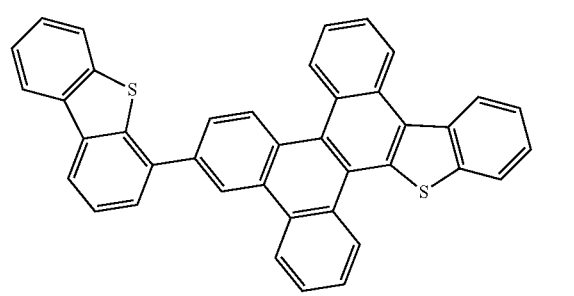

-continued
C51
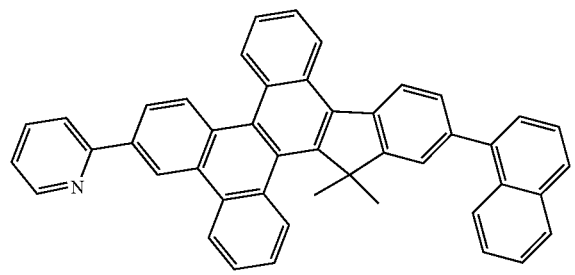
C52
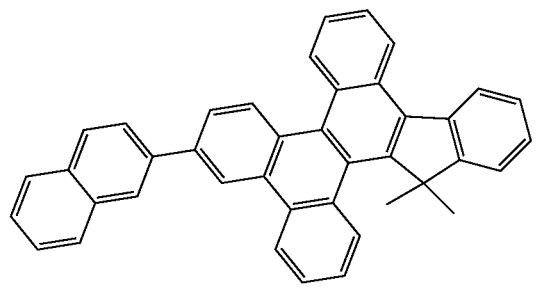
C53
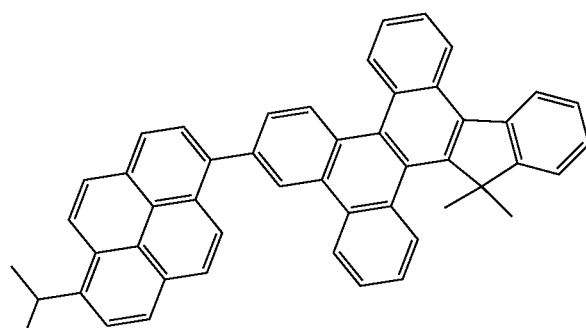
C54
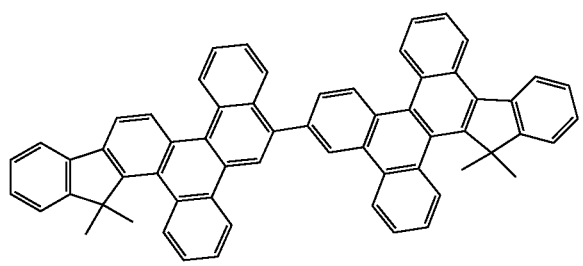
C55
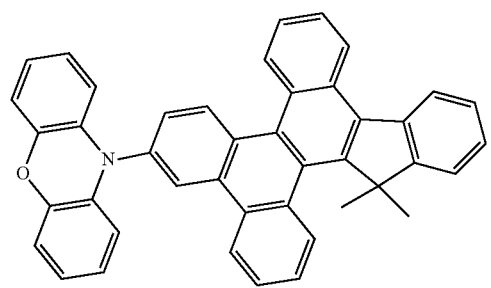
C56
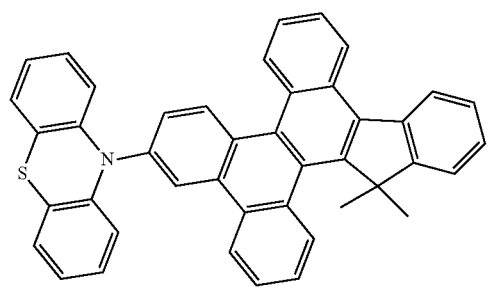
C57
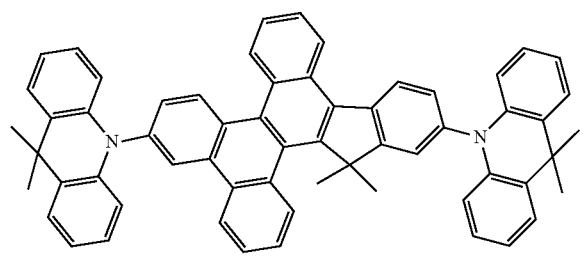
C58
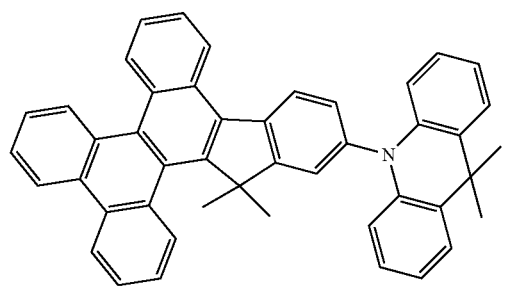
C59
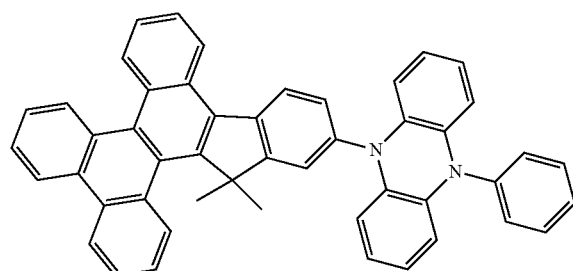
C60
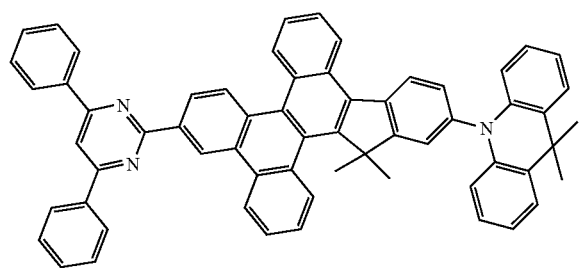

-continued
C61
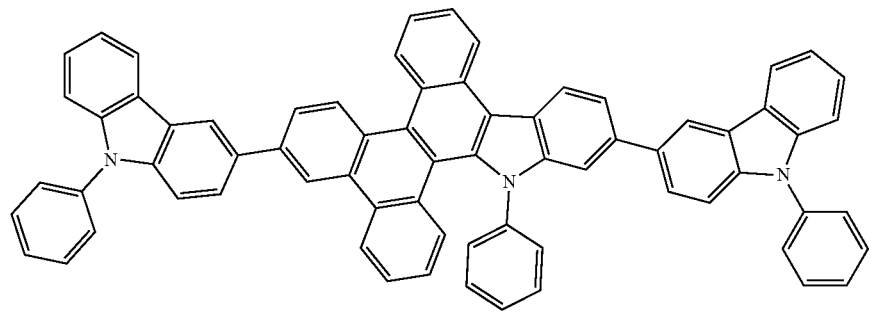
C62
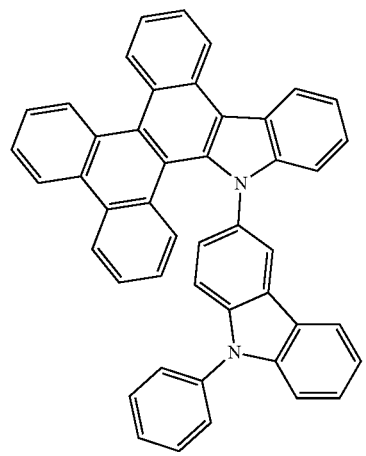
C63
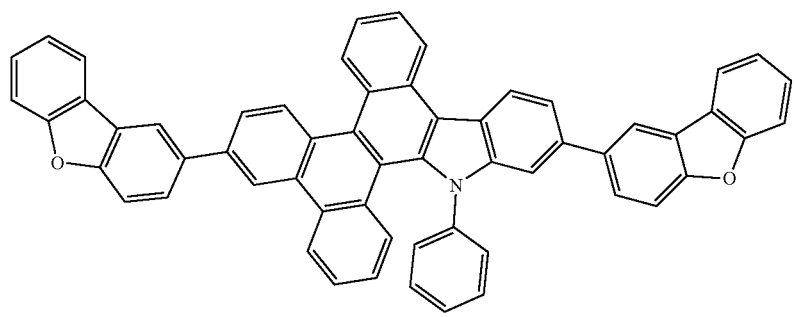
C64
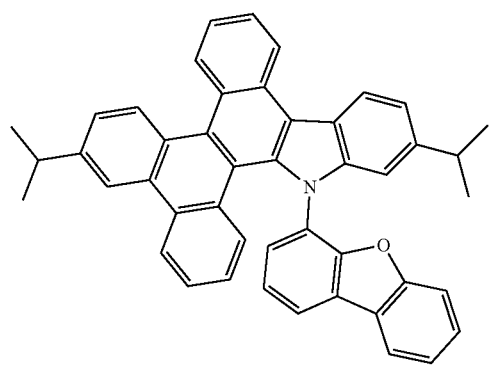
C65
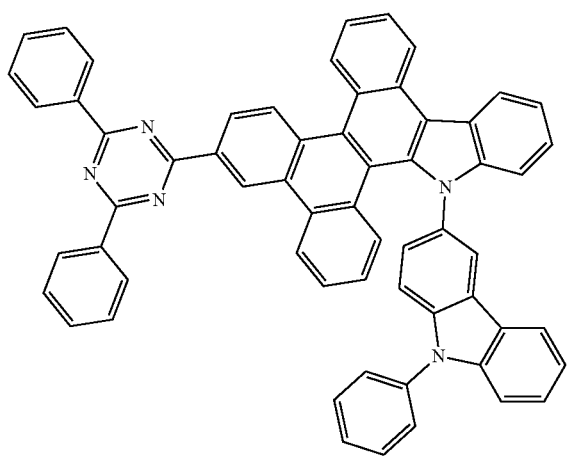

-continued
C66
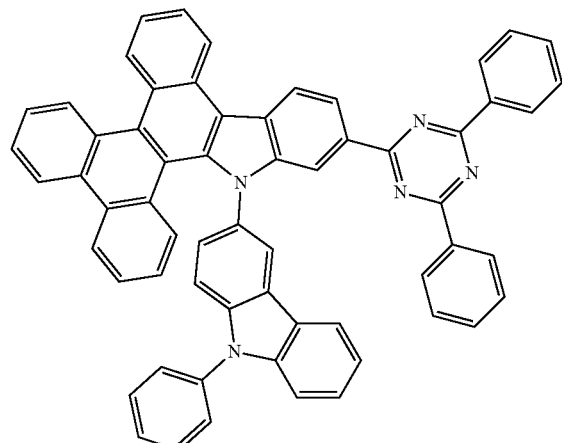
C67
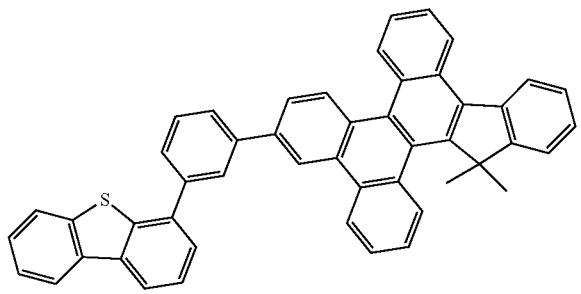
C68
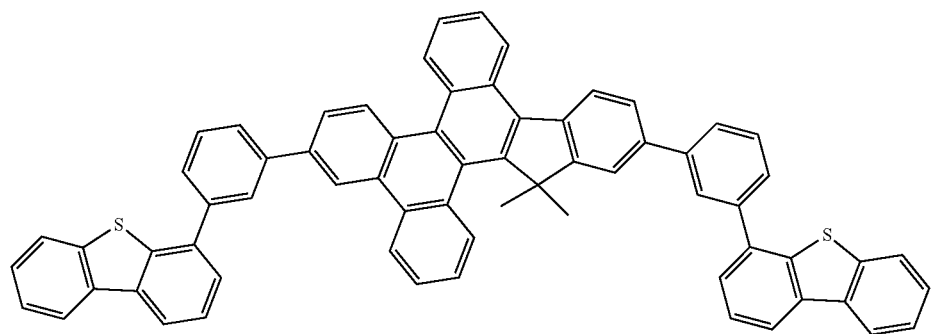
C69
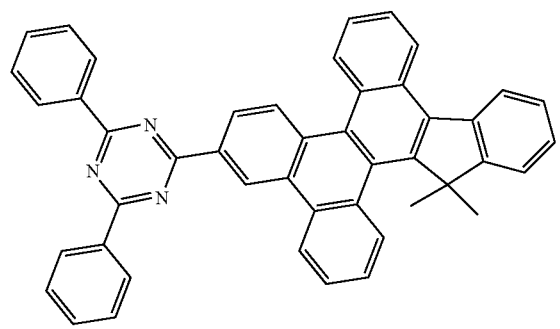
C70
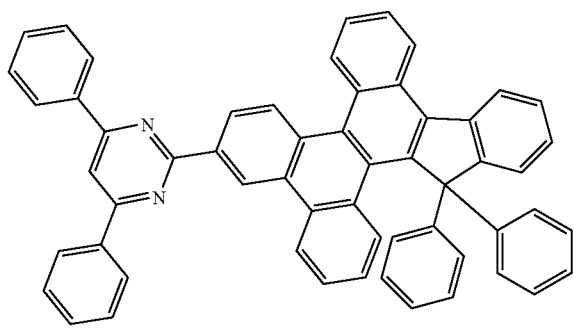
C71
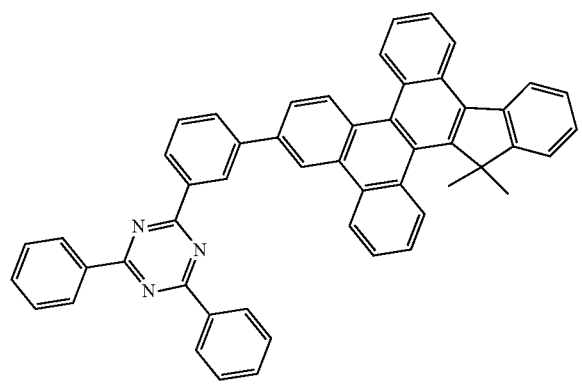
C72
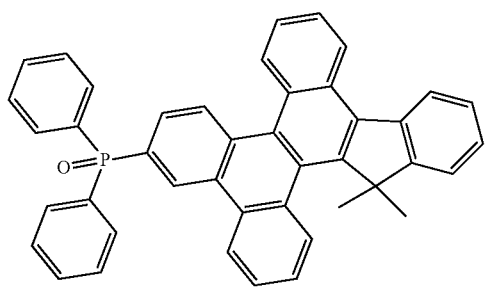

-continued
C73
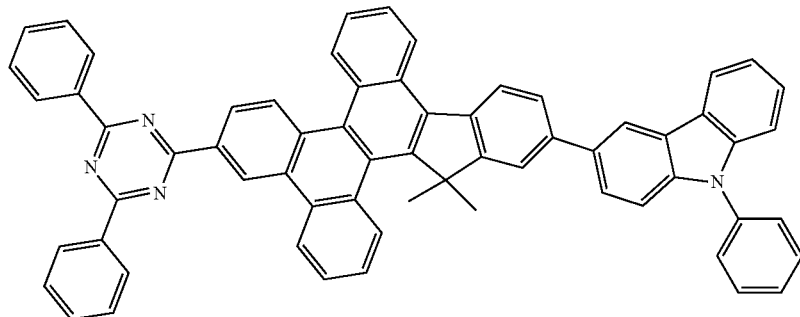
C74
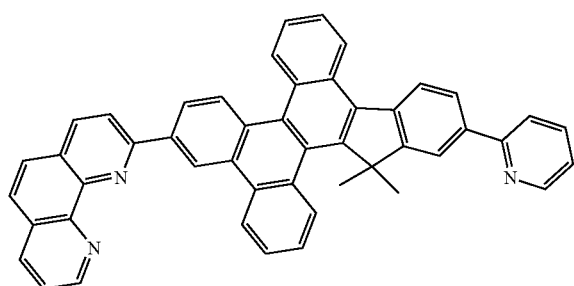
C75
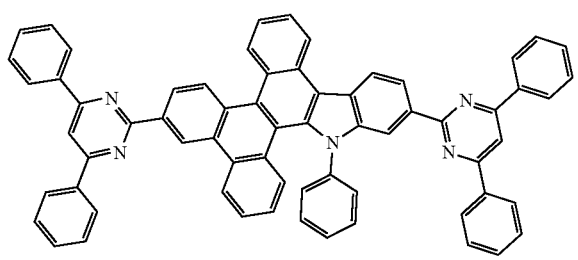
C76
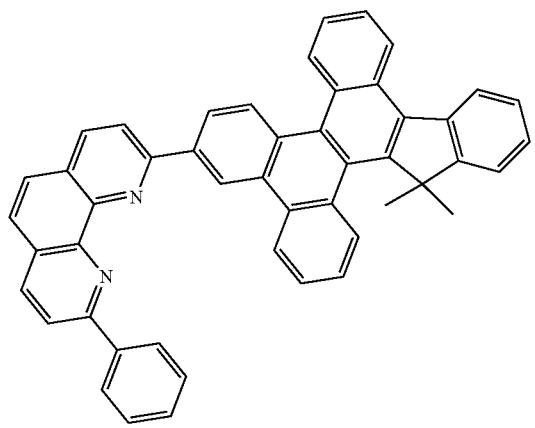
C77
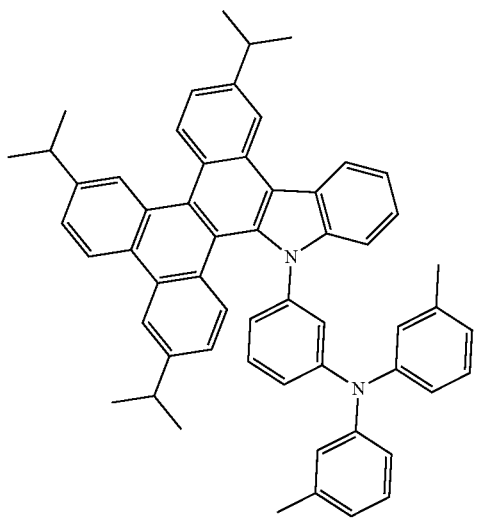
C78
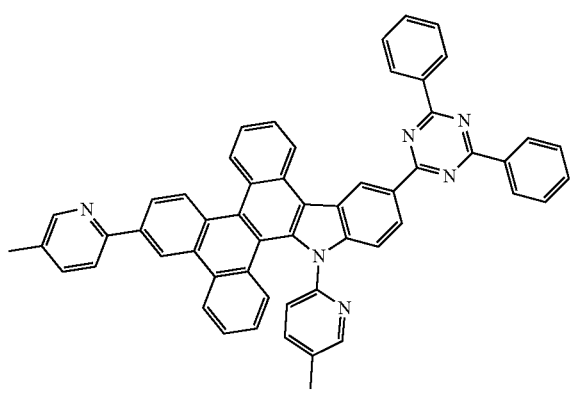
C79
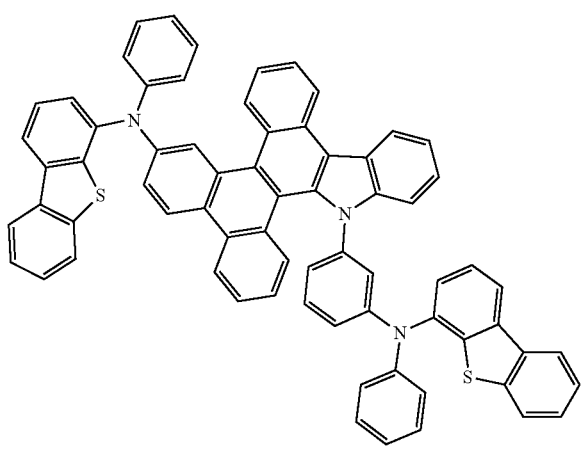

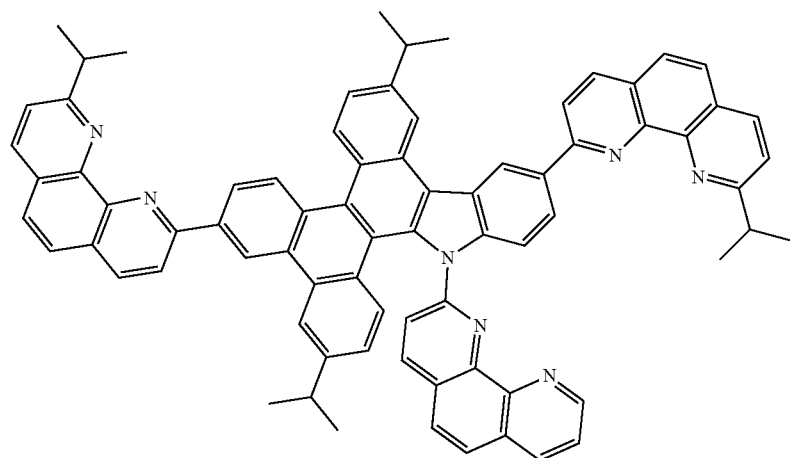
C80
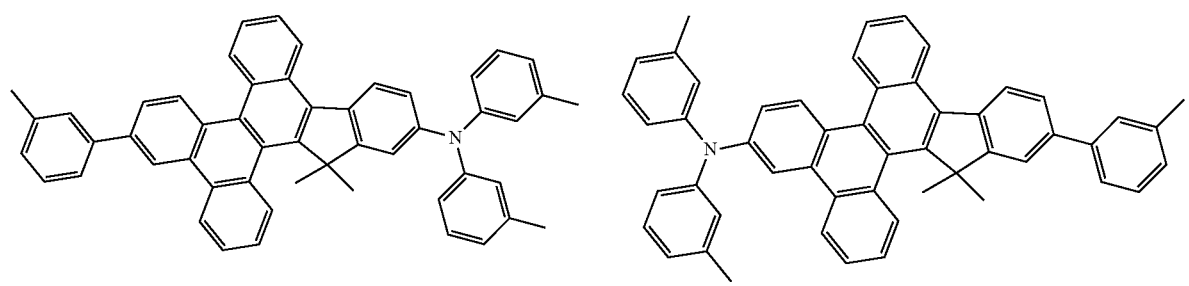
C81　　　　C82
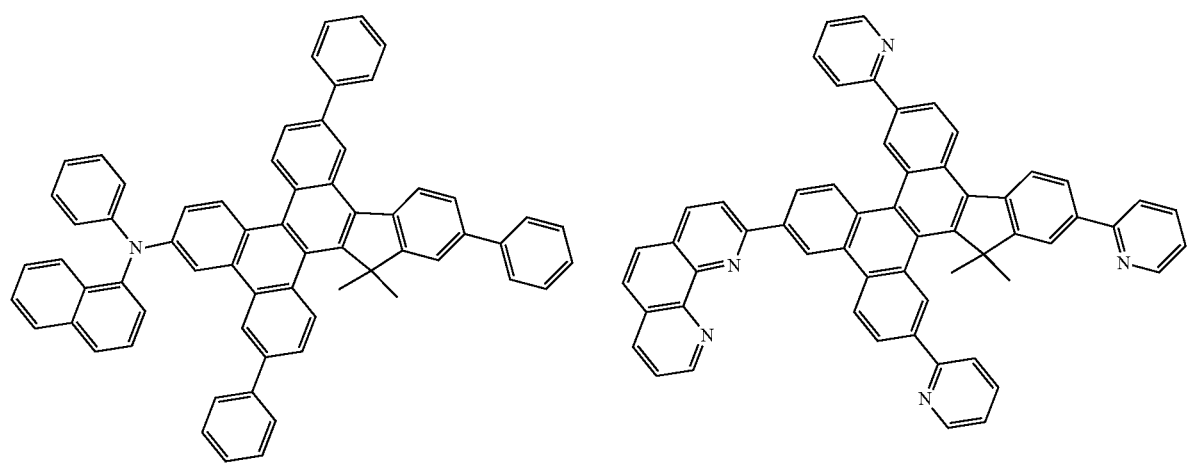
C83　　　　C84

-continued

C85
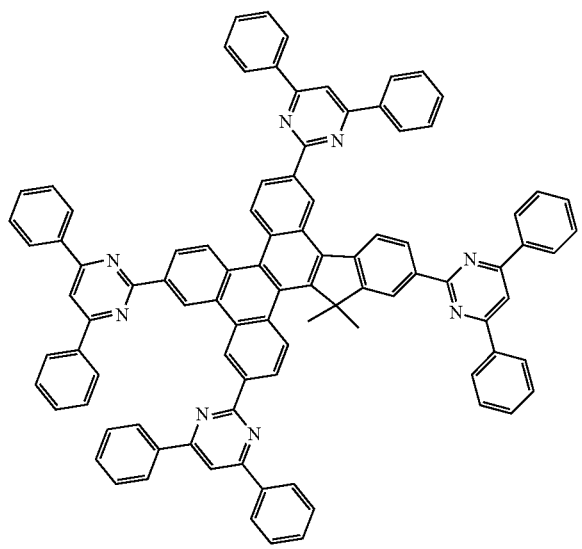

C86
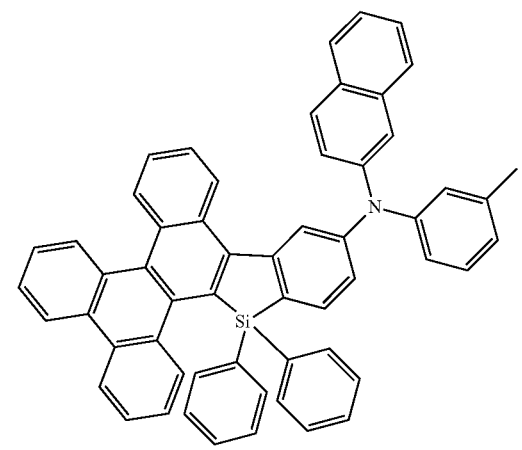

C87
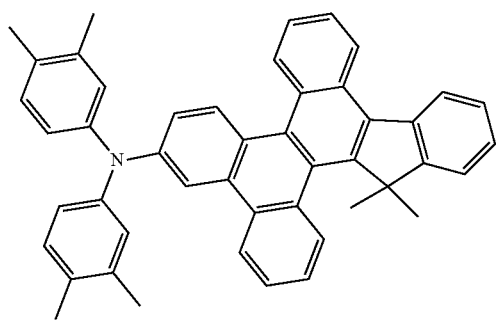

C88
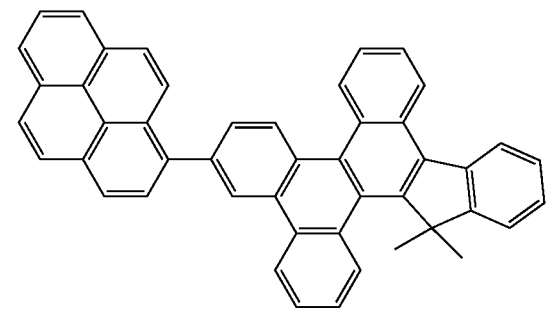

C89
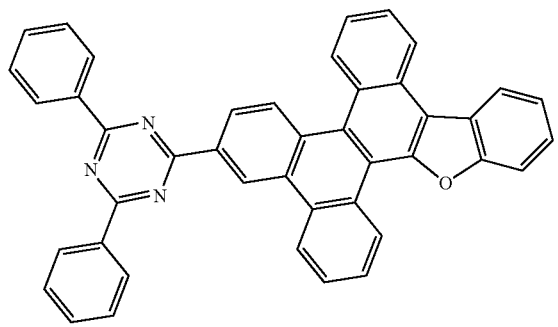

C90
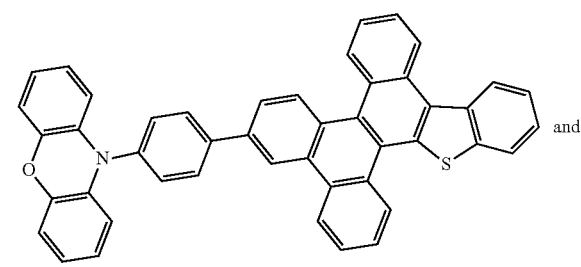

and

C91
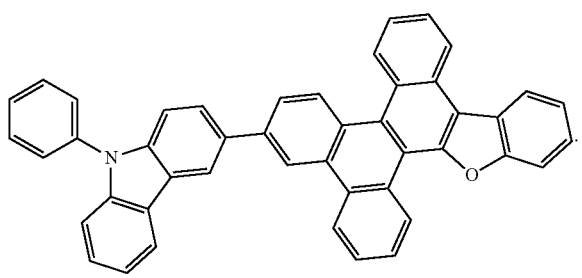

.

In another embodiment of the present invention, an organic electroluminescence device is disclosed. The organic electroluminescence device comprises a pair of electrodes composed of a cathode and an anode, and a light emitting layer and one or more organic thin film layers between the pair of electrodes. At least one of the light emitting layer and the organic thin film layer comprises the organic compound of formula (I).

In some embodiments, the light emitting layer comprising the organic compound of formula (I) is a host material. The host material may be a phosphorescent host material or a fluorescent host material. In certain embodiments, the light emitting layer comprising the organic compound of formula (I) is used as a fluorescent dopant material.

In some embodiments, the organic thin film layer comprising the organic compound of formula (I) is an electron transporting layer.

In a further embodiment of the present invention, the organic electroluminescence device is a lighting panel. In other embodiment of the present invention, the organic electroluminescence device is a backlight panel.

Detailed preparation of the organic compounds of the present invention will be clarified by exemplary embodiments below, but the present invention is not limited thereto. EXAMPLES 1 to 10 show the preparation of the organic compounds of the present invention, and EXAMPLES 11 to 13 show the fabrication and test reports of the organic EL devices.

Example 1

Synthesis of Intermediate A

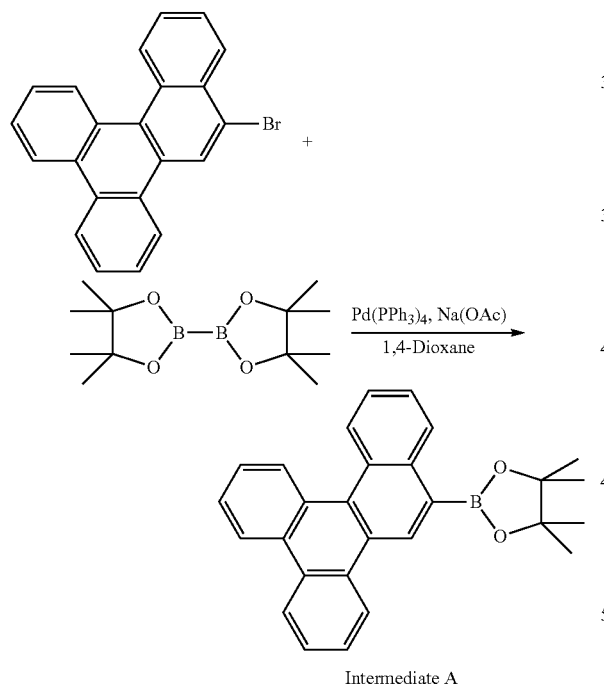

Intermediate A

A mixture of 3 g (8.4 mmol) of 10-bromobenzo[g]chrysene (synthesis reference: US 20100327266), 2.5 g (10.1 mmol) of 4,4,4',4',5,5,5',5'-octamethyl-2,2'-bi(1,3,2-dioxaborolane), 0.12 g (0.1 mmol) of Pd(PPh$_3$)$_4$, 1.0 g (12.6 mmol) of sodium acetate, and 60 ml of 1,4-dioxane was degassed and placed under nitrogen, and then heated at 100° C. for 6 hrs. After the reaction finished, the mixture was allowed to cool to room temperature. Subsequently, the organic layer was extracted with ethyl acetate and water, and then dried with anhydrous magnesium sulfate. After the solvent was removed, the residue was purified by column chromatography on silica to give Intermediate A (2.8 g, 85%).

Synthesis of Intermediate B

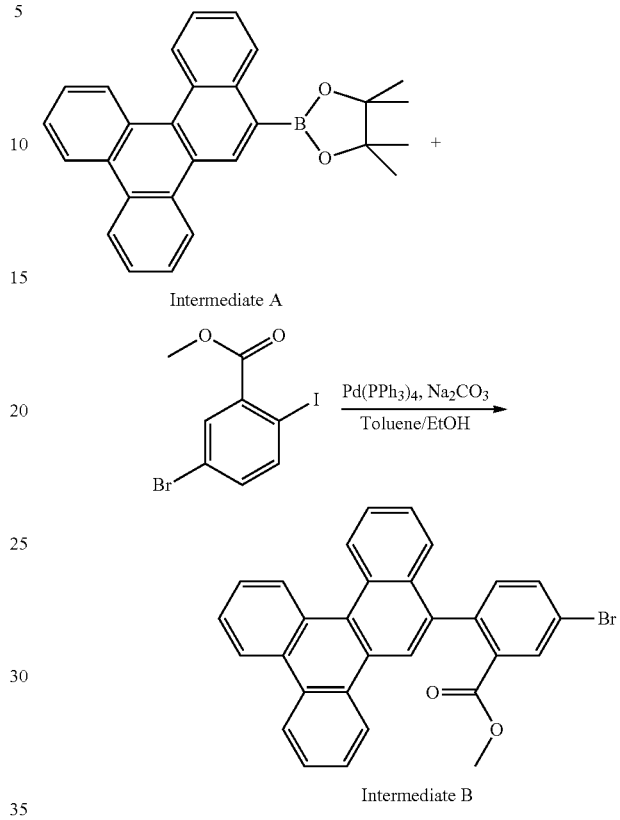

Intermediate B

A mixture of 2 g (5.0 mmol) of Intermediate A, 1.7 g (5.0 mmol) of methyl 5-bromo-2-iodobenzoate, 0.06 g (0.05 mmol) of Pd(PPh$_3$)$_4$, 10 ml of 2M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, the organic layer was extracted with dichloromethane and water, and then dried with anhydrous MgSO$_4$. After the solvent was removed, the residue was purified by column chromatography on silica to give Intermediate B (1.7 g, 68%).

Synthesis of Intermediate C

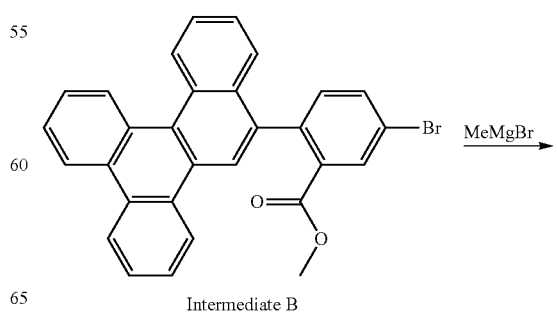

Intermediate B

-continued

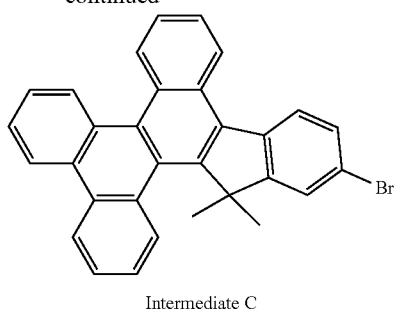

Intermediate C

-continued

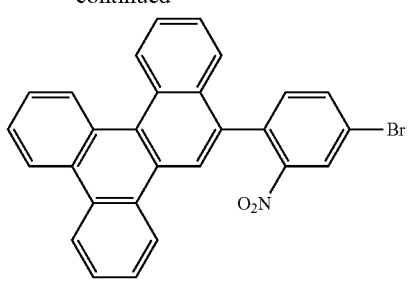

Intermediate D

Under the nitrogen gas, while 1.5 g (3.1 mmol) of Intermediate B was stirred in dry THF, methyl magnesium bromide (6 equivalent) was slowly added dropwise thereto. The mixture was stirred for 16 hrs at room temperature. After completion of the reaction, a little distilled water was slowly added, and then the mixture was extracted with ethyl acetate and washed with water sequentially. The organic layer was then dried with anhydrous MgSO$_4$ to remove the solvent for obtaining a residue. Subsequently, excess phosphoric acid solvent (~10 ml) was added to the residue, which was then stirred at room temperature for more than 16 hrs. Afterwards, distilled water (~50 ml) was slowly added and then stirred for 1 hour. After the precipitated solids were filtered, the filtered solids were extracted with dichloromethane solvent and then washed with sodium hydroxide aqueous solution. Subsequently, the dichloromethane solvent layer was taken out and then the moisture was removed by using magnesium sulfate. Finally, the residual solvent was removed to obtain the Intermediate C (0.5 g, 34%). MS (m/z, FAB+): 474.1.

Synthesis of Intermediate D

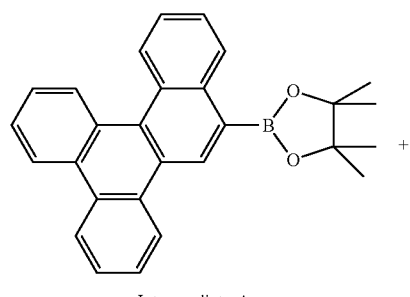

Intermediate A

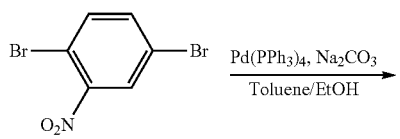

A mixture of 2 g (5.0 mmol) of Intermediate A, 1.4 g (5.0 mmol) of 2,5-dibromonitrobenzene, 0.06 g (0.05 mmol) of Pd(PPh$_3$)$_4$, 10 ml of 2M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, the organic layer was extracted with dichloromethane and water, and then dried with anhydrous MgSO$_4$. After the solvent was removed, the residue was purified by column chromatography on silica to give Intermediate D (0.8 g, 35%).

Synthesis of Intermediate E

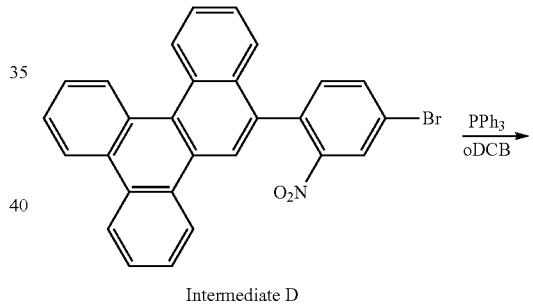

Intermediate D

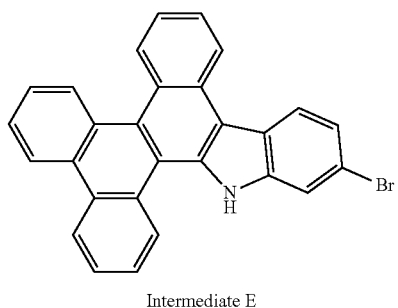

Intermediate E

A mixture of 1 g (2.1 mmol) of Intermediate D, 5.5 g (21.0 mmol) of Triphenylphosphine, and 30 ml of oDCB was placed under nitrogen gas, and then heated at 180° C. for 8 hrs. After the reaction finished, the mixture was allowed to cool to room temperature. The mixture was poured into water, and then filtered to give Intermediate E (0.5 g, 50%).

Synthesis of Intermediate F

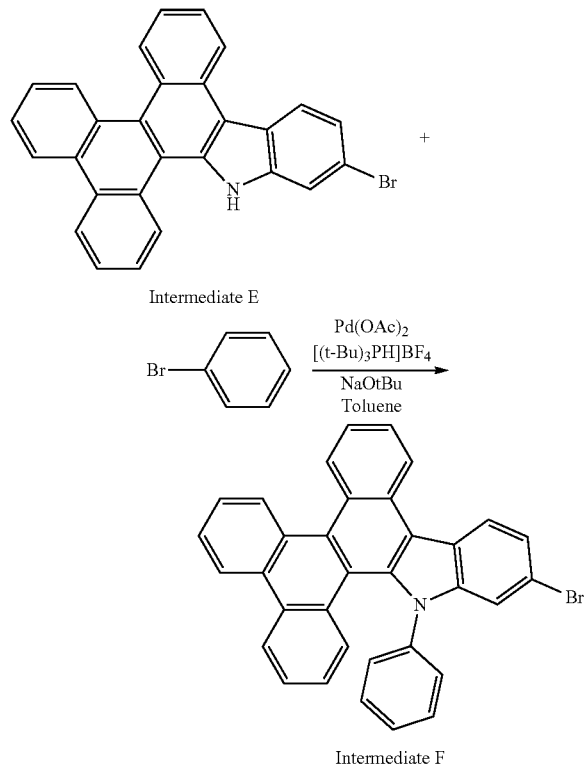

Intermediate E

Intermediate F

A mixture of 2.0 g (4.5 mmol) of Intermediate E, 1.1 g (6.7 mmol) of bromobenzene, 0.05 g (0.2 mmol) of Pd(OAc)$_2$, 0.1 g (0.4 mmol) of tri-tert-butylphosphonium tetrafluoroborate, 0.9 g (9.0 mmol) of sodium tert-butoxide, and 50 ml of toluene was degassed and placed under nitrogen gas, and then heated at 120° C. for 16 hrs. After the reaction finished, the mixture was allowed to cool to room temperature. Subsequently, the organic layer was extracted with dichloromethane and water, and then dried with anhydrous MgSO$_4$. After the solvent was removed, the residue was purified by column chromatography on silica to give Intermediate F (1.3 g, 55%). MS (m/z, FAB+): 523.5.

Synthesis of Intermediate G

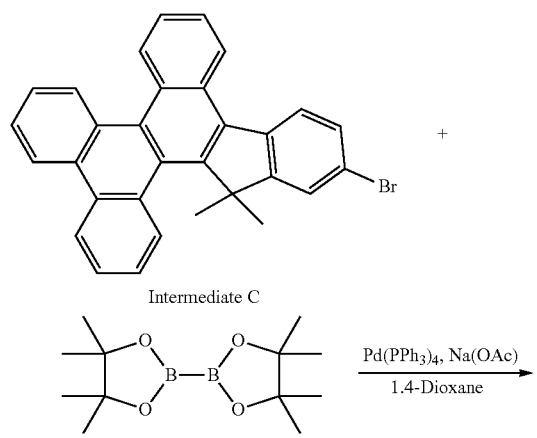

Intermediate C

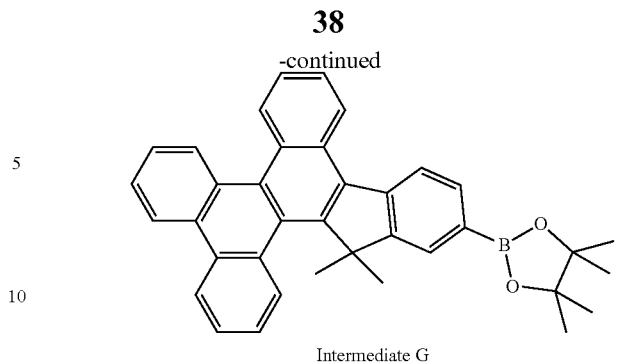

Intermediate G

A mixture of 2 g (4.2 mmol) of Intermediate C, 1.4 g (5.5 mmol) of 4,4,4',4',5,5,5',5'-octamethyl-2,2'-bi(1,3,2-dioxaborolane), 0.24 g (0.2 mmol) of Pd(PPh$_3$)$_4$, 0.8 g (8.4 mmol) of sodium acetate, and 60 ml of 1,4-dioxane was degassed and placed under nitrogen, and then heated at 100° C. for 6 hrs. After the reaction finished, the mixture was allowed to cool to room temperature. Subsequently, the organic layer was extracted with ethyl acetate and water, and then dried with anhydrous magnesium sulfate. After the solvent was removed, the residue was purified by column chromatography on silica to give Intermediate G (1.7 g, 80%).

Synthesis of Compound C2

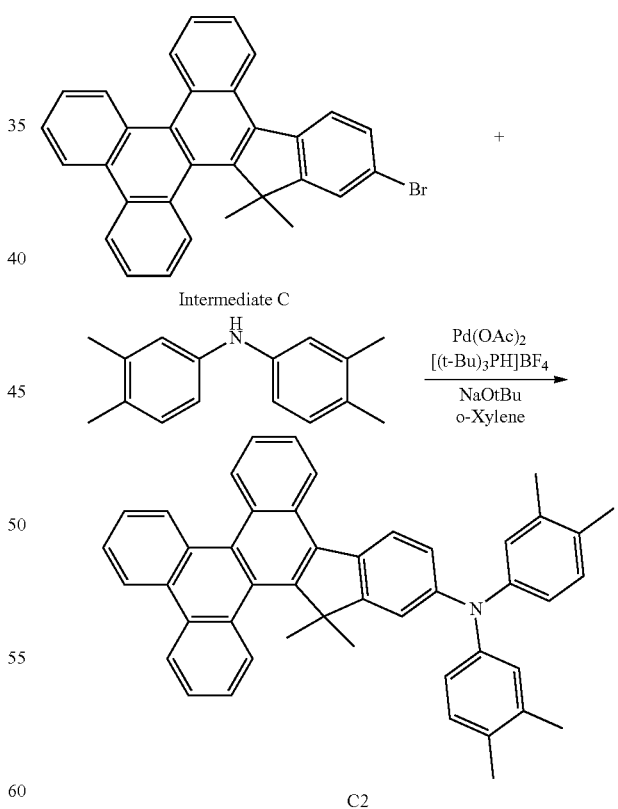

A mixture of 2.0 g (4.2 mmol) of Intermediate C, 1.2 g (5.5 mmol) of bis(3,4-dimethylphenyl)amine, 0.05 g (0.2 mmol) of Pd(OAc)$_2$, 0.1 g (0.4 mmol) of tri-tert-butylphosphonium tetrafluoroborate, 0.9 g (9.0 mmol) of sodium tert-butoxide, and 60 ml of o-xylene was degassed and placed under nitrogen gas, and then heated at 150° C. for 8 hrs. After the reaction finished, the mixture was allowed to cool to room temperature. Subsequently, the organic layer was extracted with dichloromethane and water, and then dried with anhydrous MgSO$_4$. After the solvent was removed, the residue was purified by column chromatography on silica to give compound C2 (1.9 g, 75%). MS (m/z, FAB+): 618.5.

Example 2

Synthesis of Compound C15

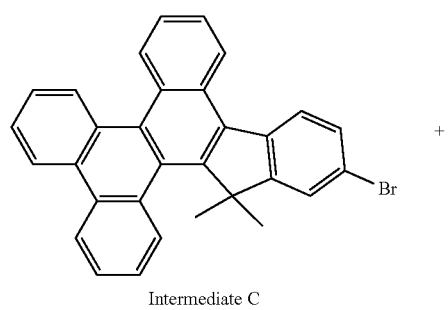

Example 3

Synthesis of Compound C29

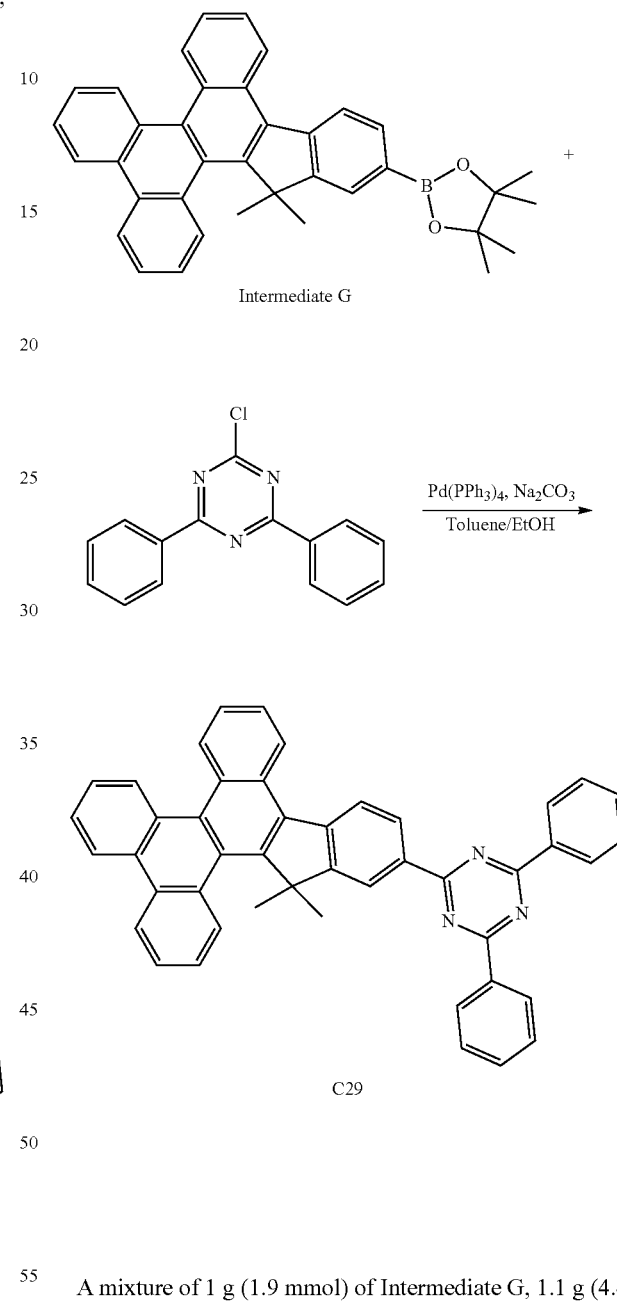

A mixture of 3 g (6.3 mmol) of Intermediate C, 2.1 g (9.4 mmol) of anthracen-9-ylboronic acid, 0.07 g (0.06 mmol) of Pd(PPh$_3$)$_4$, 13 ml of 2M Na$_2$CO$_{3(aq)}$, 30 ml of EtOH, and 90 ml of toluene was degassed and placed under nitrogen, and then heated at 100° C. for 12 hrs. After the reaction finished, the mixture was allowed to cool to room temperature, and then filtered to give compound C15 (3.1 g, 88%). MS (m/z, FAB+): 571.5.

A mixture of 1 g (1.9 mmol) of Intermediate G, 1.1 g (4.4 mmol) of 2-chloro-4,6-diphenyl-1,3,5-triazine, 0.01 g (0.01 mmol) of Pd(PPh$_3$)$_4$, 4 ml of 2M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, the organic layer was extracted with dichloromethane and water, and then dried with anhydrous MgSO$_4$. After the solvent was removed, the residue was purified by column chromatography on silica to give compound C29 (0.6 g, 53%). MS (m/z, FAB+): 626.5.

Example 4

Synthesis of Compound C37

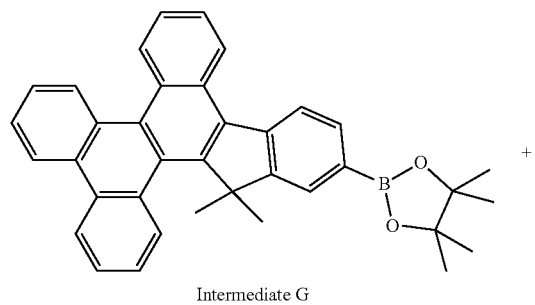

Intermediate G

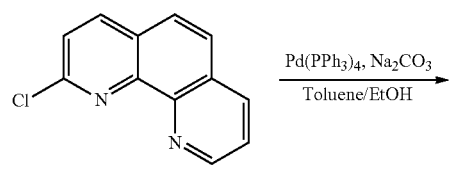

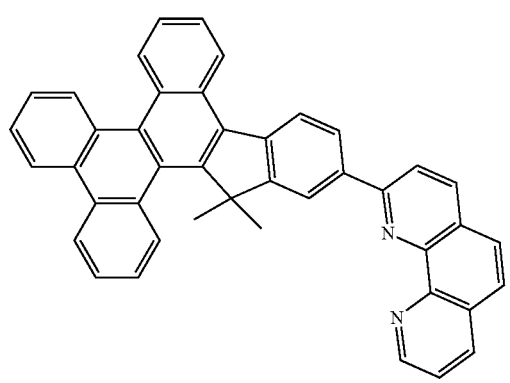

C37

A mixture of 1 g (1.9 mmol) of Intermediate G, 1.0 g (4.4 mmol) of 2-chloro-1,10-phenanthroline, 0.01 g (0.01 mmol) of Pd(PPh$_3$)$_4$, 4 ml of 2M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature. Subsequently, the organic layer was extracted with dichloromethane and water, and then dried with anhydrous MgSO$_4$. After the solvent was removed, the residue was purified by column chromatography on silica to give compound C37 (0.7 g, 68%). MS (m/z, FAB+): 573.6.

Example 5

Synthesis of Compound C23

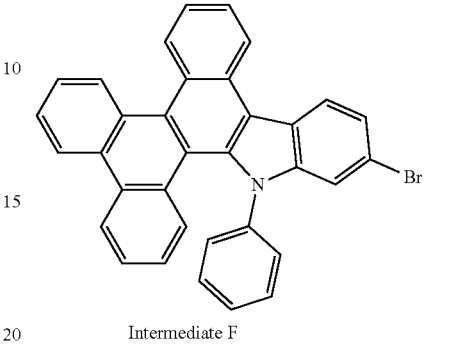

Intermediate F

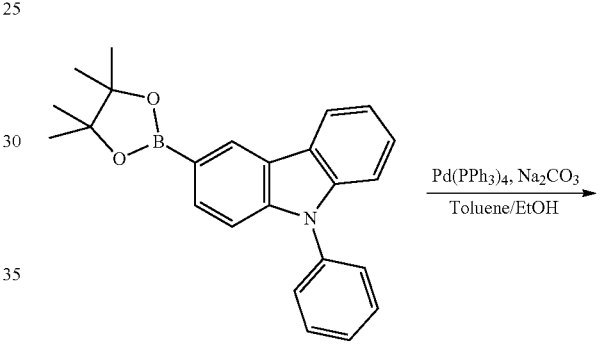

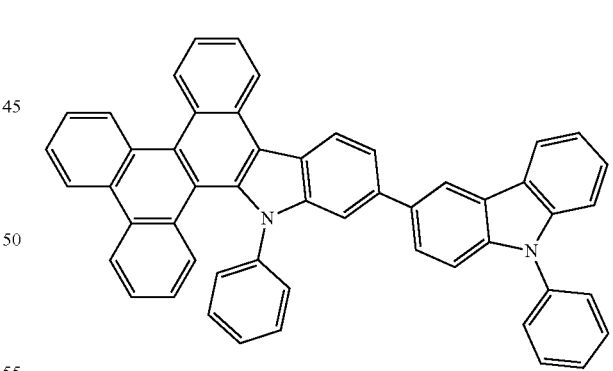

C23

A mixture of 1 g (1.9 mmol) of Intermediate F, 1.1 g (2.9 mmol) of 9-phenyl-3-(4,4,5,5-tetramethyl-1,3,2-dioxaborolan-2-yl)-9H-carbazole, 0.11 g (0.06 mmol) of Pd(PPh$_3$)$_4$, 3.8 ml of 2 M Na$_2$CO$_{3(aq)}$, 20 ml of EtOH, and 60 ml of toluene was degassed and placed under nitrogen, and then heated at 100° C. for 12 hrs. After the reaction finished, the mixture was allowed to cool to room temperature, and then filtered to give compound C23 (1.1 g, 82%). MS (m/z, FAB+): 685.8.

Example 6

Synthesis of Intermediate H

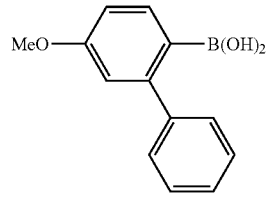

+

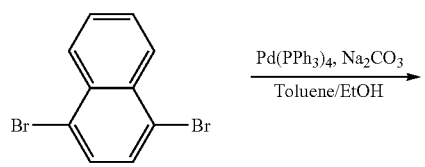

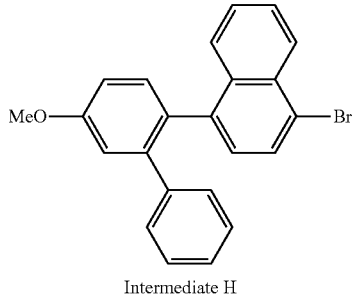

Intermediate H

A mixture of 10 g (43.9 mmol) of 5-methoxybiphenyl-2-ylboronic acid, 12.4 g (43.9 mmol) of 1,4-dibromonaphthalene, 0.5 g (0.44 mmol) of Pd(PPh$_3$)$_4$, 87.8 ml of 2 M Na$_2$CO$_{3(aq)}$, 100 ml of EtOH, and 300 ml of toluene was degassed and placed under nitrogen, and then heated at 100° C. for 12 hrs. After the reaction finished, the mixture was allowed to cool to room temperature, and then filtered to give Intermediate H (12.6 g, 74%).

Synthesis of Intermediate I

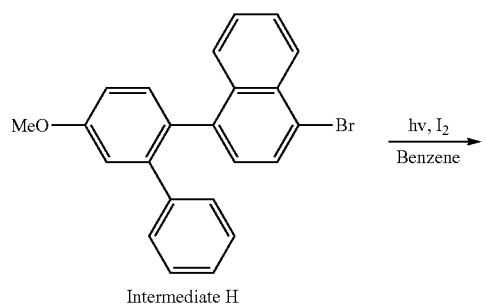

Intermediate H

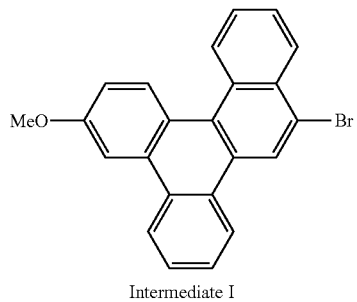

Intermediate I

A mixture of 10 g (25.7 mmol) of Intermediate H, 0.07 g (0.25 mmol) of Iodine, and 1000 ml of benzene was degassed and placed under nitrogen, and then exposed to UV light for 4 hrs. After the reaction finished, the solvent was removed, and then the residue was recrystallized 3 times to give Intermediate I (2.3 g, 23%).

Synthesis of Intermediate J

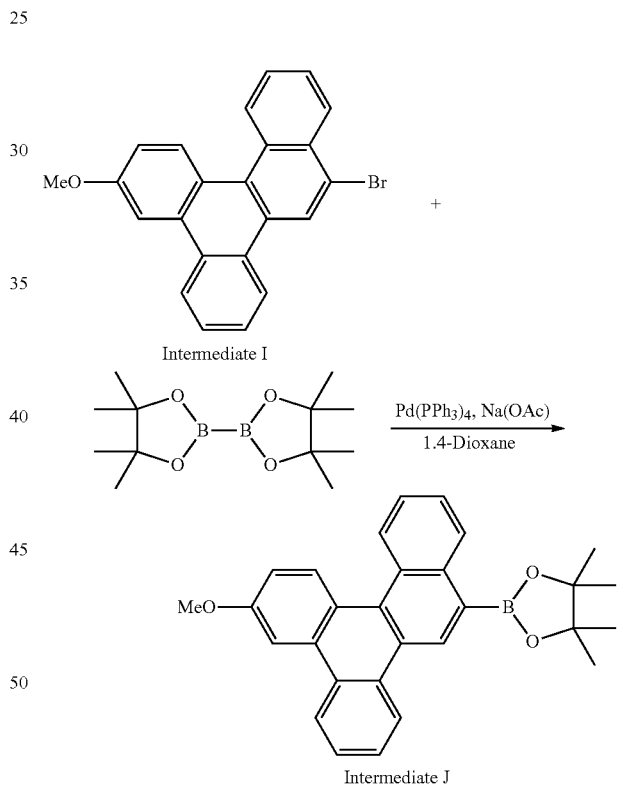

A mixture of 2 g (5.2 mmol) of Intermediate I, 1.4 g (5.5 mmol) of 4,4,4',4',5,5,5',5'-octamethyl-2,2'-bi(1,3,2-dioxaborolane), 0.30 g (0.2 mmol) of Pd(PPh$_3$)$_4$, 0.6 g (7.8 mmol) of sodium acetate, and 50 ml of 1,4-dioxane was degassed and placed under nitrogen, and then heated at 100° C. for 6 hrs. After the reaction finished, the mixture was allowed to cool to room temperature. Subsequently, the organic layer was extracted with ethyl acetate and water, and then dried with anhydrous magnesium sulfate. After the solvent was removed, the residue was purified by column chromatography on silica to give Intermediate J (1.7 g, 65%).

Synthesis of Intermediate K

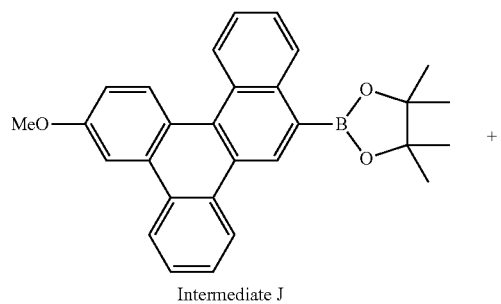

Intermediate J

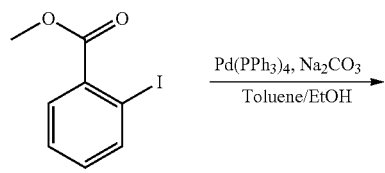

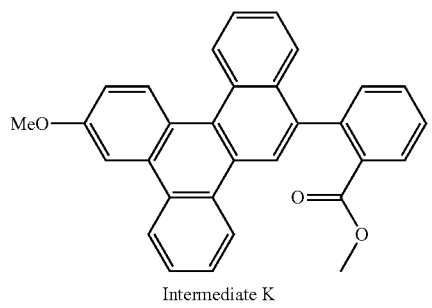

Intermediate K

A mixture of 1 g (2.3 mmol) of Intermediate J, 0.6 g (2.3 mmol) of methyl 2-iodobenzoate, 0.05 g (0.05 mmol) of Pd(PPh$_3$)$_4$, 1.2 ml of 2 M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature, and then filtered to give Intermediate K (1.0 g, 80%).

Synthesis of Intermediate L

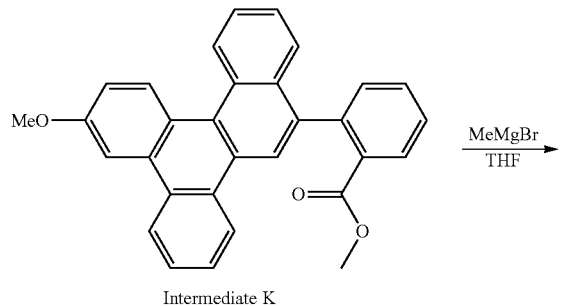

Intermediate K

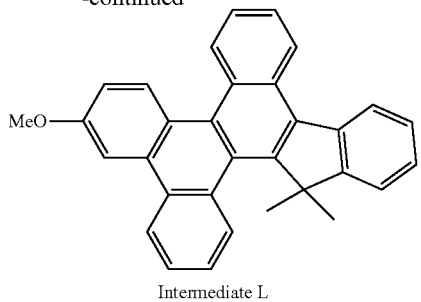

Intermediate L

Under the nitrogen gas, while 1.5 g (3.4 mmol) of Intermediate K was stirred in dry THF, methyl magnesium bromide (6 equivalents) was slowly added dropwise thereto. The mixture was stirred overnight at room temperature. After completion of the reaction, a little distilled water was slowly added, and then the mixture was extracted with ethyl acetate and washed with water. The organic layer was dried with anhydrous MgSO$_4$, and then the solvent was removed to obtain a residue. Subsequently, excess phosphoric acid solvent (~10 ml) was added to the residue, which was then stirred at room temperature for more than 16 hrs. Afterwards, distilled water (~50 ml) was slowly added, followed by stirring for 1 hour. After the precipitated solids were filtered, the filtered solids were extracted with dichloromethane solvent and then washed with sodium hydroxide aqueous solution. Subsequently, the dichloromethane solvent layer was taken out and then the moisture was removed by using magnesium sulfate. Finally, the residual solvent was removed to obtain the Intermediate L (0.4 g, 30%).

Synthesis of Compound C87

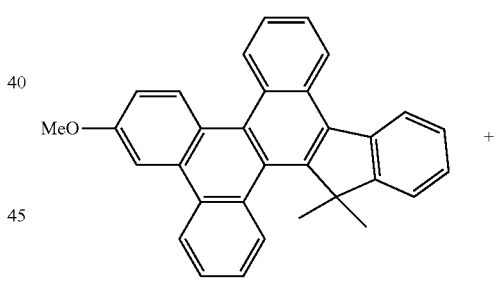

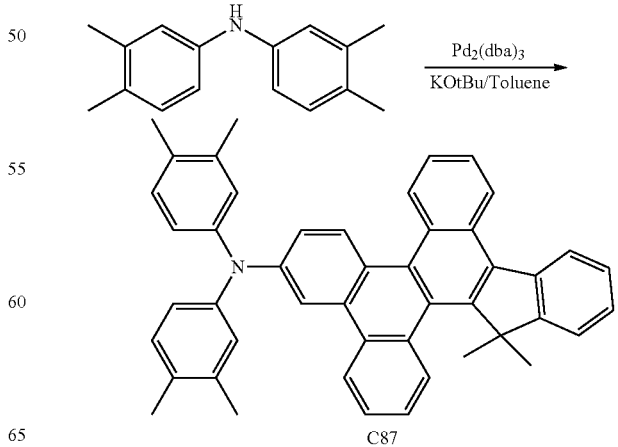

A mixture of 1.0 g (2.3 mmol) of Intermediate L, 1.2 g (5.2 mmol) of bis(3,4-dimethylphenyl)amine, 0.21 g (0.23 mmol) of $Pd_2(dba)_3$, 0.5 g (4.6 mmol) of potassium tert-butoxide, and 30 ml of toluene was degassed and placed under nitrogen gas, and then heated at 110° C. for 16 hrs. After the reaction finished, the mixture was allowed to cool to room temperature. Subsequently, the organic layer was extracted with dichloromethane and water, and then dried with anhydrous $MgSO_4$. After the solvent was removed, the residue was purified by column chromatography on silica to give compound C87 (1.0 g, 72%). MS (m/z, FAB+): 618.3.

Example 7

Synthesis of Intermediate M

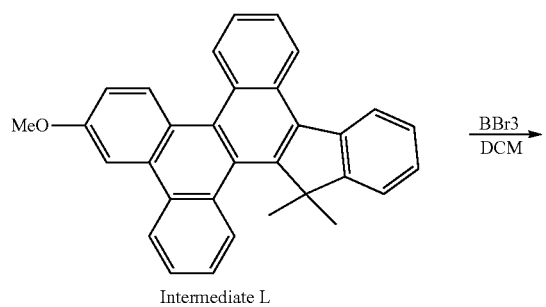

Intermediate L

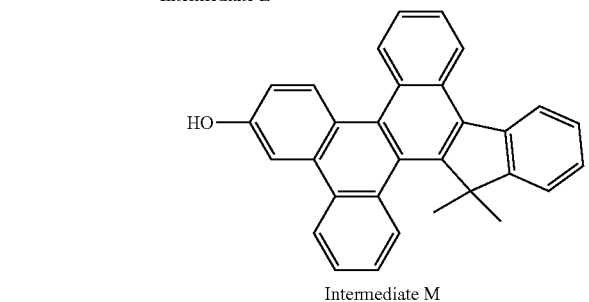

Intermediate M

A mixture of 1 g (1.9 mmol) of Intermediate L and dichloromethane (30 ml) was placed into the reactor under nitrogen. Boron tribromide (1 eq.) was added thereto and then stirred for 2 hrs until the reaction finished. The reaction mixture was extracted with dichloromethane and water, and then dried with anhydrous $MgSO_4$. The solvent was removed to give Intermediate M (0.63 g, yield=88%).

Synthesis of Intermediate N

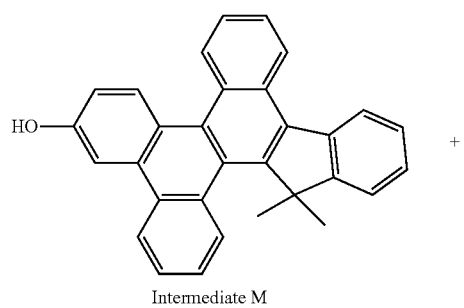

Intermediate M

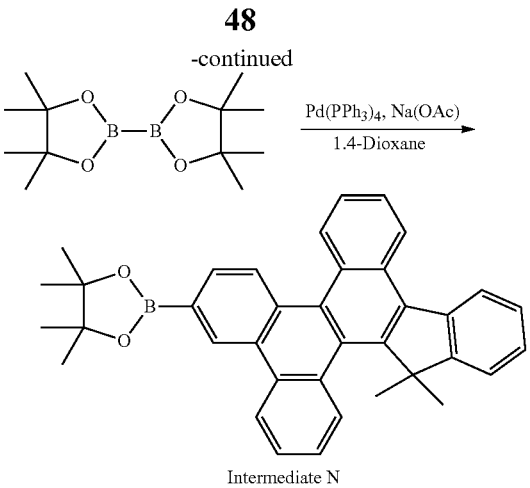

Intermediate N

A mixture of 1 g (2.4 mmol) of Intermediate M, 0.7 g (2.8 mmol) of 4,4,4',4',5,5,5',5'-octamethyl-2,2'-bi(1,3,2-dioxaborolane), 0.12 g (0.1 mmol) of $Pd(PPh_3)_4$, 0.3 g (3.6 mmol) of sodium acetate, and 30 ml of 1,4-dioxane was degassed and placed under nitrogen, and then heated at 100° C. for 6 hrs. After the reaction finished, the mixture was allowed to cool to room temperature. Subsequently, the organic layer was extracted with ethyl acetate and water, and then dried with anhydrous magnesium sulfate. After the solvent was removed, the residue was purified by column chromatography on silica to give Intermediate N (1.0 g, 65%).

Synthesis of Compound C88

C88

A mixture of 1.0 g (1.9 mmol) of Intermediate N, 0.6 g (1.2 mmol) of 1-bromopyrene, 0.11 g (0.09 mmol) of Pd(PPh$_3$)$_4$, 1.0 ml of 2M Na$_2$CO$_{3(aq)}$, 10 ml of EtOH, and 30 ml of toluene was degassed and placed under nitrogen, and then heated at 100° C. for 12 hrs. After the reaction finished, the mixture was allowed to cool to room temperature, and then filtered to give compound C88 (1.0 g, 88%). MS (m/z, FAB+): 595.2.

Example 8

Synthesis of Intermediate O

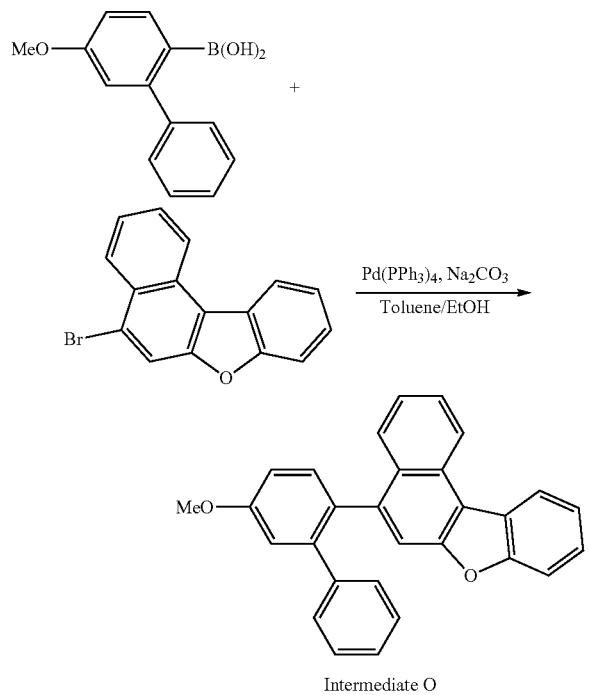

Intermediate O

The same synthesis procedure as in Synthesis of Intermediate H was used, except that 10 g of 5-bromobenzo[d]naphtho[2,1-b]furan was used instead of 1,4-dibromonaphthalene to obtain the desired Intermediate O (11.6 g, 66%).

Synthesis of Intermediate P

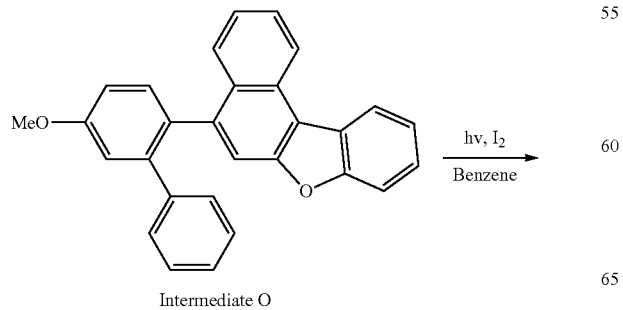

Intermediate O

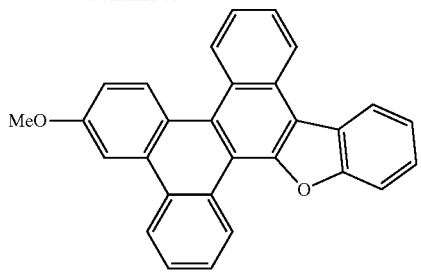

Intermediate P

The same synthesis procedure as in Synthesis of Intermediate I was used, except that 11.6 g of Intermediate O was used instead of Intermediate H to obtain the desired Intermediate P (3.2 g, 28%).

Synthesis of Intermediate Q

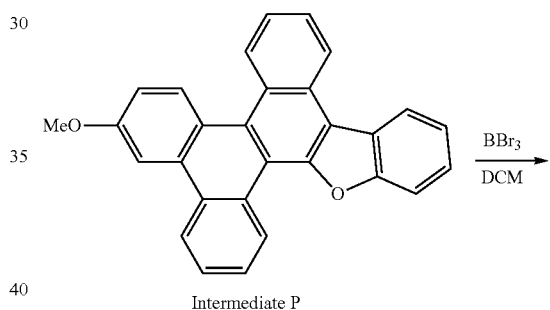

Intermediate P

Intermediate Q

The same synthesis procedure as in Synthesis of Intermediate M was used, except that 10 g of Intermediate P was used instead of Intermediate L to obtain the desired Intermediate Q (8.5 g, 88%).

Synthesis of Intermediate R

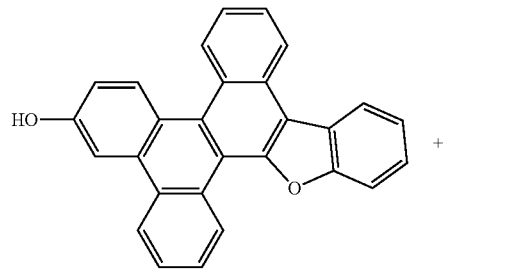

Intermediate Q

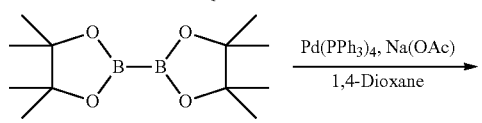

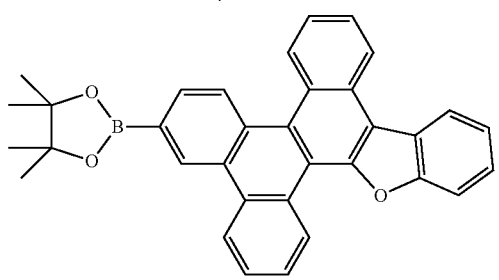

Intermediate R

The same synthesis procedure as in Synthesis of Intermediate N was used, except that 8.5 g of Intermediate Q was used instead of Intermediate M to obtain the desired Intermediate R (7.3 g, 65%).

Synthesis of Compound C89

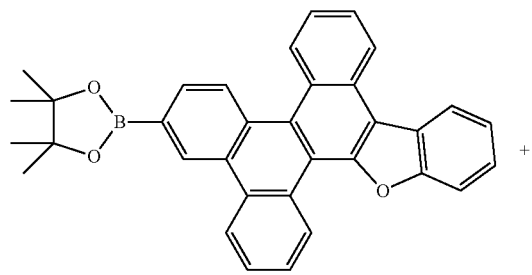

Intermediate R

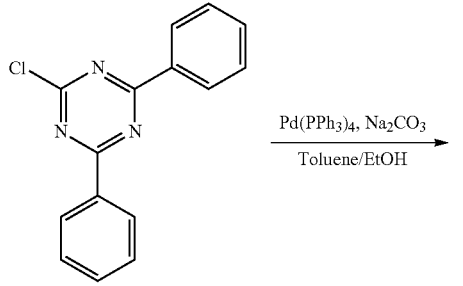

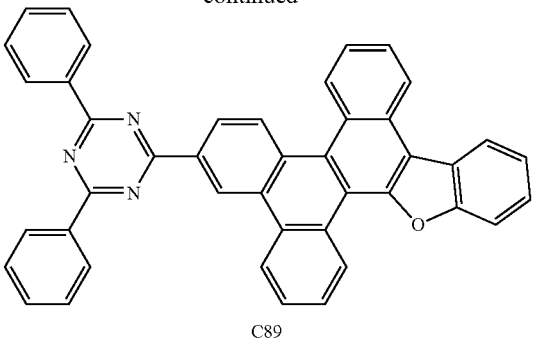

C89

The same synthesis procedure as in Synthesis of compound C88 was used, except that 2 g of Intermediate R was used instead of Intermediate N and 2-chloro-4,6-diphenyl-1,3,5-triazine was used instead of 1-bromopyrene to obtain the desired compound C89 (0.7 g, 60%).

Example 9

Synthesis of Intermediate S

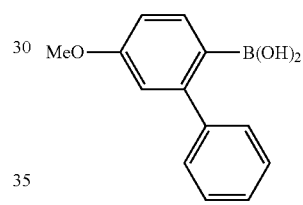

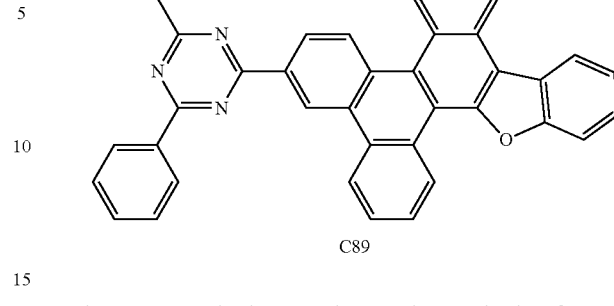

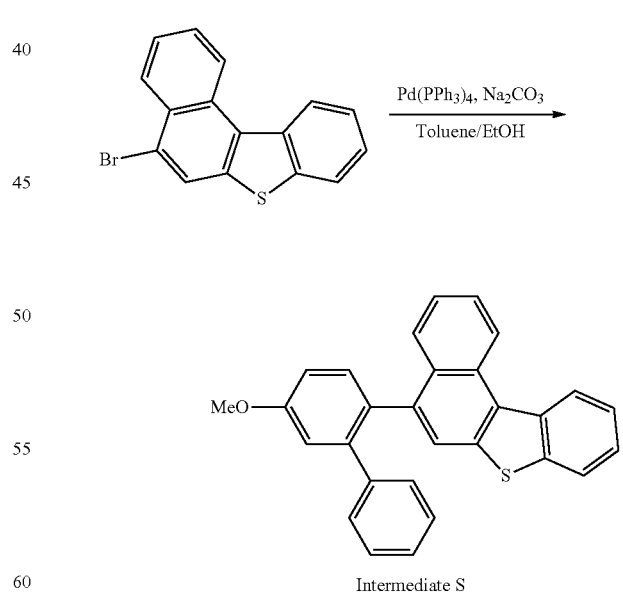

Intermediate S

The same synthesis procedure as in Synthesis of Intermediate H was used, except that 10 g of 5-bromobenzo[d]naphtho[2,1-b]thiophene was used instead of 1,4-dibromonaphthalene to obtain the desired Intermediate S (10.0 g, 55%).

Synthesis of Intermediate T

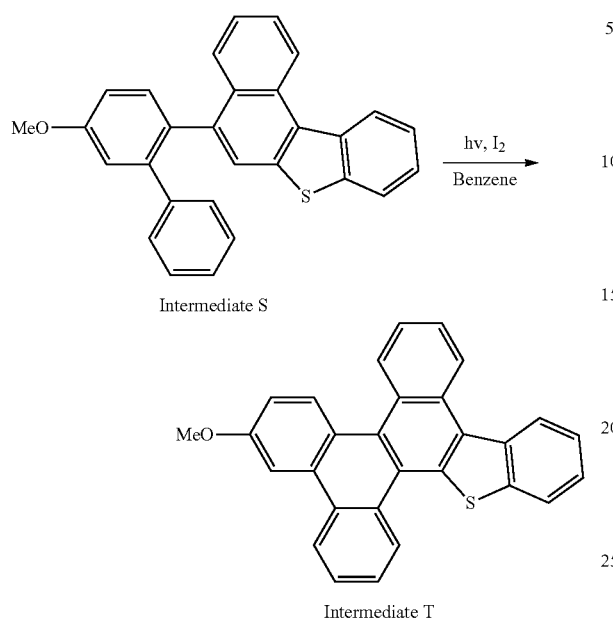

Intermediate S

Intermediate T

The same synthesis procedure as in Synthesis of Intermediate I was used, except that 10.0 g of Intermediate S was used instead of Intermediate H to obtain the desired Intermediate T (3.2 g, 32%).

Synthesis of Intermediate U

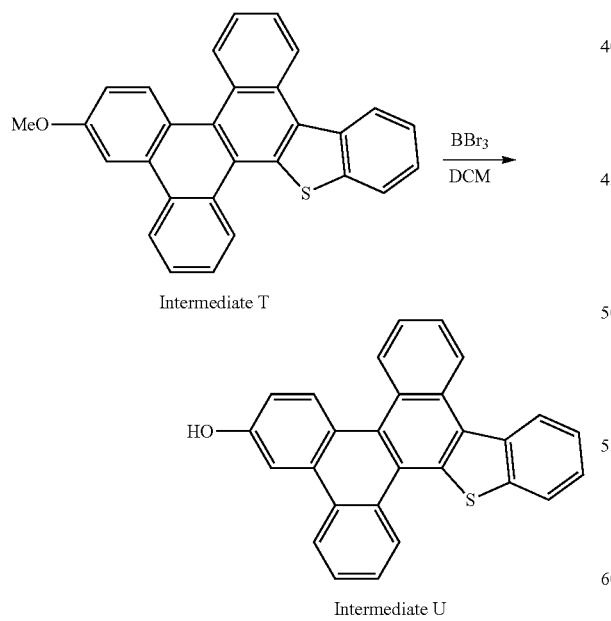

Intermediate T

Intermediate U

The same synthesis procedure as in Synthesis of Intermediate M was used, except that 3.2 g of Intermediate T was used instead of Intermediate L to obtain the desired Intermediate U (2.5 g, 80%).

Synthesis of Intermediate V

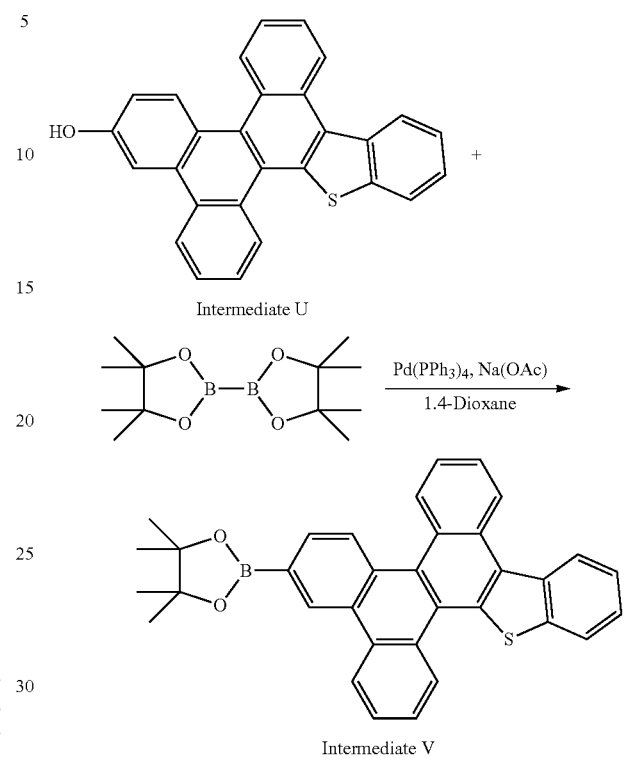

Intermediate U

Intermediate V

The same synthesis procedure as in Synthesis of Intermediate N was used, except that 3.2 g of Intermediate U was used instead of Intermediate M to obtain the desired Intermediate V (2.9 g, 75%).

Synthesis of Compound C90

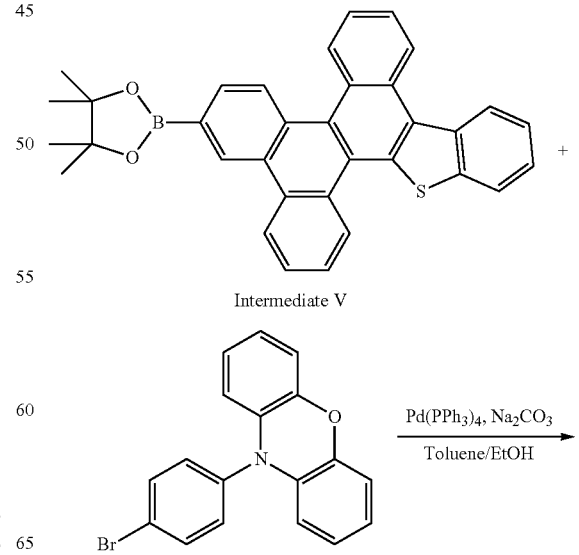

Intermediate V

-continued

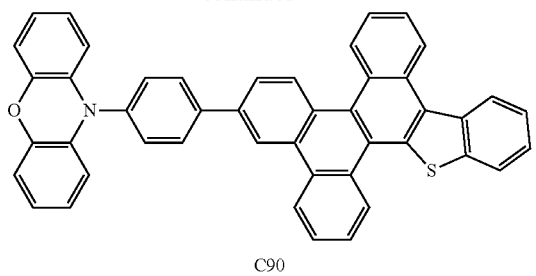

C90

The same synthesis procedure as in Synthesis of compound C88 was used, except that 2 g of Intermediate V was used instead of Intermediate N and 1.3 g of 10-(4-bromophenyl)-10H-phenoxazine was used instead of 1-bromopyrene to obtain the desired compound C90 (1.9 g, 76%).

Example 10

Synthesis of Intermediate W

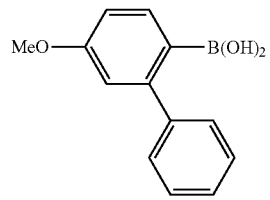

+

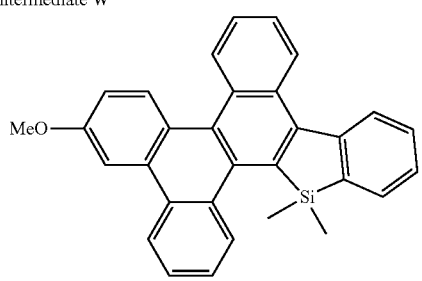 $\xrightarrow{\text{Pd(PPh}_3)_4, \text{Na}_2\text{CO}_3}{\text{Toluene/EtOH}}$

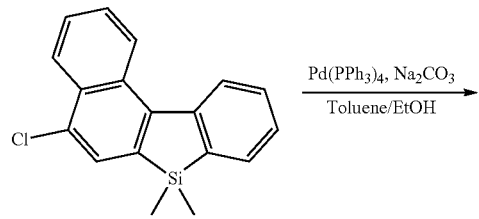

Intermediate W

The same synthesis procedure as in Synthesis of Intermediate H was used, except that 10 g of 5-chloro-7,7-dimethyl-7H-benzo[d]naphtho[2,1-b]silole was used instead of 1,4-dibromonaphthalene to obtain the desired Intermediate W (12.0 g, 62%).

Synthesis of Intermediate X

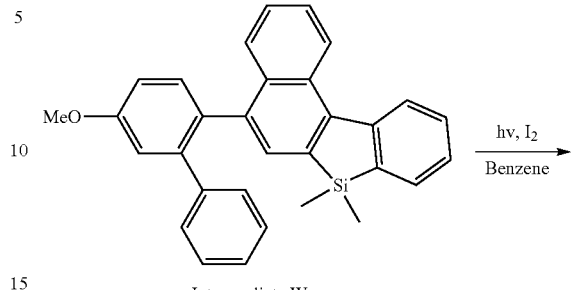

Intermediate W $\xrightarrow{\text{hv, I}_2}{\text{Benzene}}$

Intermediate X

The same synthesis procedure as in Synthesis of Intermediate I was used, except that 12.0 g of Intermediate W was used instead of Intermediate H to obtain the desired Intermediate X (2.5 g, 21%).

Synthesis of Intermediate Y

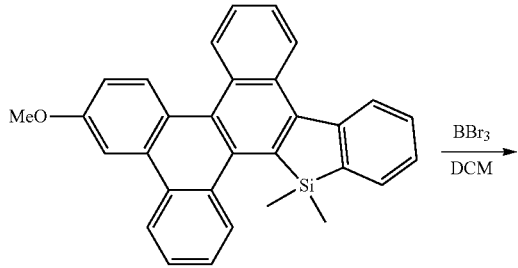

Intermediate X $\xrightarrow{\text{BBr}_3}{\text{DCM}}$

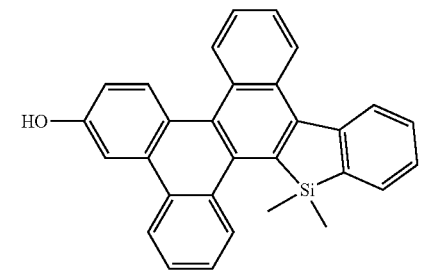

Intermediate Y

The same synthesis procedure as in Synthesis of Intermediate M was used, except that 2.5 g of Intermediate X was used instead of Intermediate L to obtain the desired Intermediate Y (1.5 g, 64 (Y0).

Synthesis of Intermediate Z

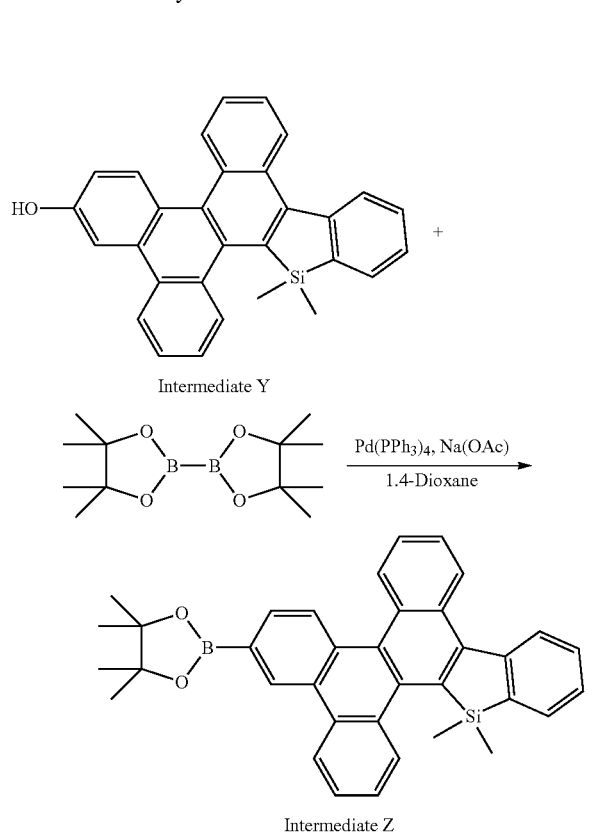

Intermediate Y

Intermediate Z

The same synthesis procedure as in Synthesis of Intermediate N was used, except that 1.5 g of Intermediate Y was used instead of Intermediate M to obtain the desired Intermediate Z (1.3 g, 69%).

Synthesis of Compound C91

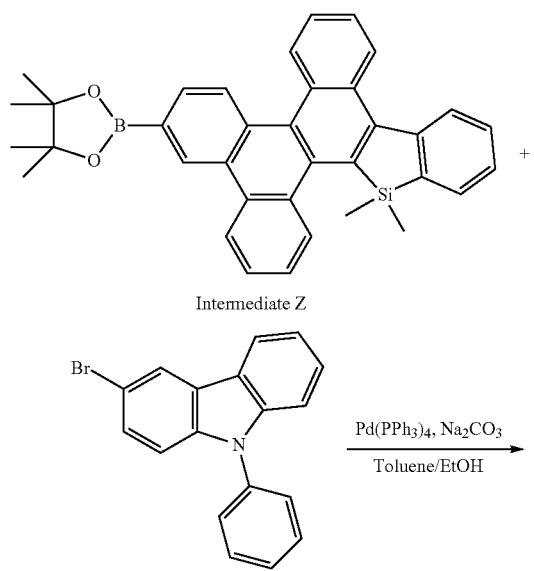

Intermediate Z

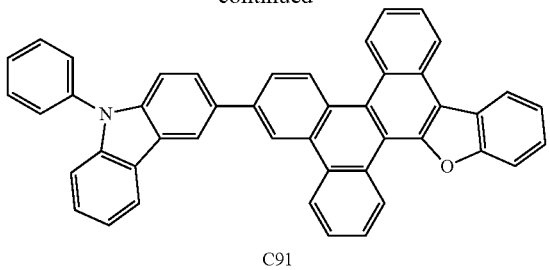

C91

The same synthesis procedure as in Synthesis of compound C88 was used, except that 1.3 g of Intermediate Z was used instead of Intermediate N and 0.7 g of 3-bromo-9-phenyl-9H-carbazole was used instead of 1-bromopyrene to obtain the desired compound C91 (1.3 g, yield=85%).

General Method of Producing Organic EL Device

ITO-coated glasses with 12 ohm/square in resistance and 120 nm in thickness are provided (hereinafter ITO substrate) and cleaned in a number of cleaning steps in an ultrasonic bath (e.g. detergent, deionized water). Before vapor deposition of the organic layers, cleaned ITO substrates are further treated by UV and ozone. All pre-treatment processes for ITO substrates are under clean room (class 100).

The organic layers are applied onto the ITO substrate in order by vapor deposition in a high-vacuum unit ($10^{-7}$ Torr), such as: resistively heated quartz boats. The thickness of the respective layer and the vapor deposition rate (0.1-0.3 nm/sec) are precisely monitored or set with the aid of a quartz-crystal monitor. It is also possible, as described above, for individual layers to consist of more than one compound, i.e. in general a host material doped with a dopant material. This is successfully achieved by co-vaporization from two or more sources, which means the organic compounds of the present invention are thermally stable.

Dipyrazino[2,3-f:2,3-]quinoxaline-2,3,6,7,10,11-hexacarbonitrile (HAT-CN) is used to form the hole injection layer, and N,N-bis(naphthalene-1-yl)-N,N-bis(phenyl)-benzidine (NPB) is used to form the hole transporting layer of the organic EL device. 2,9-bis(naphthalene-2-yl)-4,7-diphenyl-1,10-phenanthroline (NPhen) is used as the electron transporting material in organic EL device for its high thermal stability and long life-time than BPhen or BCP. For fluorescence emitting device, 1,1'-(9,9-dimethyl-9H-fluorene-2,7-diyl)dipyrene (DFDP) is used as the host material, and (E)-6-(4-(diphenylamino)styryl)-N,N-diphenylnaphthalen-2-amine (D1) is used as the fluorescent dopant. For phosphorescence emitting device, bis(2-methyl-8-quinolinolate)-4-(phenylphenolato)aluminium (BAlq) is used as the host material of emitting layer, and tris(1-phenylisoquinoline)-Iridium(III) (Ir(piq)$_3$) or tris(2-phenylquinoline)iridium(III) (Ir(2-phq)$_3$) is used as the dopant material. Compounds C15 and C88 are used as the fluorescent host materials to compare with DFDP. Compounds C2, C87, and C90 are used as the fluorescent dopant materials to compare with D1. Compounds C29, C37, and C89 are used as the electron transporting materials to compare with NPhen. Compounds C23, C29, and C91 are used as the phosphorescent host materials to compare with BAlq. The chemical structures of conventional OLED materials and the exemplary organic compounds of the present invention for producing control and exemplary organic EL devices in this invention are shown as follows:

-continued
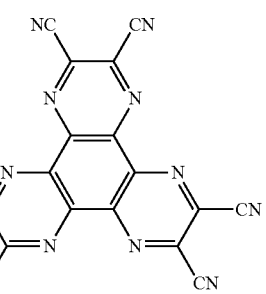
HAT-CN
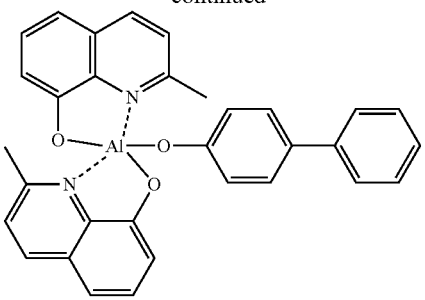
BAlq
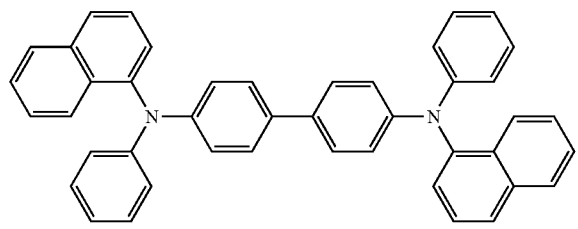
NPB
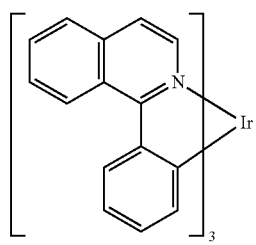
Ir(piq)₃
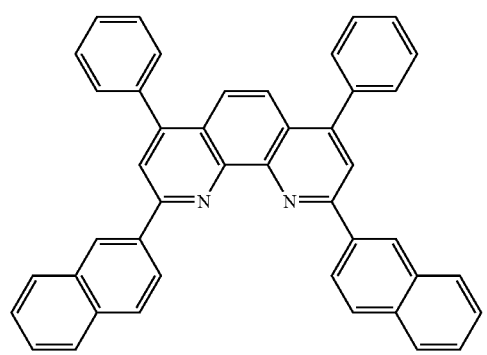
NPhen
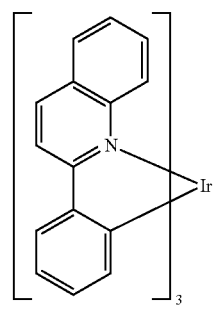
Ir(2-phq)₃
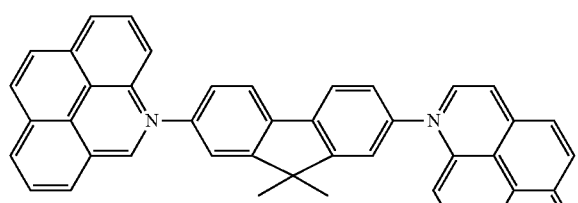
DFDP
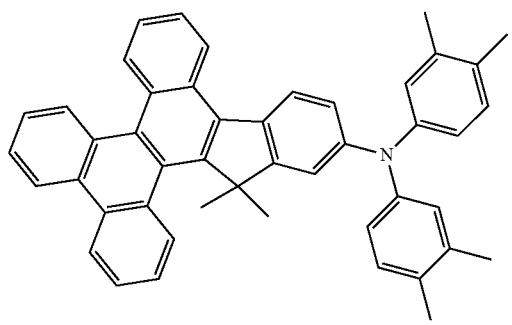
C2
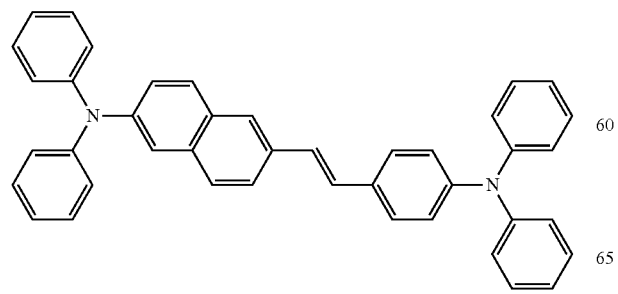
D1
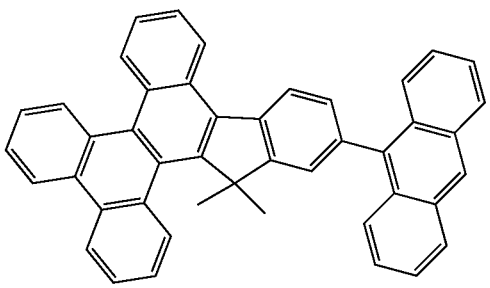
C15

-continued

C29
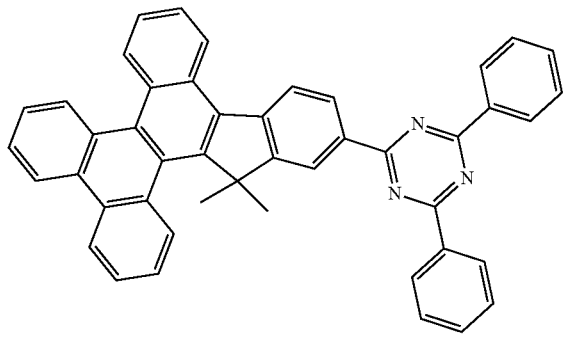

C37
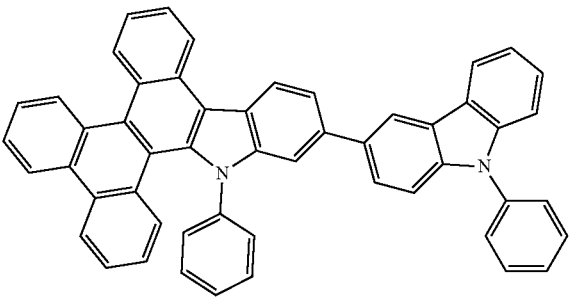

C23
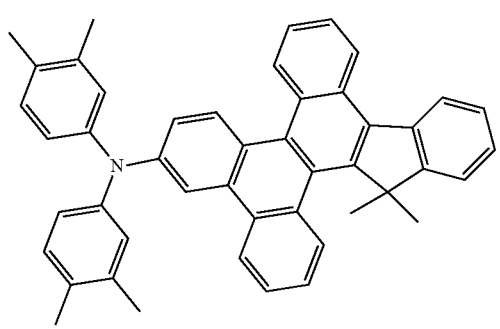

C87

-continued

C88
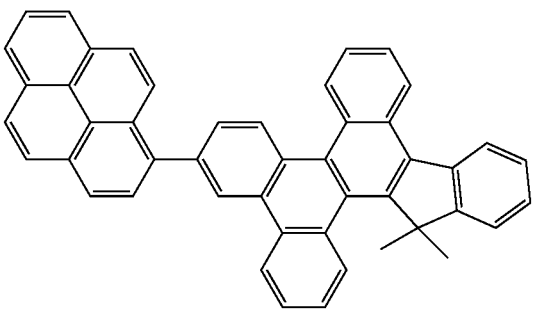

C89
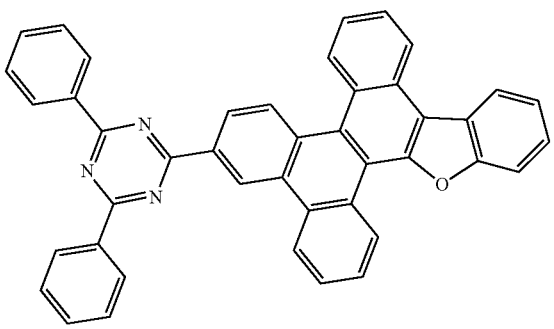

C90
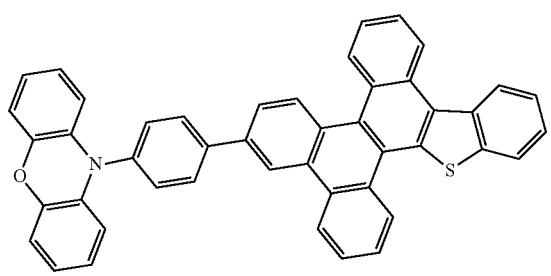

C91
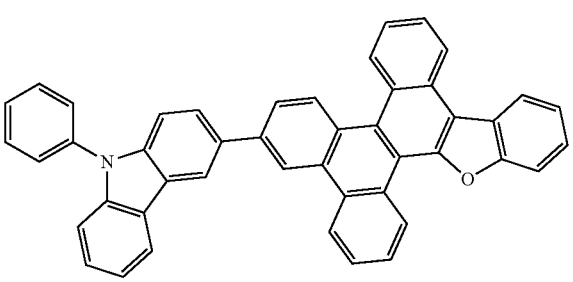

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, MgO, or $Li_2O$.

On the other hand, after the organic EL device fabrication, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

Example 11

Using a procedure analogous to the above-mentioned general method, organic EL devices emitting blue fluorescence and having the following device structure as shown in the FIGURE were produced: ITO/HAT-CN(20 nm)/NPB(50 nm)/fluorescent blue host (DFDP or C15 or C88)+5% dopant(D1 or C2, C87, or C90) (30 nm)/NPhen (30 nm)/LiF (0.5 nm)/Al(160 nm). The I—V—B and half-life time test reports of these fluorescent blue-emitting organic EL devices are summarized in Table 1 below, and the half-life time is defined as the time the initial luminance of 3000 cd/m² has dropped to half.

TABLE 1

| Fluorescent blue host + 5% dopant | Voltage (V) | Luminance (cd/m²) | Efficiency (cd/A) | CIE (y) | Half-life time (hr) |
|---|---|---|---|---|---|
| DFDP + D1 | 6 | 971 | 5.12 | 0.17 | 310 |
| DFDP + C2 | 6 | 1426 | 7.52 | 0.14 | 480 |
| DFDP + C87 | 6 | 1120 | 5.90 | 0.15 | 450 |
| DFDP + C90 | 6 | 1196 | 6.31 | 0.15 | 421 |
| C15 + D1 | 6 | 1181 | 6.23 | 0.15 | 410 |
| C88 + D1 | 6 | 1223 | 6.45 | 0.15 | 380 |

From the above test report summary of the organic EL devices, it is obvious that the organic compound of formula (I) used as the fluorescent blue host or dopant material exhibits better performance than the prior art materials. In particular, the organic EL devices of the present invention employing the organic compound of formula (I) as the dopant material or host material to collocate with the host material DFDP or the dopant material D1 have higher luminance and current efficiency, longer half-life time, and improved deep blue emission under the same voltage.

Example 12

Using a procedure analogous to the above-mentioned general method, organic EL device having the following device structure were produced (See the FIGURE): ITO/HAT-CN(20 nm)/NPB(50 nm)/DFDP+5% D1 (30 nm)/NPhen or C29, C37, or C89(30 nm)/LiF(0.5 nm)/Al(160 nm). The I—V—B and half-life time test reports of these blue fluorescence-emitting organic EL devices are summarized in Table 2 below, and the half-life time is defined as the time the initial luminance of 3000 cd/m² has dropped to half.

TABLE 2

| ETM | Voltage (V) | Efficiency (cd/A) | CIE (y) | Half-life time (hr) |
|---|---|---|---|---|
| NPhen | 6.2 | 5.12 | 0.17 | 310 |
| C29 | 4.9 | 8.50 | 0.17 | 425 |
| C37 | 4.8 | 7.92 | 0.17 | 463 |
| C89 | 5.1 | 8.3 | 0.17 | 552 |

From the above test report summary of the organic EL devices, it is obvious that the organic compound of formula (I) used as the electron transporting material exhibits better performance than the prior art material NPhen. In particular, the organic EL devices of the present invention employing the organic compound of formula (I) as the electron transporting material to collocate with the host material DFDP and the dopant material D1 have lower power consumption, higher current efficiency, and longer half-life time.

Example 13

Using a procedure analogous to the above-mentioned general method, organic EL devices emitting phosphorescence and having the following device structure were produced (See the FIGURE): ITO/HAT-CN(20 nm)/NPB(50 nm)/phosphorescent host (C29, C23, or C91)+10% dopant (30 nm)/NPhen (30 nm)/LiF(0.5 nm)/Al(160 nm). The I—V—B and half-life time test reports of these phosphorescence emitting organic EL devices are summarized in Table 3 below, and the half-life time is defined as the time the initial luminance of 3000 cd/m² has dropped to half.

TABLE 3

| Phosphorescent host + 10% dopant | Voltage (V) | Luminance (cd/m²) | Efficiency (cd/A) | Device color | Half-life time (hr) |
|---|---|---|---|---|---|
| BAlq + Ir(piq)₃ | 6 | 671 | 8.14 | red | 450 |
| BAlq + Ir(2-phq)₃ | 6 | 511 | 14.12 | yellow | 472 |
| C29 + Ir(piq)₃ | 6 | 952 | 11.55 | red | 680 |
| C29 + Ir(2-phq)₃ | 6 | 1280 | 35.36 | yellow | 1036 |
| C23 + Ir(piq)₃ | 6 | 1030 | 12.49 | red | 894 |
| C23 + Ir(2-phq)₃ | 6 | 1200 | 33.15 | yellow | 1032 |
| C91 + Ir(piq)₃ | 6 | 1241 | 15.05 | red | 804 |
| C91 + Ir(2-phq)₃ | 6 | 1311 | 36.22 | yellow | 984 |

From the above test report summary of the organic EL devices, it is obvious that the organic compound of formula (I) used as the phosphorescent host material exhibits better performance than the prior art material BAlq. In particular, the organic EL devices of the present invention employing the organic compound of formula (I) as the phosphorescent host material to collocate with the dopant material Ir(piq)₃ or Ir(2-phq)₃ have higher luminance and current efficiency and longer half-life time under the same voltage.

To sum up, the present invention discloses an organic compound, which can be used as the phosphorescent host material, the fluorescent host material, or the fluorescenct dopant material of the light emitting layer, or the electron transporting material in organic EL devices. The mentioned organic compound is represented by the following formula (I):

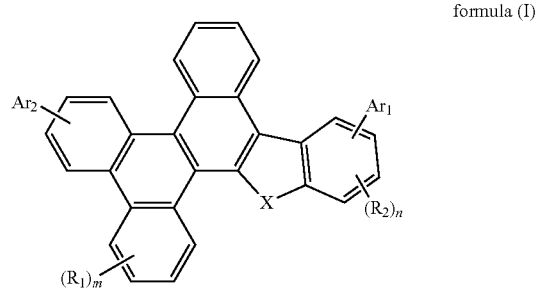

formula (I)

wherein m is an integer of 0 to 11; n is an integer of 0 to 3; X is O, S, $C(R_3)(R_4)$, $N(Ar_3)$, or $Si(R_5)(R_6)$; $Ar_1$, $Ar_2$, and $Ar_3$ are each independently a hydrogen atom, a halide, a substituted or unsubstituted arylamine group having 5 to 50 ring atoms, a substituted or unsubstituted heteroarylamine group having 5 to 50 ring atoms, a substituted or unsubstituted aryl group having 5 to 50 ring atoms, or a substituted or unsubstituted heteroaryl group having 5 to 50 ring atoms; and $R_1$ to $R_6$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:
1. An organic compound of formula (I) below:

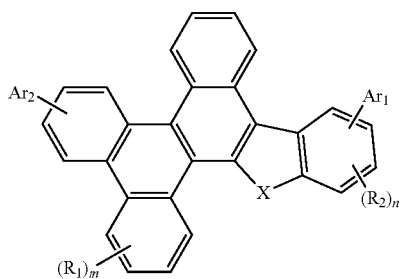

formula (I)

wherein m is an integer of 0 to 11; n is an integer of 0 to 3; X is O, S, $C(R_3)(R_4)$, $N(Ar_3)$, or $Si(R_5)(R_6)$; $Ar_1$, $Ar_2$, and $Ar_3$ are each independently a hydrogen atom, a halide, a substituted or unsubstituted arylamine group having 5 to 50 ring atoms, a substituted or unsubstituted heteroarylamine group having 5 to 50 ring atoms, a substituted or unsubstituted aryl group having 5 to 50 ring atoms, or a substituted or unsubstituted heteroaryl group having 5 to 50 ring atoms; and $R_1$ to $R_6$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 6 to 30 carbon atoms, and a substituted or unsubstituted heteroaryl group having 3 to 30 carbon atoms.

2. The organic compound of claim 1, wherein $Ar_1$, $Ar_2$, and $Ar_3$ are independently selected from the group consisting of a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group, a substituted or unsubstituted arylamine group, a substituted or unsubstituted heteroarylamine group, a substituted or unsubstituted benzimidazole group, a substituted or unsubstituted carbazolyl group, a substituted or unsubstituted biscarbazolyl group, a substituted or unsubstituted dibenzofuranyl group, a substituted or unsubstituted dibenzothiophenyl group, a substituted or unsubstituted diphenylphosphine oxide group, a substituted or unsubstituted triazinyl group, a substituted or unsubstituted diazinyl group, a substituted or unsubstituted pyridinyl group, a substituted or unsubstituted phenanthroline group, a substituted or unsubstituted dihydroacridine group, a substituted or unsubstituted phenothiazine group, a substituted or unsubstituted phenoxazine group, and a substituted or unsubstituted dihydrophenazine group.

3. The organic compound of claim 1, wherein $Ar_1$, $Ar_2$, or $Ar_3$ represents one of the following substituents:

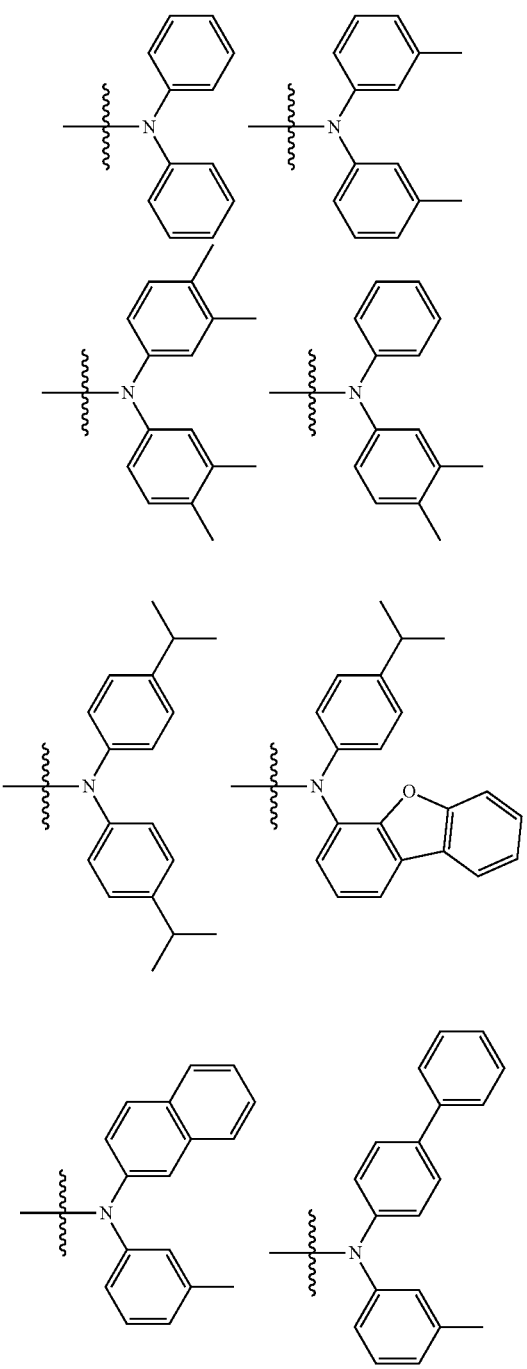

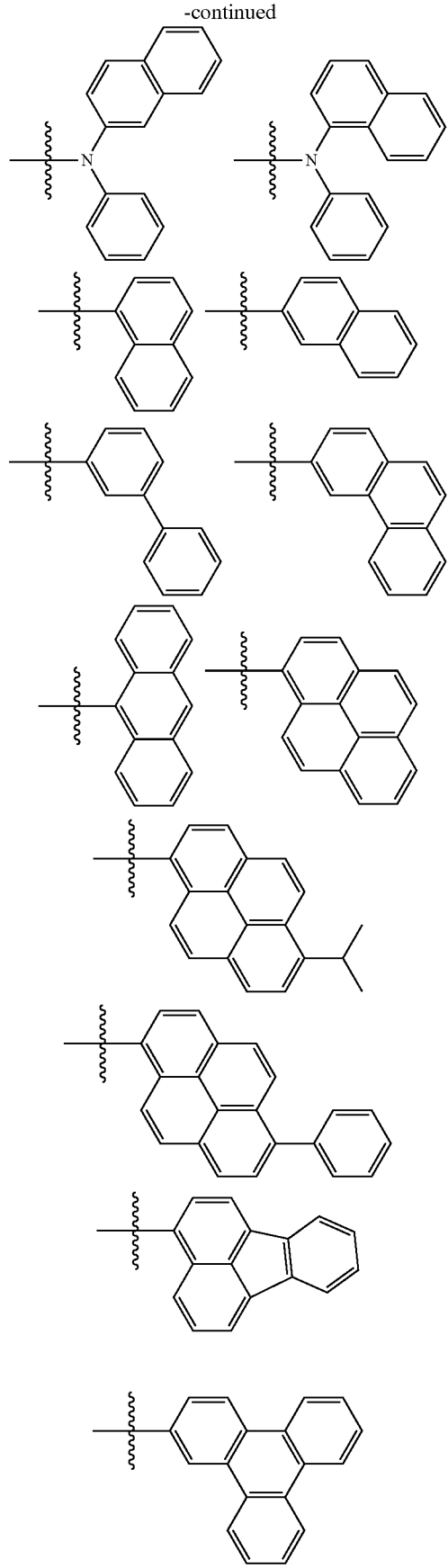
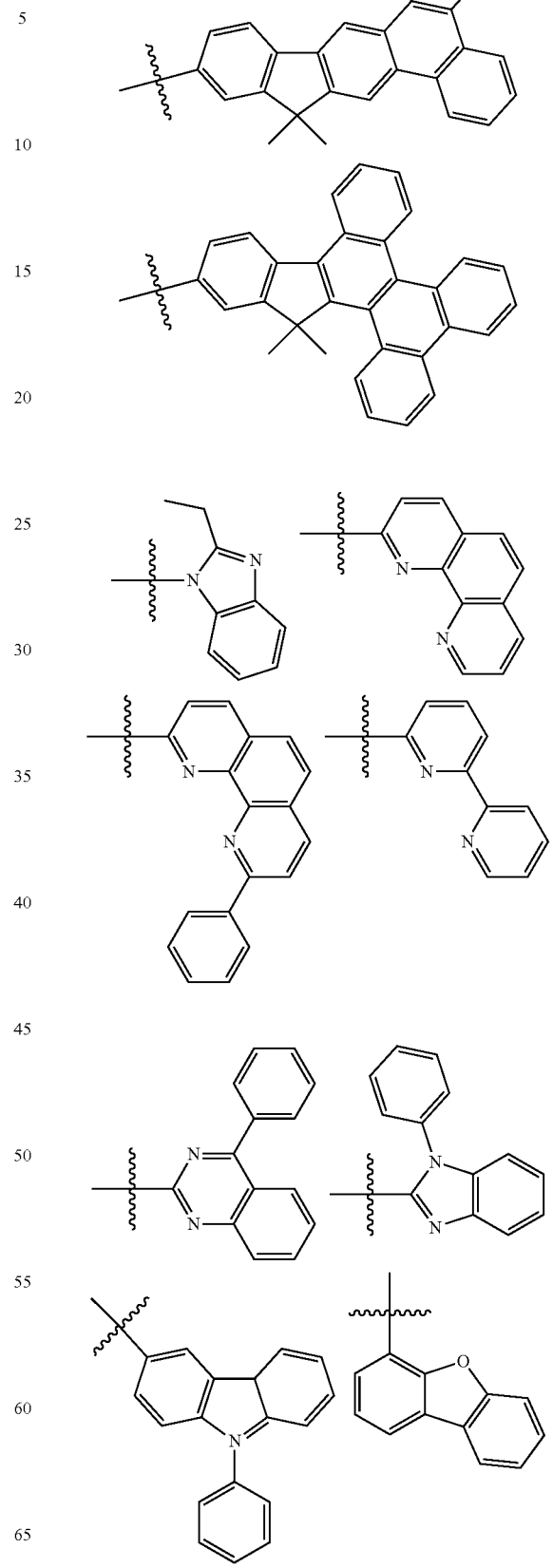

-continued
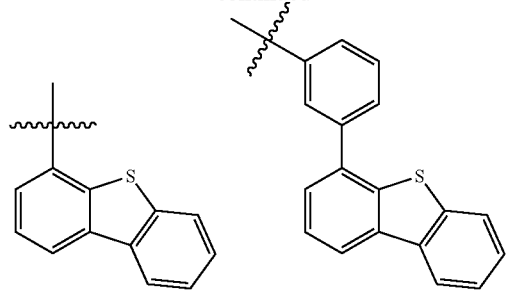
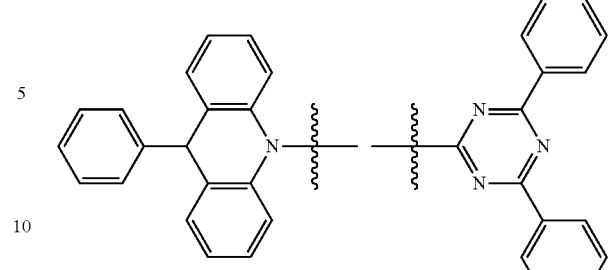
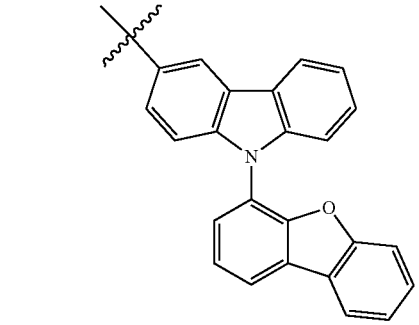
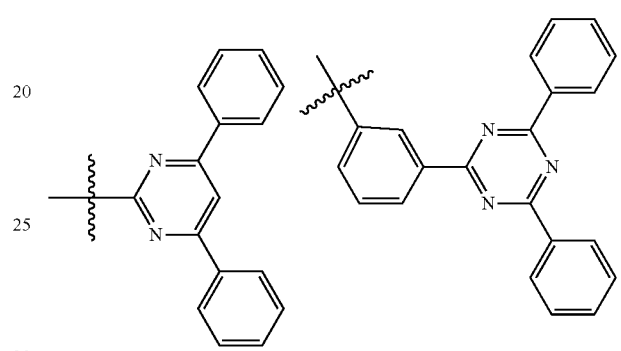
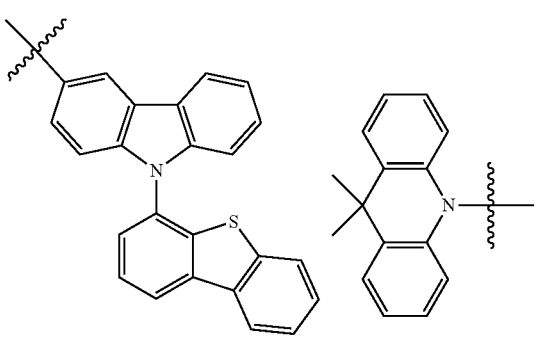
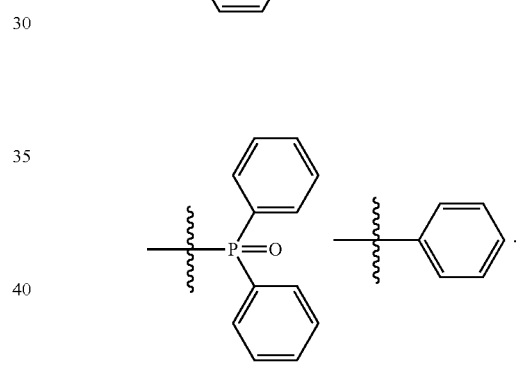
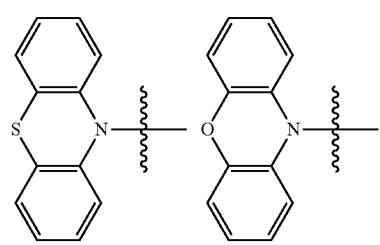
4. The organic compound of claim 1, wherein the organic compound is one of the following compounds:
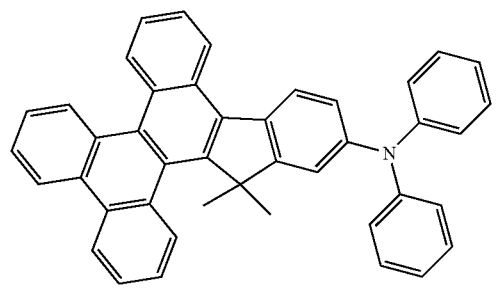
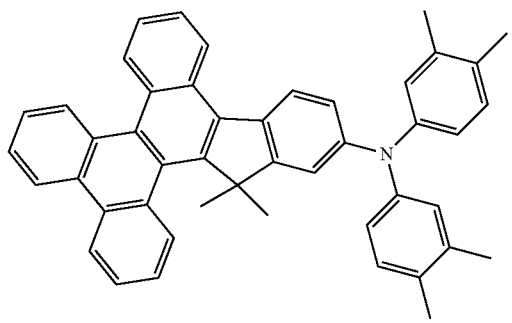

-continued
C3
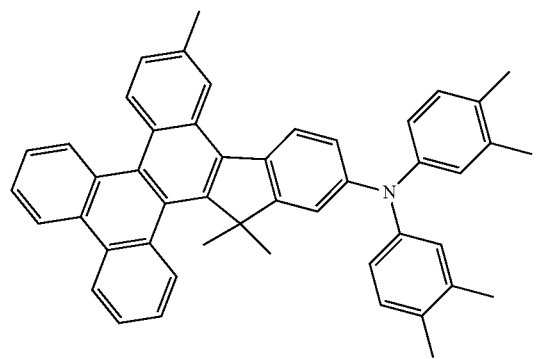
C4
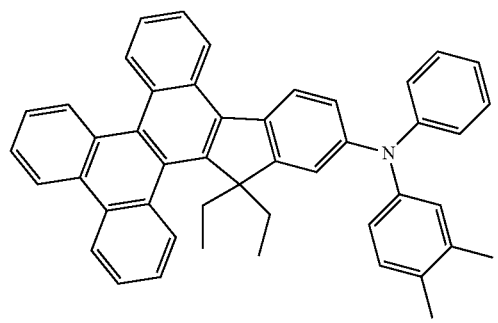
C5
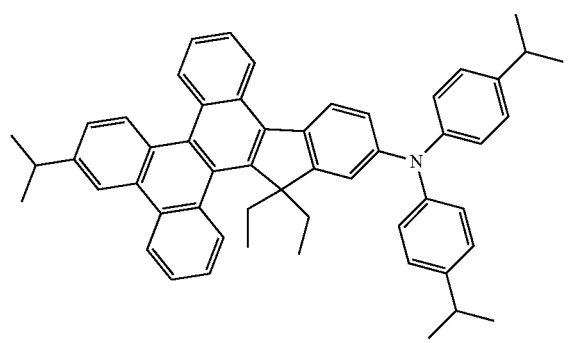
C6
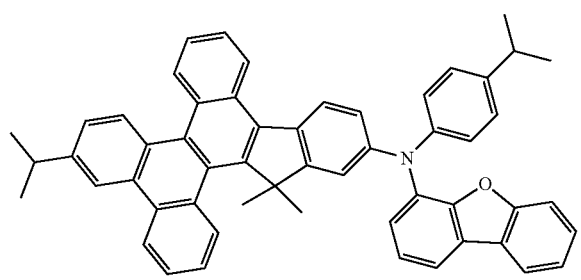
C7
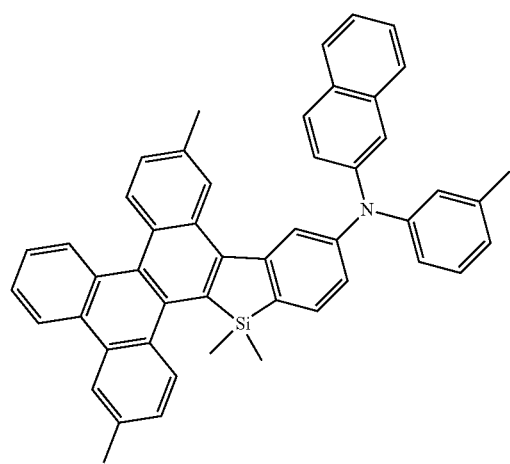
C8
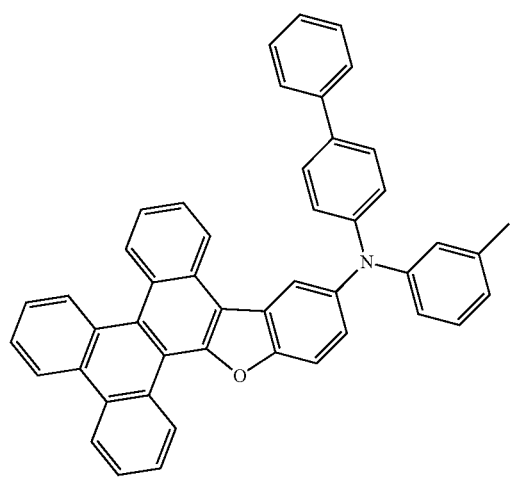

-continued
C9
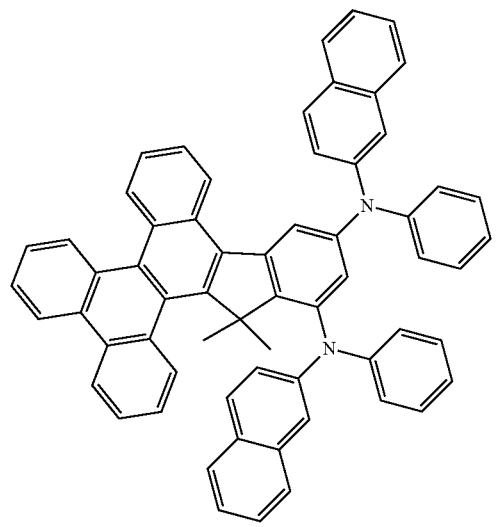
C10
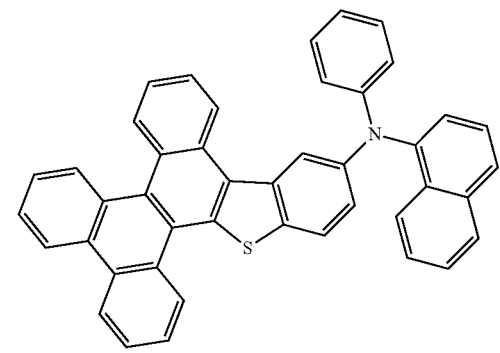
C11
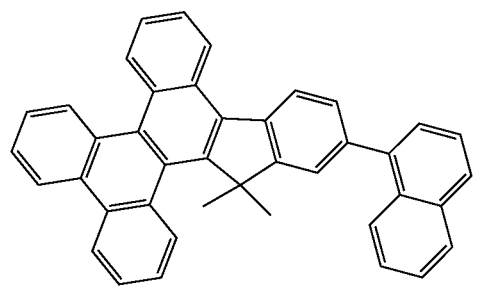
C12
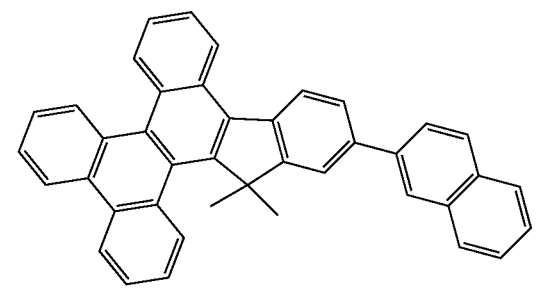
C13
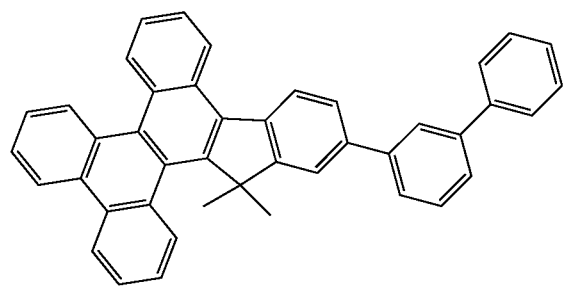
C14
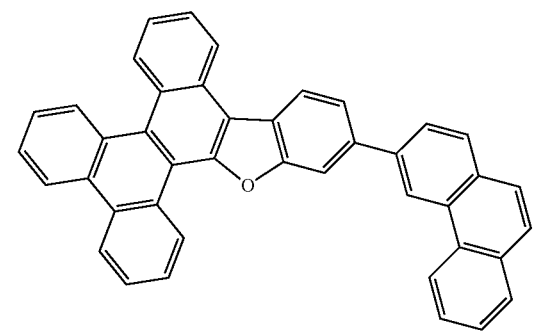
C15
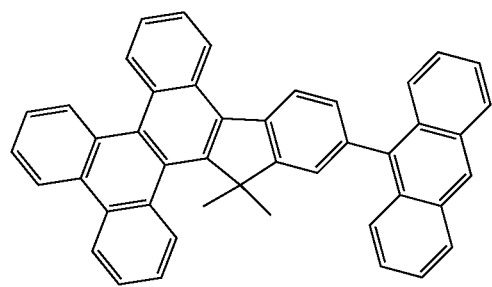
C16
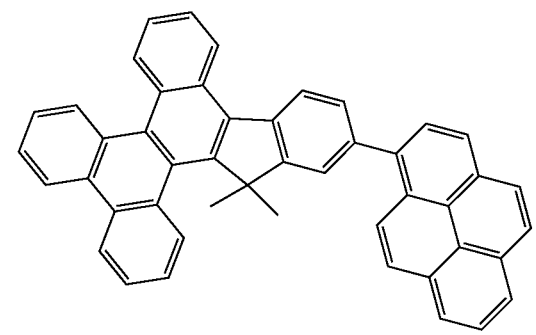

-continued
C17
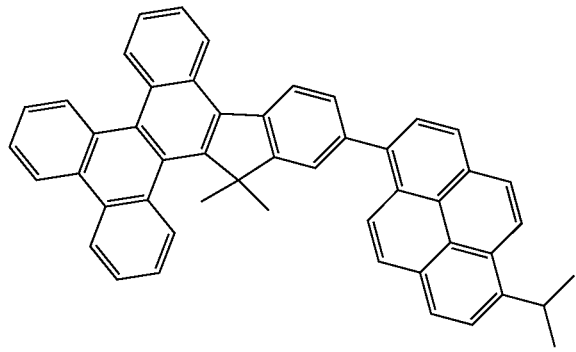
C18
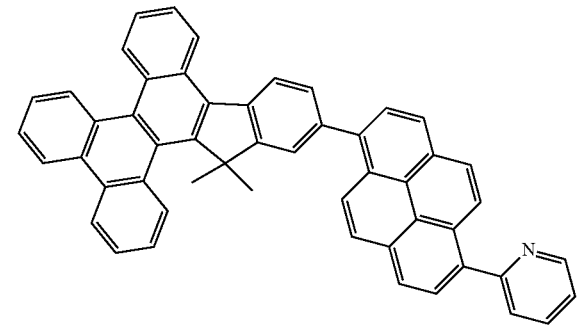
C19
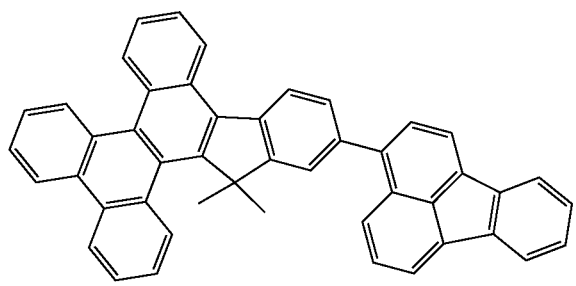
C20
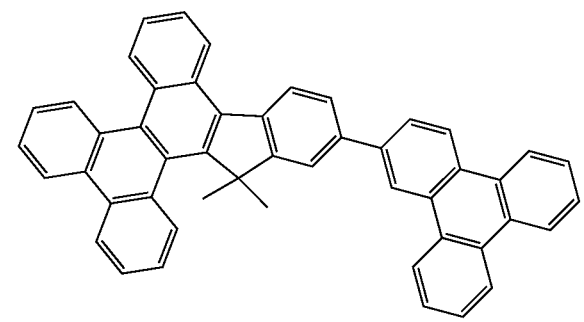
C21
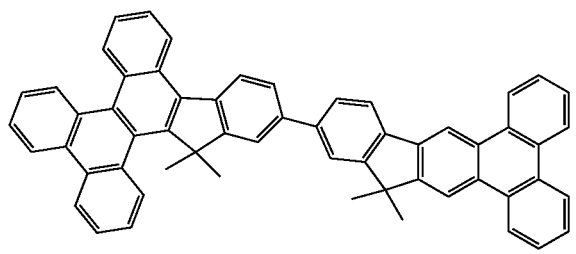
C22
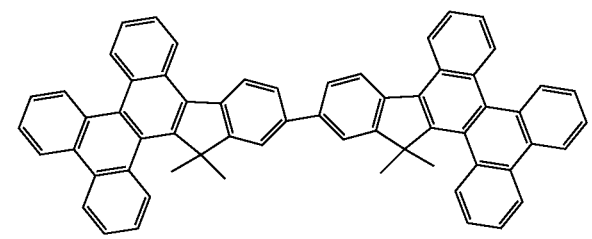
C23
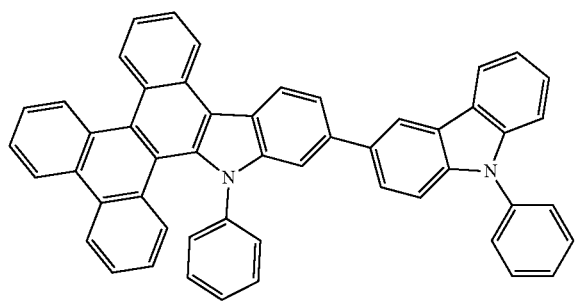
C24
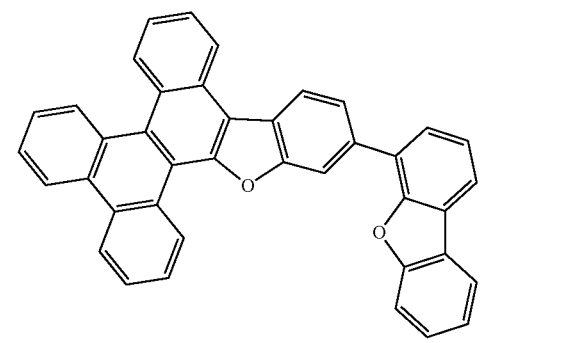

-continued
C25
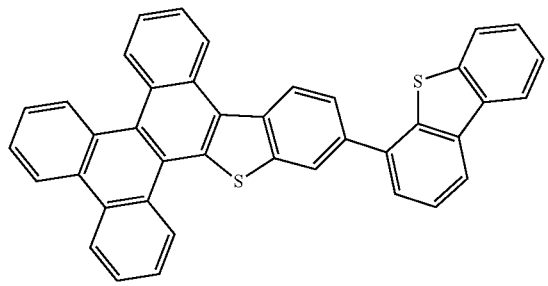
C26
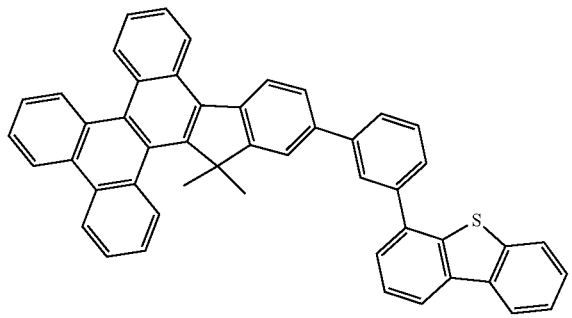
C27
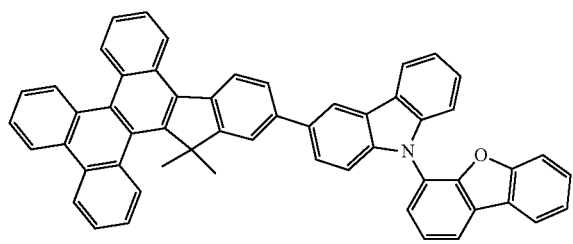
C28
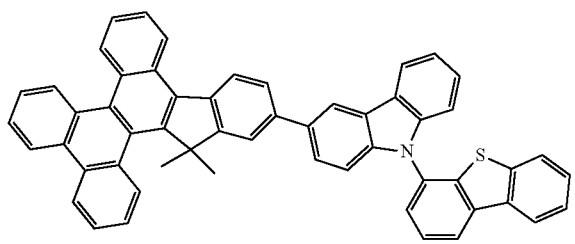
C29
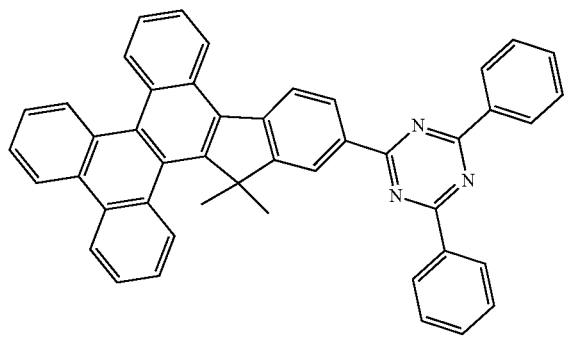
C30
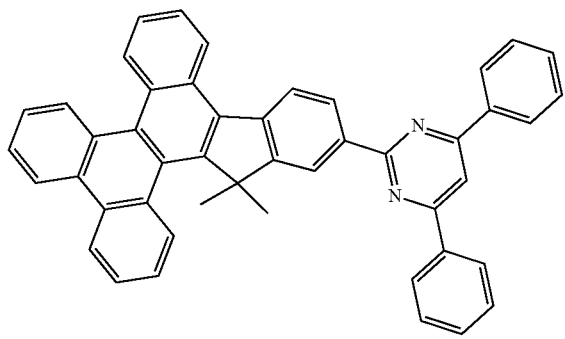
C31
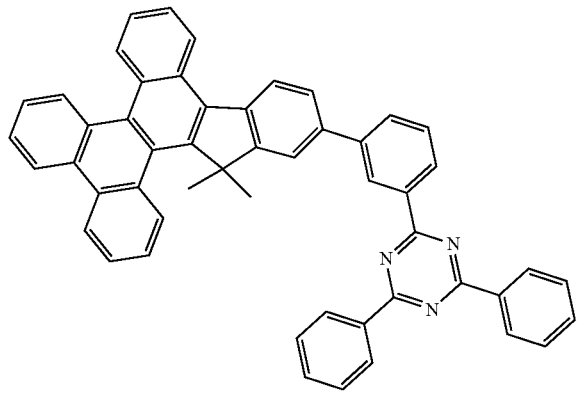
C32
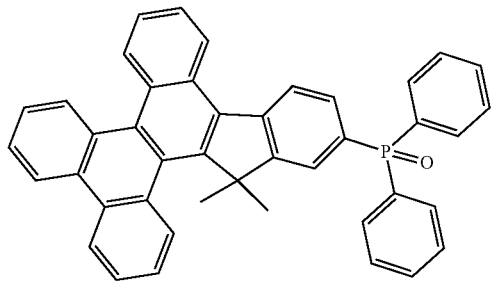

-continued
C33
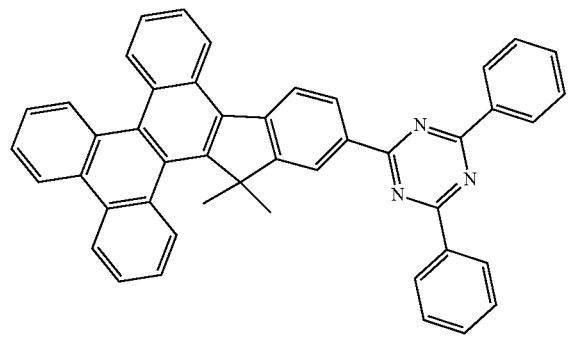
C34
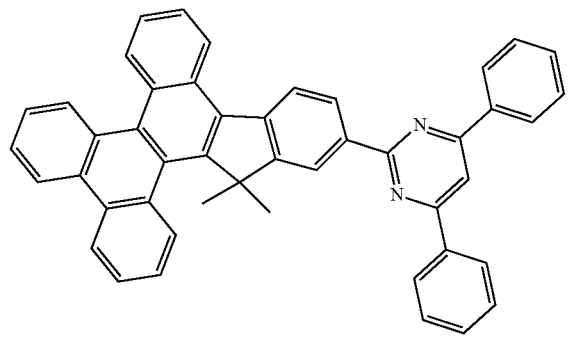
C35
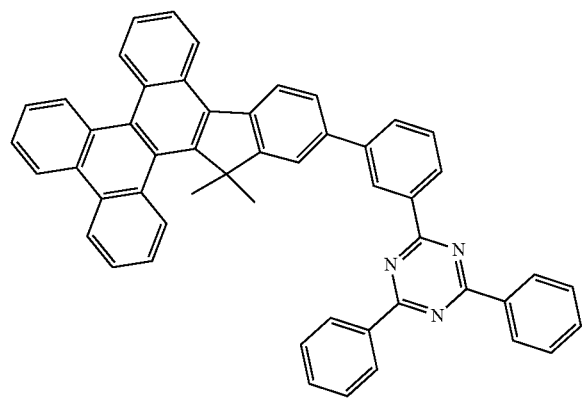
C36
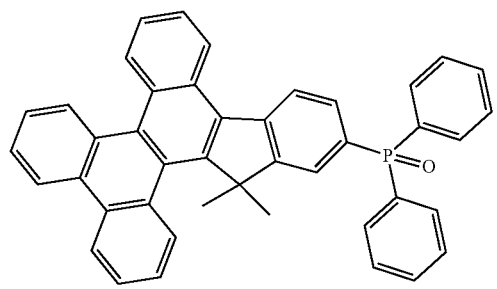
C37
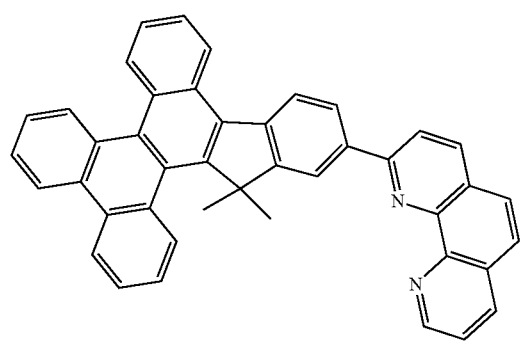
C38
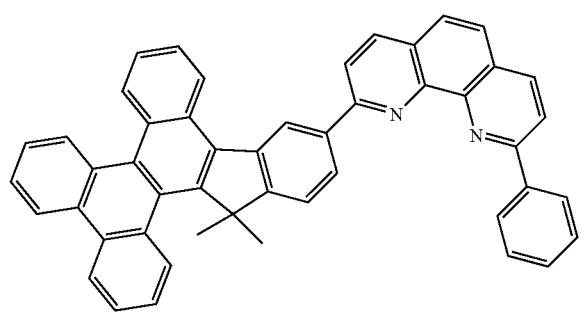
C39
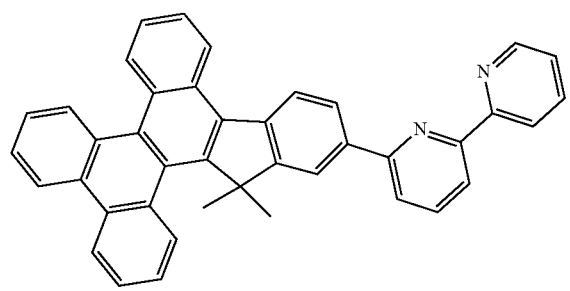
C40
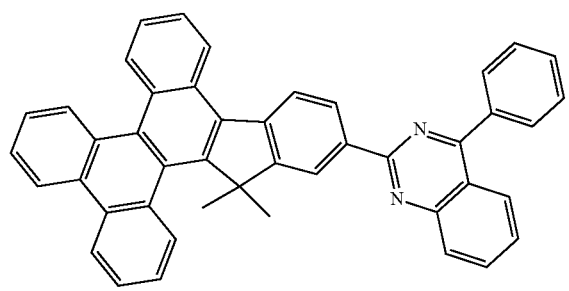

-continued
C41
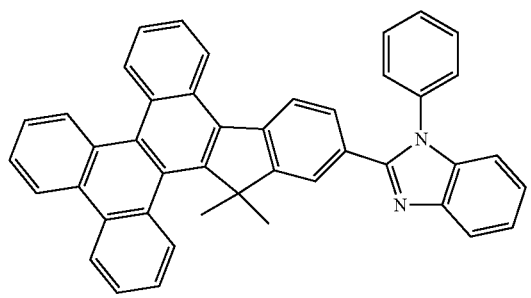
C42
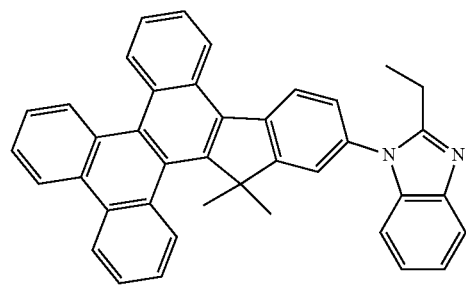
C43
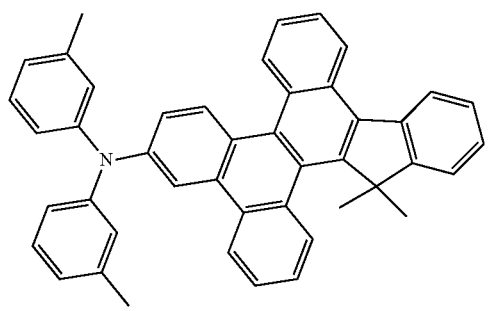
C44
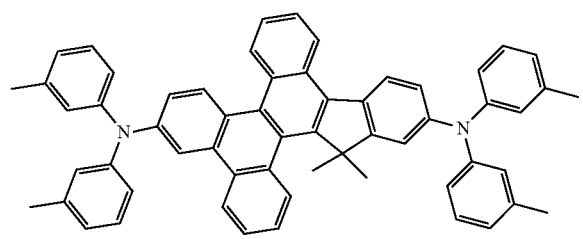
C45
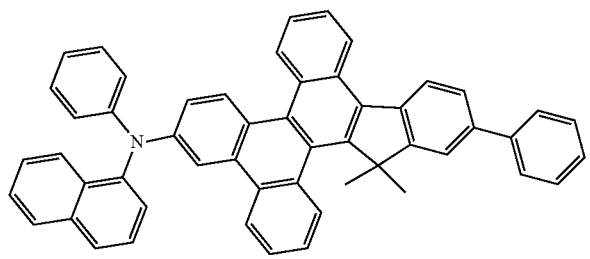
C46
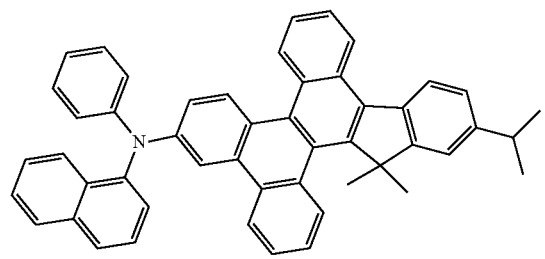
C47
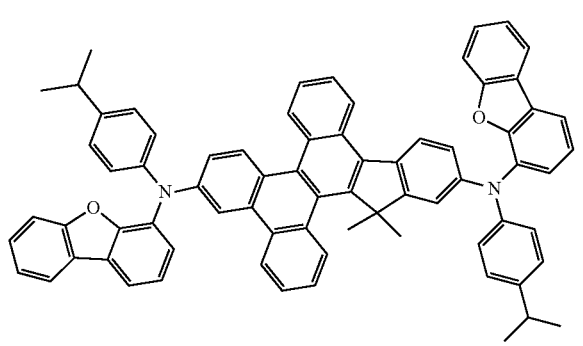
C48
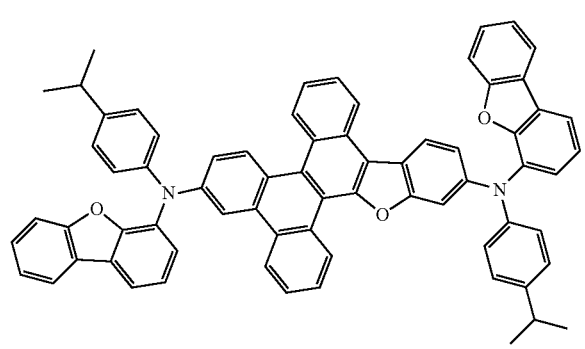
C49
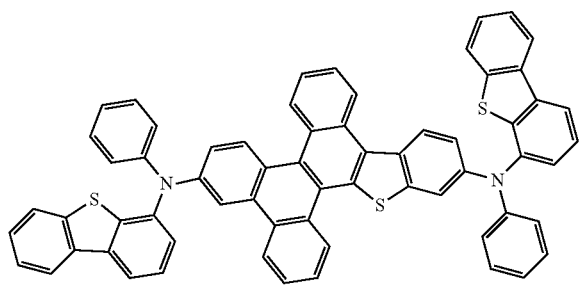
C50
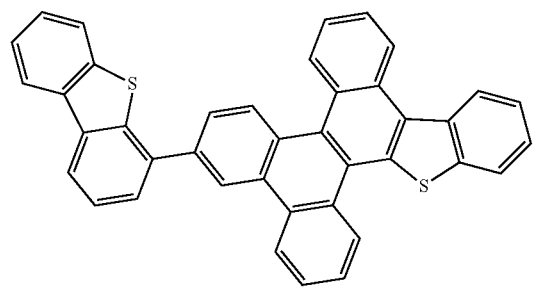

-continued
C51
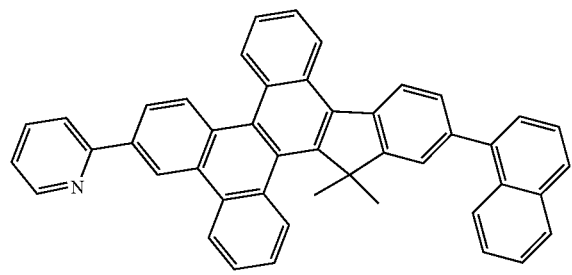
C52
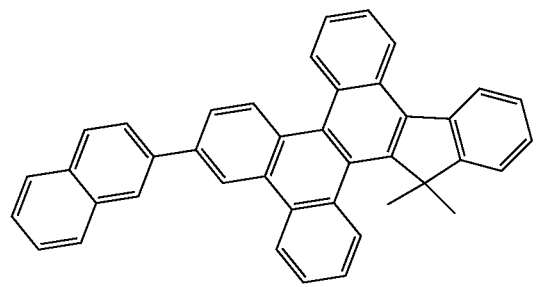
C53
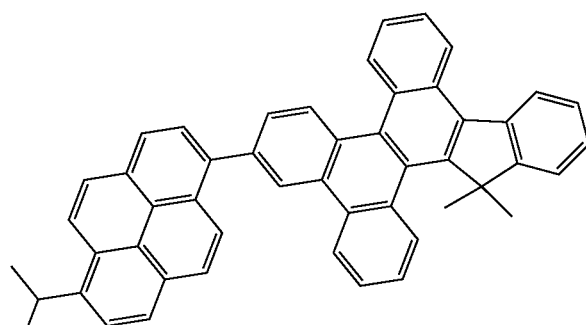
C54
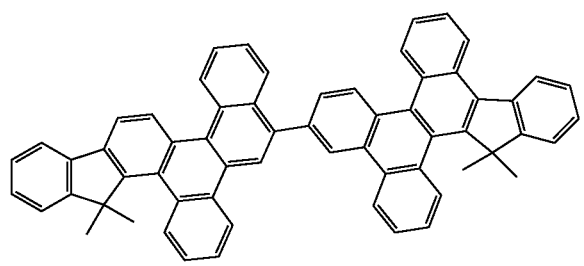
C55
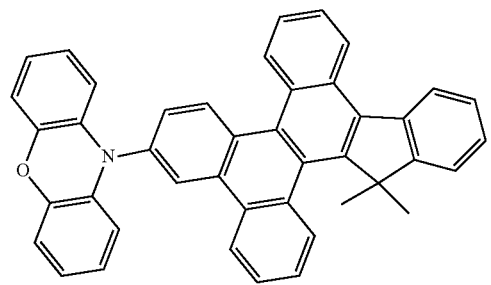
C56
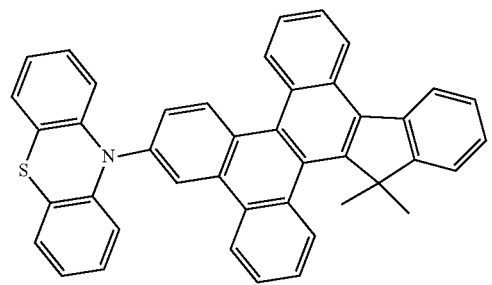
C57
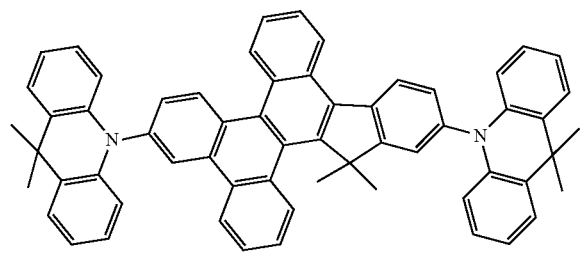
C58
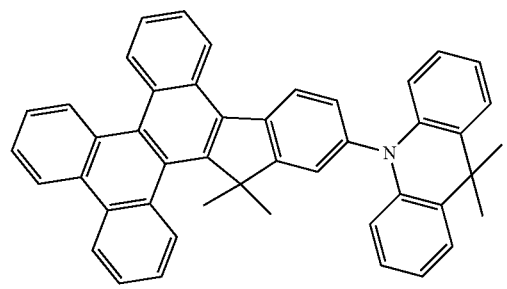
C59
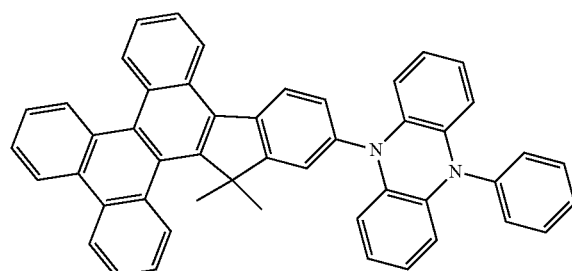
C60
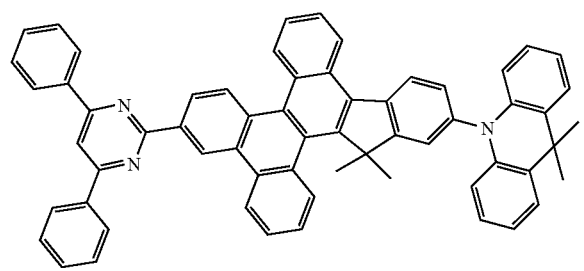

-continued
C61
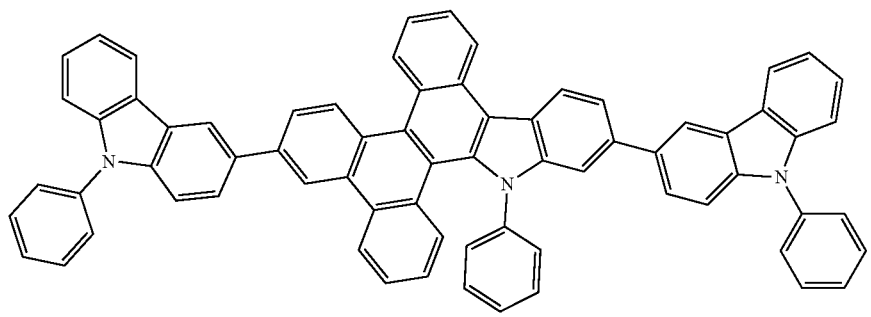
C62
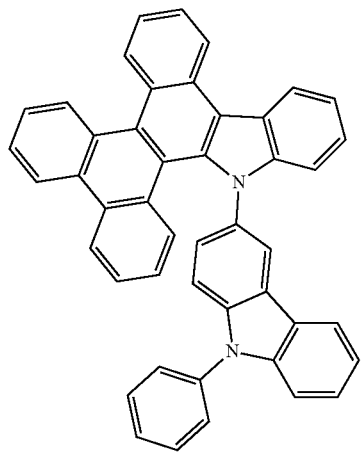
C63
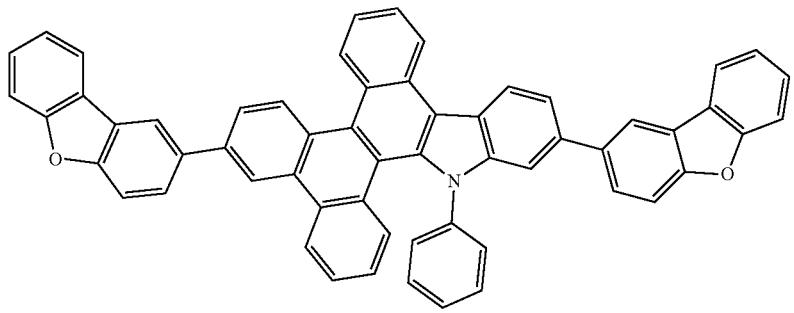
C64
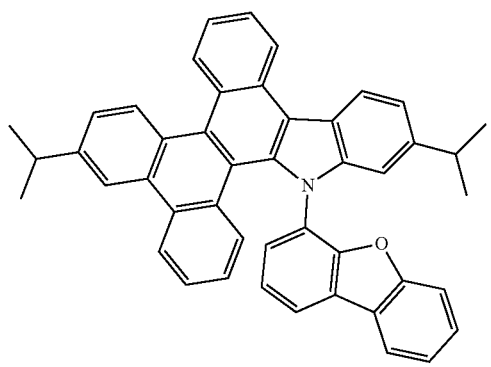
C65
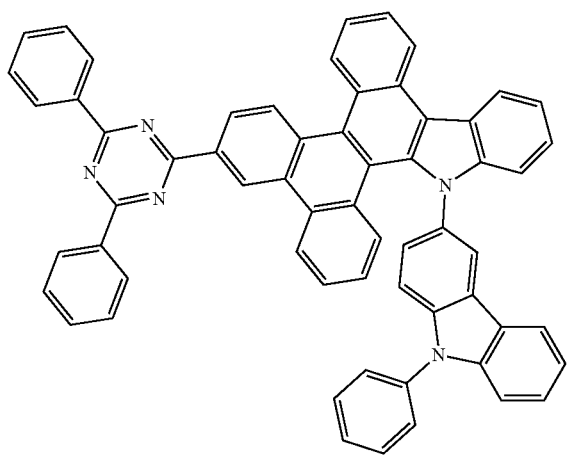

-continued
C66
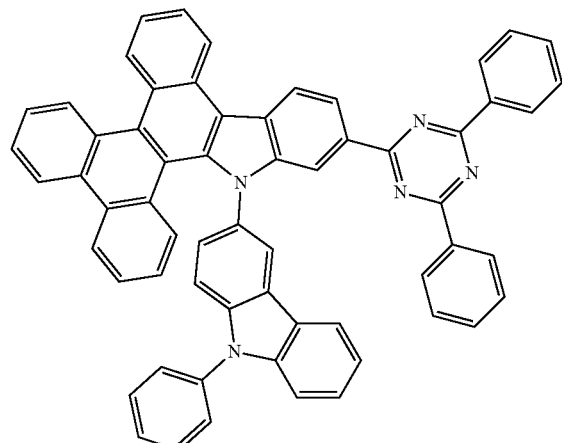
C67
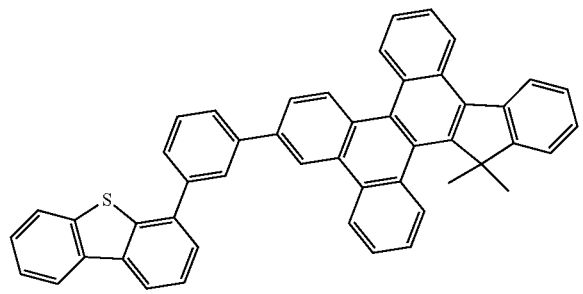
C68
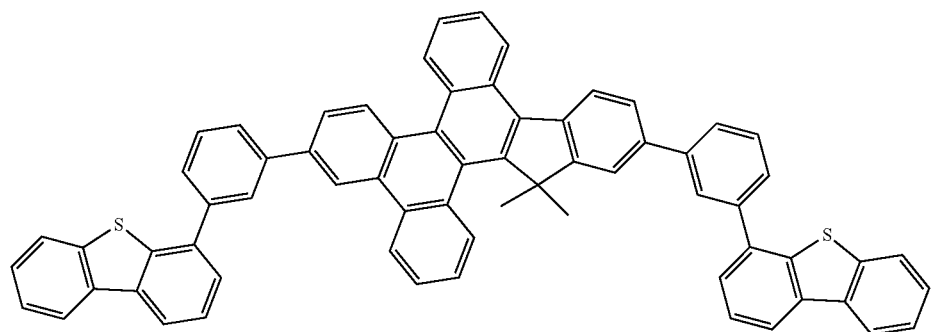
C69
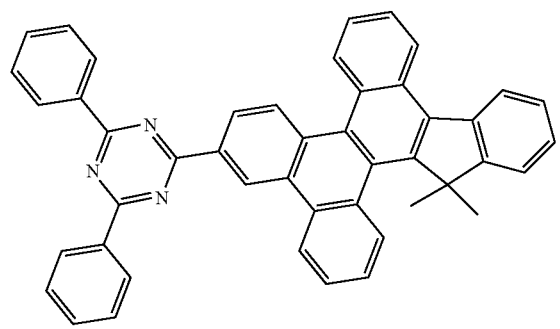
C70
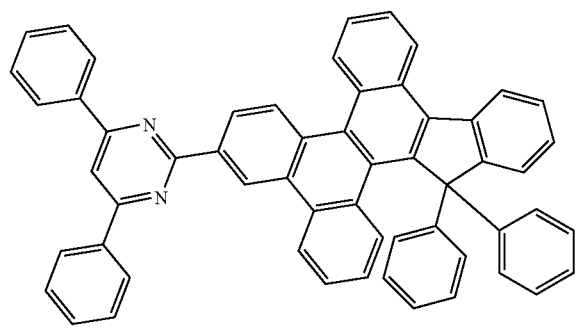
C71
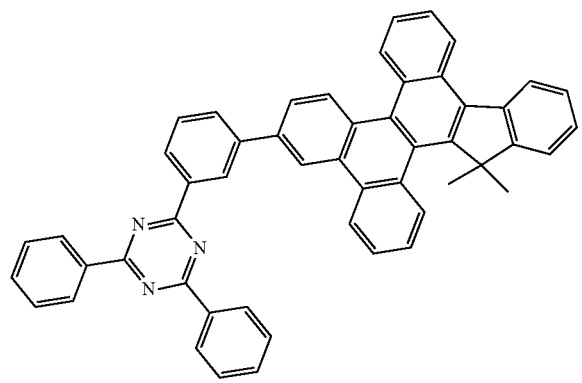
C72
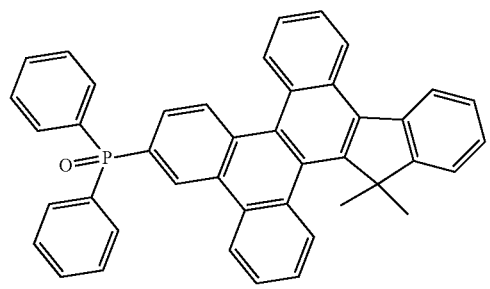

-continued
C73
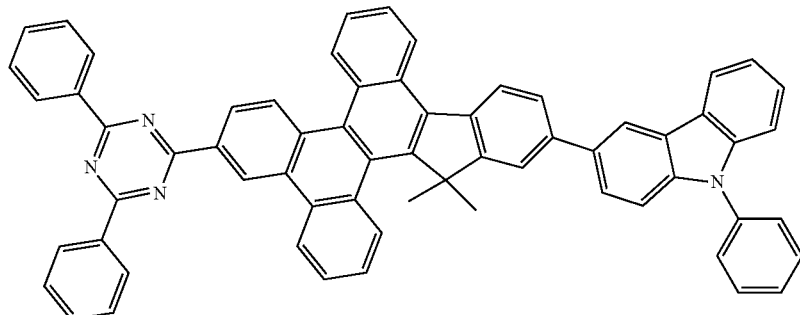
C74
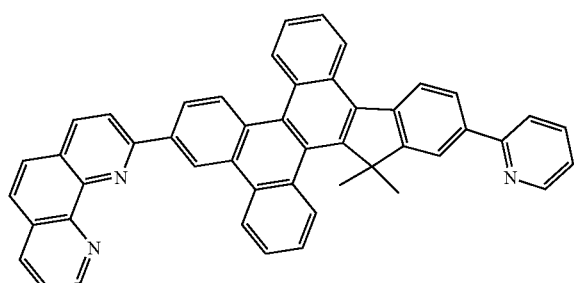
C75
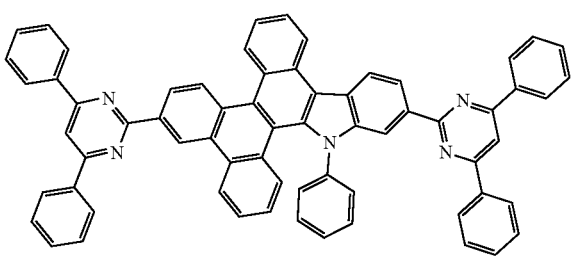
C76
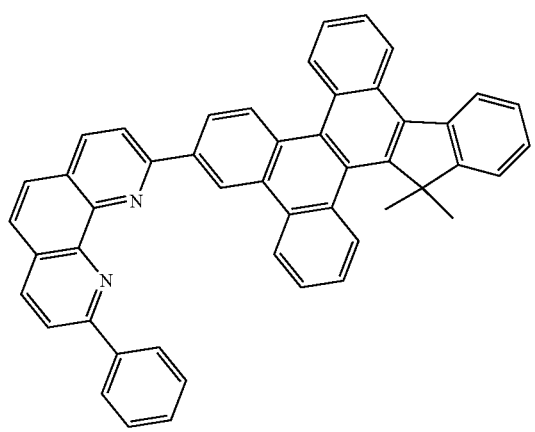
C77
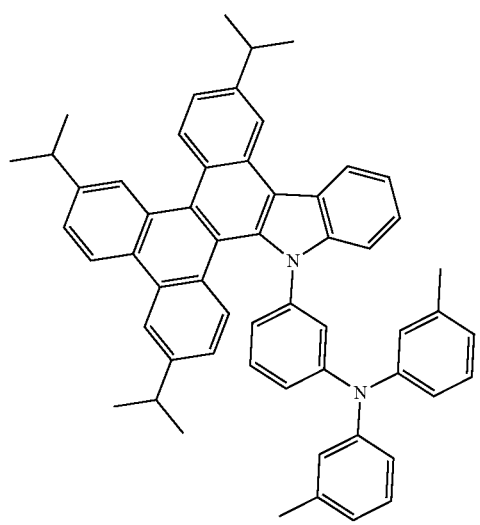
C78
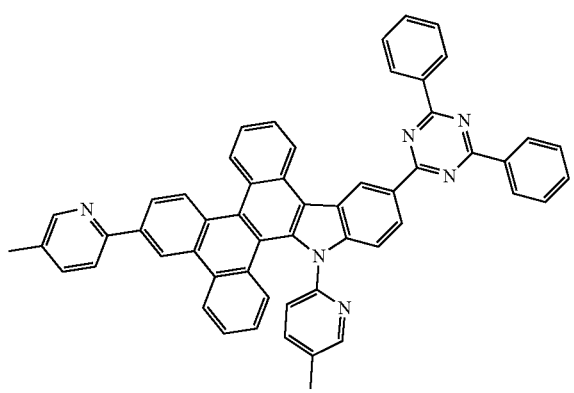
C79
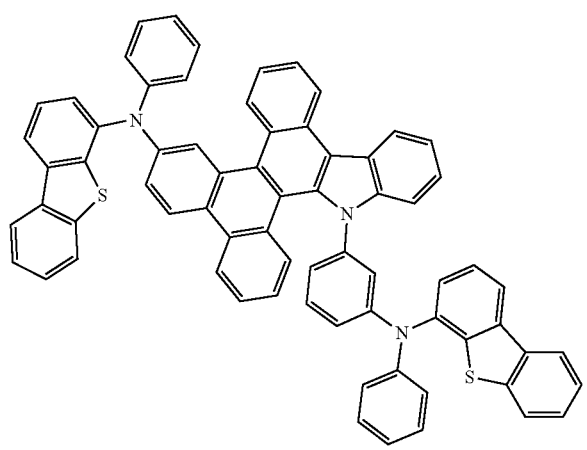

-continued
C80
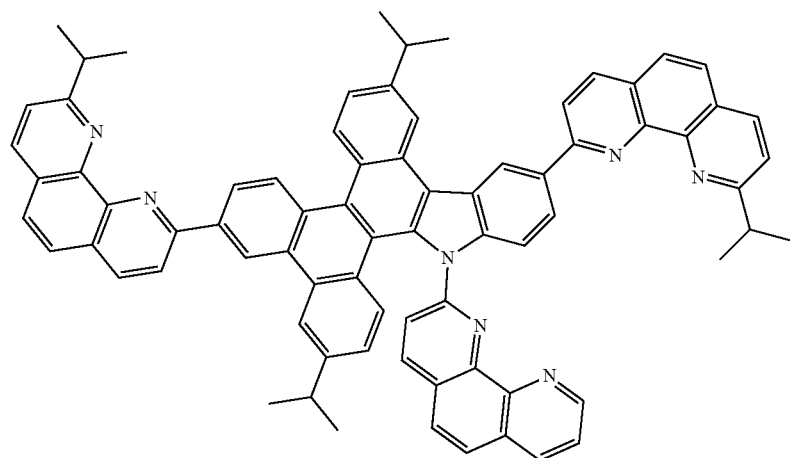
C81 C82
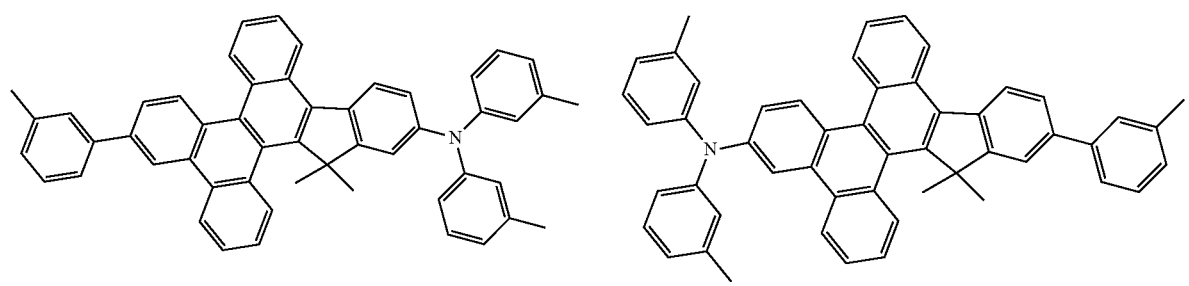
C83 C84
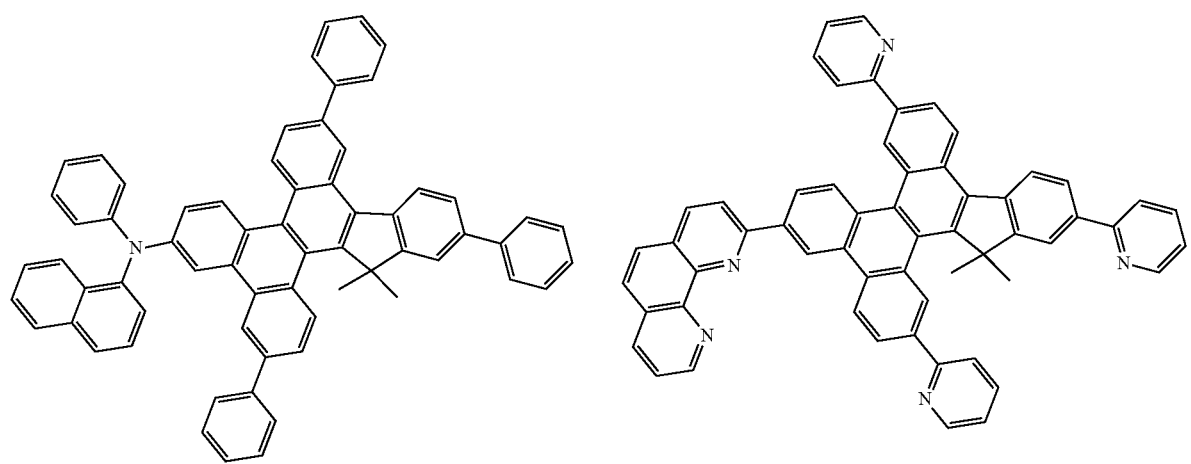

-continued
C85
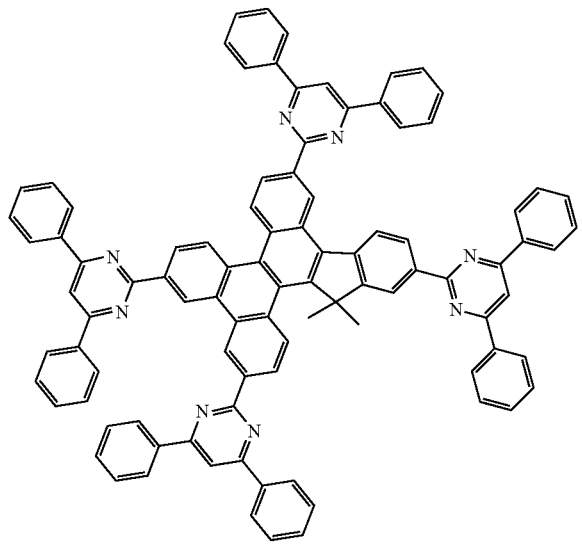
C86
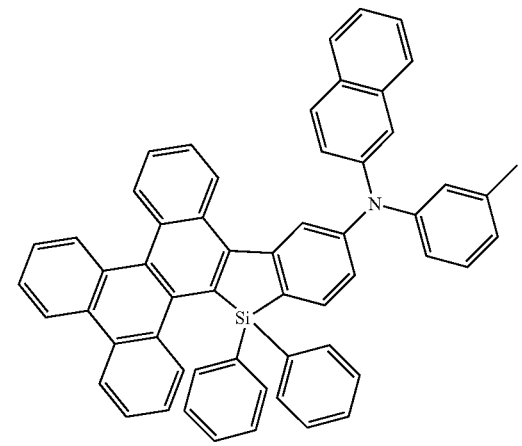
C87
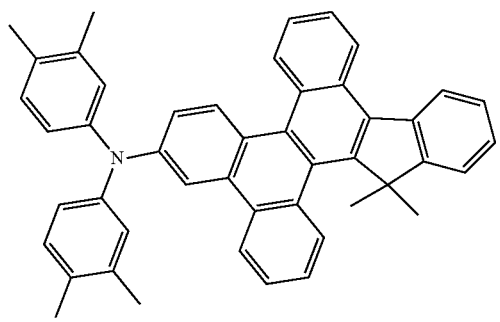
C88
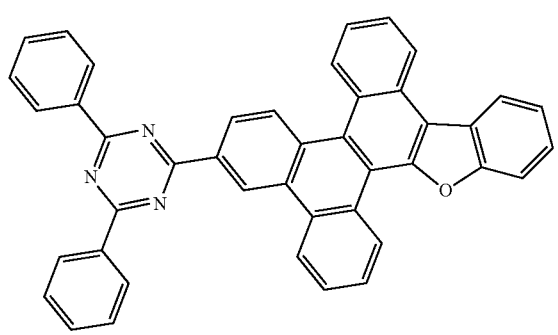
C89
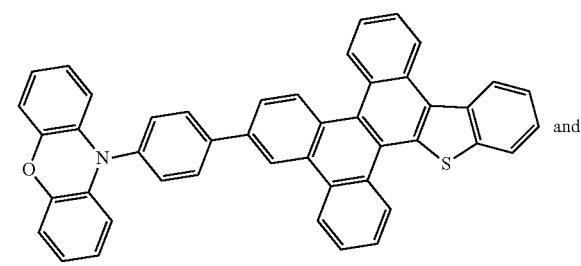
C90
and
C91
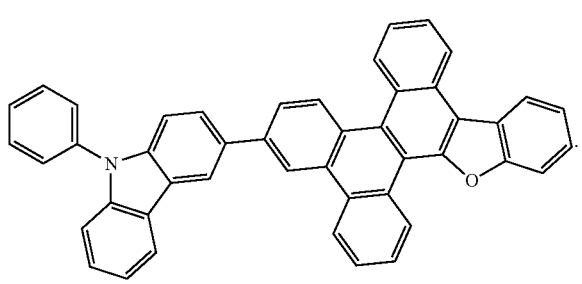.

5. An organic electroluminescence device, comprising a pair of electrodes composed of a cathode and an anode, and a light emitting layer and one or more organic thin film layers between the pair of electrodes, wherein at least one of the light emitting layer and the organic thin film layer comprises the organic compound of claim 1.

6. The organic electroluminescence device of claim 5, wherein the light emitting layer comprising the organic compound of formula (I) is a host material.

7. The organic electroluminescence device of claim 5, wherein the light emitting layer comprising the organic compound of formula (I) is a fluorescent dopant material.

8. The organic electroluminescence device of claim 5, wherein the organic thin film layer comprising the organic compound of formula (I) is an electron transporting layer.

9. The organic electroluminescence device of claim 5, wherein the organic electroluminescence device is a lighting panel.

10. The organic electroluminescence device of claim 5, wherein the organic electroluminescence device is a backlight panel.

* * * * *